(12) United States Patent
Aoyama et al.

(10) Patent No.: US 10,118,048 B2
(45) Date of Patent: Nov. 6, 2018

(54) UTILITY MODULE SYSTEM

(71) Applicant: Physio-Control, Inc., Redmond, WA (US)

(72) Inventors: David Dean Aoyama, Kenmore, WA (US); Ryan William Apperson, Bothell, WA (US); Matthew Lawrence Bielstein, Renton, WA (US); Barry D. Curtin, Seattle, WA (US); John Daynes, Redmond, WA (US); Kevin C. Drew, Snohomish, WA (US); Karen Kraft Langman, Kirkland, WA (US); Mina Lim, Newcastle, WA (US); Neil G. McIlvaine, Seattle, WA (US); E. Thomas McKay, Kent, WA (US); Randy L. Merry, Woodinville, WA (US); Ken Peterson, Bellevue, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 187 days.

(21) Appl. No.: 15/283,966

(22) Filed: Oct. 3, 2016

(65) Prior Publication Data
US 2017/0021183 A1 Jan. 26, 2017

Related U.S. Application Data

(62) Division of application No. 13/690,031, filed on Nov. 30, 2012, now Pat. No. 9,457,197.
(Continued)

(51) Int. Cl.
*A61N 1/00* (2006.01)
*A61N 1/39* (2006.01)
(Continued)

(52) U.S. Cl.
CPC ......... *A61N 1/3925* (2013.01); *A61N 1/3937* (2013.01); *A61N 1/3968* (2013.01);
(Continued)

(58) Field of Classification Search
CPC ............................ A61N 1/3956; A61N 1/3937
(Continued)

(56) References Cited

U.S. PATENT DOCUMENTS 3,724,455 A 4/1973 Unger et al.
3,865,101 A 2/1975 Saper et al.
(Continued)

FOREIGN PATENT DOCUMENTS

EP 0801959 A2 10/1997
EP 0923961 A1 6/1999
(Continued)

OTHER PUBLICATIONS

Final Rejection dated Dec. 15, 2015, U.S. Appl. No. 12/139,359, filed Jun. 13, 2008.
(Continued)

*Primary Examiner* — Nadia A Mahmood
(74) *Attorney, Agent, or Firm* — Lane Powell PC

(57) ABSTRACT

A defibrillator system optimizes the timing and manner of applying a defibrillator charge to a patient based upon data provided to the defibrillator from a utility module or one or more external devices. A parameter module on the utility module provides the defibrillator with patient parameter information. Devices external to the utility module may provide the utility module with coaching data that the utility module may pass through to the defibrillator as a proxy to the external devices. The utility module may also provide external devices with patient data that the utility module may pass through to the external devices as a proxy to the defibrillator on a scheduled or other basis. The utility
(Continued)

DEFIBRILLATION SCENE module may additionally provide a reserve of power to enable defibrillators to be used where power is unavailable and to enable defibrillators to deliver multiple charges more readily anywhere, anytime.

28 Claims, 30 Drawing Sheets

Related U.S. Application Data

(60) Provisional application No. 61/644,303, filed on May 8, 2012, provisional application No. 61/644,308, filed on May 8, 2012, provisional application No. 61/644,314, filed on May 8, 2012, provisional application No. 61/644,321, filed on May 8, 2012.

(51) Int. Cl.
*G16H 40/63* (2018.01)
*G06F 1/16* (2006.01)
*H05K 13/00* (2006.01)
*H04B 7/26* (2006.01)
*G06F 19/00* (2018.01)
*G05B 15/02* (2006.01)
*G16H 40/67* (2018.01)

(52) U.S. Cl.
CPC ......... *A61N 1/3975* (2013.01); *A61N 1/3987* (2013.01); *A61N 1/3993* (2013.01); *G05B 15/02* (2013.01); *G06F 1/1632* (2013.01); *G06F 19/00* (2013.01); *G06F 19/3418* (2013.01); *G16H 40/63* (2018.01); *G16H 40/67* (2018.01); *H04B 7/26* (2013.01); *H05K 13/00* (2013.01); *H05K 999/99* (2013.01); *F04C 2270/041* (2013.01); *Y10T 29/49826* (2015.01)

(58) Field of Classification Search
USPC .................................................. 607/2, 6, 7
See application file for complete search history.

(56) References Cited

U.S. PATENT DOCUMENTS

| | | |
|---|---|---|
| 4,096,856 A | 6/1978 | Smith et al. |
| 4,635,639 A | 1/1987 | Hakala et al. |
| 4,916,439 A | 4/1990 | Estes et al. |
| 5,012,411 A | 4/1991 | Policastro et al. |
| 5,078,134 A | 1/1992 | Heilman et al. |
| 5,105,821 A | 4/1992 | Reyes et al. |
| 5,311,449 A | 5/1994 | Adams et al. |
| 5,321,837 A | 6/1994 | Daniel et al. |
| 5,419,336 A | 5/1995 | Margison et al. |
| 5,470,343 A | 11/1995 | Fincke et al. |
| 5,549,115 A | 8/1996 | Morgan et al. |
| 5,549,659 A | 8/1996 | Johansen et al. |
| 5,565,759 A | 10/1996 | Dunstan et al. |
| 5,593,426 A | 1/1997 | Morgan et al. |
| 5,674,252 A | 10/1997 | Morgan et al. |
| 5,680,863 A | 10/1997 | Morgan et al. |
| 5,683,423 A | 11/1997 | Post et al. |
| 5,685,314 A | 11/1997 | Geheb et al. |
| 5,715,823 A | 2/1998 | Wood et al. |
| 5,724,985 A | 3/1998 | Snell et al. |
| 5,749,902 A | 5/1998 | Olson et al. |
| 5,749,913 A | 5/1998 | Cole et al. |
| 5,782,878 A | 7/1998 | Morgan et al. |
| 5,787,155 A | 7/1998 | Luna et al. |
| 5,814,089 A | 9/1998 | Stokes et al. |
| 5,836,993 A | 11/1998 | Cole et al. |
| 5,857,967 A | 1/1999 | Frid et al. |
| 5,879,374 A | 3/1999 | Powers et al. |
| 5,891,046 A | 4/1999 | Cyrus et al. |
| 5,891,049 A | 4/1999 | Cyrus et al. |
| 5,899,866 A | 5/1999 | Cyrus et al. |
| 5,921,938 A | 7/1999 | Aoyama et al. |
| 5,929,601 A | 7/1999 | Kaib et al. |
| 5,950,632 A | 9/1999 | Reber et al. |
| 5,951,485 A | 9/1999 | Cyrus et al. |
| D414,869 S | 10/1999 | Daynes et al. |
| 5,999,493 A | 12/1999 | Olson et al. |
| 6,024,699 A | 2/2000 | Surwit et al. |
| 6,041,257 A | 3/2000 | MacDuff et al. |
| 6,047,207 A | 4/2000 | MacDuff et al. |
| 6,057,758 A | 5/2000 | Dempsey et al. |
| 6,102,856 A | 8/2000 | Groff et al. |
| 6,111,505 A | 8/2000 | Wagener et al. |
| 6,134,468 A | 10/2000 | Morgan et al. |
| 6,141,584 A | 10/2000 | Rockwell et al. |
| 6,144,922 A | 11/2000 | Douglas et al. |
| 6,150,951 A | 11/2000 | Olejniczak et al. |
| 6,157,313 A | 12/2000 | Emmermann et al. |
| 6,183,417 B1 | 2/2001 | Geheb et al. |
| 6,188,407 B1 | 2/2001 | Smith et al. |
| 6,201,992 B1 | 3/2001 | Freeman et al. |
| 6,223,077 B1 | 4/2001 | Schweizer et al. |
| 6,275,737 B1 | 8/2001 | Mann et al. |
| 6,301,501 B1 | 10/2001 | Cronin et al. |
| 6,301,502 B1 | 10/2001 | Owen et al. |
| 6,304,780 B1 | 10/2001 | Owen et al. |
| 6,321,113 B1 | 11/2001 | Parker et al. |
| 6,323,782 B1 | 11/2001 | Stephens et al. |
| 6,334,070 B1 | 12/2001 | Nova et al. |
| 6,336,900 B1 | 1/2002 | Alleckson et al. |
| D455,492 S | 4/2002 | Daynes et al. |
| 6,370,428 B1 | 4/2002 | Snyder et al. |
| 6,374,138 B1 | 4/2002 | Owen et al. |
| 6,377,223 B1 | 4/2002 | Clapp et al. |
| 6,381,492 B1 | 4/2002 | Rockwell et al. |
| 6,402,691 B1 | 6/2002 | Peddicord et al. |
| 6,405,083 B1 | 6/2002 | Rockwell et al. |
| 6,422,669 B1 | 7/2002 | Salvation et al. |
| 6,427,083 B1 | 7/2002 | Owen et al. |
| 6,434,429 B1 | 8/2002 | Kraus et al. |
| 6,438,417 B1 | 8/2002 | Rockwell et al. |
| 6,441,747 B1 | 8/2002 | Khair et al. |
| 6,493,581 B2 | 12/2002 | Russell et al. |
| 6,524,241 B2 | 2/2003 | Iliff et al. |
| 6,571,128 B2 | 5/2003 | Lebel et al. |
| 6,591,135 B2 | 7/2003 | Palmer et al. |
| 6,594,634 B1 | 7/2003 | Hampton et al. |
| 6,597,948 B1 | 7/2003 | Rockwell et al. |
| 6,668,192 B1 | 12/2003 | Parker et al. |
| 6,771,172 B1 | 8/2004 | Robinson et al. |
| 6,957,102 B2 | 10/2005 | Silver et al. |
| 6,978,181 B1 | 12/2005 | Snell et al. |
| 7,006,865 B1 | 2/2006 | Cohen et al. |
| 7,110,825 B2 | 9/2006 | Vaynberg et al. |
| 7,570,994 B2 | 8/2009 | Tamura et al. |
| 8,040,246 B2 | 10/2011 | Graves et al. |
| 8,054,177 B2 | 10/2011 | Graves et al. |
| D649,644 S | 11/2011 | Chai et al. |
| D658,296 S | 4/2012 | Matheson et al. |
| 8,154,246 B1 | 4/2012 | Heitmann |
| D693,006 S | 11/2013 | Arimitsu et al. |
| 8,594,784 B2 | 11/2013 | Schwibner et al. |
| 9,155,902 B2 | 10/2015 | Schwibner et al. |
| 9,168,386 B2 | 10/2015 | Schwibner et al. |
| 9,289,621 B2 | 3/2016 | Aoyama et al. |
| 2001/0041920 A1 | 11/2001 | Starkweather et al. |
| 2002/0103508 A1 | 8/2002 | Mathur et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0123673 A1 | 9/2002 | Webb et al. |
| 2002/0128689 A1 | 9/2002 | Connelly et al. |
| 2002/0128691 A1 | 9/2002 | Connelly et al. |
| 2002/0133086 A1 | 9/2002 | Connelly et al. |
| 2002/0133199 A1 | 9/2002 | MacDonald et al. |
| 2002/0133200 A1 | 9/2002 | Weiner et al. |

(56) References Cited

U.S. PATENT DOCUMENTS

| | | |
|---|---|---|
| 2002/0133201 A1 | 9/2002 | Connelly et al. |
| 2002/0133202 A1 | 9/2002 | Connelly et al. |
| 2002/0133208 A1 | 9/2002 | Connelly et al. |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138103 A1 | 9/2002 | Mulhauser et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147470 A1 | 10/2002 | Weiner et al. |
| 2002/0177793 A1 | 11/2002 | Sherman et al. |
| 2002/0183796 A1 | 12/2002 | Connelly et al. |
| 2002/0198569 A1 | 12/2002 | Foster et al. |
| 2003/0025602 A1 | 2/2003 | Medema et al. |
| 2003/0028219 A1 | 2/2003 | Powers et al. |
| 2003/0045905 A1 | 3/2003 | Daynes et al. |
| 2003/0050538 A1 | 3/2003 | Naghavi et al. |
| 2003/0058097 A1 | 3/2003 | Saltzstein et al. |
| 2003/0088275 A1 | 5/2003 | Palmer et al. |
| 2003/0097160 A1 | 5/2003 | Caby et al. |
| 2003/0109904 A1 | 6/2003 | Silver et al. |
| 2003/0167074 A1 | 9/2003 | Merry |
| 2003/0212311 A1 | 11/2003 | Nova et al. |
| 2004/0049233 A1 | 3/2004 | Edwards |
| 2004/0096808 A1 | 5/2004 | Price et al. |
| 2004/0102167 A1 | 5/2004 | Shim et al. |
| 2004/0111122 A1 | 6/2004 | Daynes et al. |
| 2004/0122476 A1 | 6/2004 | Wung et al. |
| 2004/0162586 A1 | 8/2004 | Covey et al. |
| 2004/0204743 A1 | 10/2004 | McGrath et al. |
| 2005/0075671 A1 | 4/2005 | Vaisnys et al. |
| 2005/0124866 A1 | 6/2005 | Elaz et al. |
| 2005/0288571 A1 | 12/2005 | Perkins et al. |
| 2006/0069326 A1 | 3/2006 | Heath |
| 2006/0142808 A1 | 6/2006 | Pearce et al. |
| 2006/0149321 A1 | 7/2006 | Merry et al. |
| 2006/0149323 A1 | 7/2006 | Merry et al. |
| 2006/0173498 A1 | 8/2006 | Banville |
| 2007/0213775 A1 | 9/2007 | Snyder |
| 2008/0077185 A1 | 3/2008 | Pearce et al. |
| 2008/0183229 A1 | 7/2008 | Neumiller et al. |
| 2008/0221397 A1 | 9/2008 | McMahon et al. |
| 2008/0221930 A1 | 9/2008 | Wekell et al. |
| 2009/0089078 A1 | 7/2009 | Bursey et al. |
| 2009/0264948 A1 | 10/2009 | Tamura et al. |
| 2009/0274384 A1 | 11/2009 | Jakobovits et al. |
| 2009/0295326 A1 | 12/2009 | Daynes et al. |
| 2010/0114236 A1 | 5/2010 | Jiang et al. |
| 2010/0131482 A1 | 5/2010 | Linthicum et al. |
| 2010/0185547 A1 | 7/2010 | Scholar et al. |
| 2011/0153343 A1 | 6/2011 | Tremblay et al. |
| 2011/0172550 A1 | 7/2011 | Martin et al. |
| 2011/0208259 A1 | 8/2011 | Pearce et al. |
| 2011/0295078 A1 | 12/2011 | Reid et al. |
| 2012/0123223 A1 | 5/2012 | Freeman et al. |
| 2012/0172700 A1 | 7/2012 | Krishnan et al. |
| 2012/0239420 A1 | 9/2012 | Stapelfeldt et al. |
| 2012/0239428 A1 | 9/2012 | James et al. |
| 2013/0093829 A1 | 4/2013 | Rosenblatt et al. |
| 2013/0096649 A1 | 4/2013 | Martin et al. |
| 2013/0231947 A1 | 9/2013 | Shusterman et al. |
| 2014/0272860 A1 | 9/2014 | Peterson et al. |

FOREIGN PATENT DOCUMENTS

| | | |
|---|---|---|
| EP | 1228782 | 8/2002 |
| EP | 1250944 | 10/2002 |
| WO | WO0070889 | 11/2000 |
| WO | WO01/66182 | 9/2001 |
| WO | WO02/060529 | 8/2002 |
| WO | 2004093979 A1 | 11/2004 |
| WO | WO2005058413 | 6/2005 |
| WO | WO2005058416 | 6/2005 |
| WO | WO03/009895 | 2/2013 |
| WO | 13056194 A1 | 4/2013 |

OTHER PUBLICATIONS

Amendment dated Sep. 29, 2015, U.S. Appl. No. 12/139,359, filed Jun. 13, 2008.
Non-Final Rejection dated Jun. 29, 2015, U.S. Appl. No. 12/139,359, filed Jun. 13, 2008.
Amendment dated May 26, 2015, U.S. Appl. No. 12/139,359, filed Jun. 13, 2008.
Final Rejection dated Mar. 22, 2011, U.S. Appl. No. 12/139,359, filed Jun. 13, 2008.
Amendment dated Jan. 5, 2011, U.S. Appl. No. 12/139,359, filed Jun. 13, 2008.
Non-Final Rejection dated Oct. 5, 2010, U.S. Appl. No. 12/139,359, filed Jun. 13, 2008.
Final Rejection dated Aug. 2, 2006, U.S. Appl. No. 10/378,001, filed Feb. 28, 2003.
Amendment dated May 30, 2006, U.S. Appl. No. 10/378,001, filed Feb. 28, 2003.
Non-Final Rejection dated Dec. 27, 2005, U.S. Appl. No. 10/378,001, filed Feb. 28, 2003.
Response to Rejection dated Nov. 21, 2005, U.S. Appl. No. 10/378,001, filed Feb. 28, 2001.
Requirement for Restriction dated Oct. 21, 2005, U.S. Appl. No. 10/378,001, filed Feb. 28, 2003.
Communication from the Examining Division dated Aug. 18, 2008, Application No. EP1617896.
Reply to Communication from the Examining Division dated Dec. 16, 2008, Application No. EP1617896.
Decision to Grant dated Aug. 6, 2009, Application No. EP1617896.
International Preliminary Report on Patentability dated Apr. 18, 2016, International Application No. PCT/US15/055095, international filed Oct. 12, 2015.
International Search Report & Written Opinion dated Apr. 21, 2016, International Application No. PCT/US15/055095, international filed Oct. 12, 2015.
International Preliminary Report on Patentability dated Nov. 11, 2014, PCT/US2012/071436, dated Apr. 10, 2013.
International Preliminary Report on Patentability dated Nov. 11, 2014, PCT/US2012/071461, dated Apr. 10, 2013, 14 pages.
International Preliminary Report on Patentability dated Nov. 11, 2014, PCT/US2012/071448, dated Feb. 8, 2013, 11 pages.
International Preliminary Report on Patentability dated Nov. 11, 2014, PCT/US2012/071450, dated May 24, 2013.
Non-Final Action dated Mar. 13, 2017, U.S. Appl. No. 15/057,468, filed Mar. 1, 2016.
Non-Final Action dated Apr. 14, 2016, U.S. Appl. No. 15/057,468, filed Mar. 1, 2016.
Notice of Allowance dated Jan. 13, 2017, U.S. Appl. No. 15/057,468, filed Mar. 1, 2016.
Notice of Allowance dated Nov. 21, 2016, U.S. Appl. No. 15/057,468, filed Mar. 1, 2016.
Notice of Allowance dated Aug. 31, 2016, U.S. Appl. No. 15/057,468, filed Mar. 1, 2016.
Amendment dated Jan. 13, 2017, U.S. Appl. No. 15/057,468, filed Mar. 1, 2016.
Amendment dated Nov. 21, 2016, U.S. Appl. No. 15/057,468, filed Mar. 1, 2016.
Amendment dated Jan. 6, 2017, U.S. Appl. No. 15/057,468, filed Mar. 1, 2016.
Amendment dated Oct. 31, 2016, U.S. Appl. No. 15/057,468, filed Mar. 1, 2016.
Amendment dated Jul. 8, 2016, U.S. Appl. No. 15/057,468, filed Mar. 1, 2016.
Amendment dated Jul. 13, 2017, U.S. Appl. No. 15/057,468, filed Mar. 1, 2016.

(56) References Cited

OTHER PUBLICATIONS

Notice of Allowance dated Sep. 19, 2017, U.S. Appl. No. 15/057,468, filed Mar. 1, 2016.
Amendment filed Mar. 19, 2018, U.S. Appl. No. 13/836769, filed Mar. 15, 2013.
Office Action dated Oct. 19, 2017, U.S. Appl. No. 13/836,769, filed Mar. 15, 2013.
Claims of U.S. Appl. No. 15/057468, filed Jul. 8, 2016.
Office Action dated Apr. 1, 2015, U.S. Appl. No. 13/836,769, filed Mar. 15, 2013.
Final Office Action dated Oct. 28, 2015, U.S. Appl. No. 13/836,769, filed Mar. 15, 2011.
Advisory Action dated Jan. 21, 2016, U.S. Appl. No. 13/836,769, filed Mar. 15, 2013.
Office Action dated Feb. 18, 2016, U.S. Appl. No. 13/836,769, filed Mar. 15, 2013.
Final Office Action dated Jun. 15, 2016, U.S. Appl. No. 13/836,769, filed Mar. 15, 2011.
Notice of Allowance dated Dec. 30, 2016, U.S. Appl. No. 13/836,769, filed Mar. 15, 2013.
Notice of Allowance dated Aug. 18, 2016, U.S. Appl. No. 13/836,769, filed Mar. 15, 2013.
Communication from the Examining Division dated Jun. 29, 2017, Application No. EP12816583.4.
Response After Final Action dated Aug. 12, 2016, U.S. Appl. No. 13/836,769, filed Mar. 15, 2013.
Amendment dated Jun. 6, 2016. U.S. Appl. No. 13/836,769, filed Mar. 15, 2013.
Amendment dated Jul. 31, 2015, U.S. Appl. No. 13/836,769, filed Mar. 15, 2013.
Preliminary Amendment dated Nov. 18, 2016, U.S. Appl. No. 13/836,769, filed Mar. 15, 2013.
Office Action dated Mar. 4, 2016, U.S. Appl. No. 13/690,075, filed Nov. 30, 2012.
Office Action dated Jul. 15, 2015, U.S. Appl. No. 13/690,075, filed Nov. 30, 2012.
Final Office Action dated Oct. 18, 2016, U.S. Appl. No. 13/690,075, filed Nov. 30, 2012.
Final Office Action dated Jan. 13, 2016, U.S. Appl. No. 13/690,075, filed Nov. 30, 2012.
Notice of Allowance dated Feb. 8, 2017, U.S. Appl. No. 13/690,075, filed Nov. 30, 2012.
Final Office Action dated Mar. 19, 2018, U.S. Appl. No. 13/690,075, filed Nov. 30, 2012.
Amendment dated Dec. 21, 2017, U.S. Appl. No. 13/690,075, filed Nov. 30, 2012.
Office Action dated Aug. 21, 2017, U.S. Appl. No. 13/690,075, filed Nov. 30, 2012.
Response to Restriction dated Oct. 28, 2014, U.S. Appl. No. 13/690,075, filed Nov. 30, 2012.
Restriction Requirement dated Oct. 20, 2014, U.S. Appl. No. 13/690,075, filed Nov. 30, 2012.
Amendment dated Jan. 27, 2017 U.S. Appl. No. 13/690,075, filed Nov. 30, 2012.
Preliminary Amendment dated Aug. 14, 2013, U.S. Appl. No. 13/690,075, filed Nov. 30, 2012.
Amendment dated Jun. 15, 2016, U.S. Appl. No. 13/690,075, filed Nov. 30, 2012.
Amendment dated Oct. 5, 2015, U.S. Appl. No. 13/690,075, filed Nov. 30, 2012.
RCE Amendment dated Apr. 12, 2017, U.S. Appl. No. 13/690,075, filed Nov. 30, 2012.
Amendment After Notice of Allowance dated Mar. 16, 2017, U.S. Appl. No. 13/690,075, filed Nov. 30, 2012.
Notice of Allowance dated May 5, 2017, U.S. Appl. No. 13/690,075, filed Nov. 30, 2012.
Notice of Allowance dated Mar. 21, 2016, U.S. Appl. No. 13/690,031, filed Nov. 30, 2012.
Amendment dated Aug. 25, 2016, U.S. Appl. No. 13/690,031, filed Nov. 30, 2012.
Amendment dated May 11, 2016, U.S. Appl. No. 13/690,031, filed Nov. 30, 2012.
Preliminary Amendment dated Aug. 14, 2013, U.S. Appl. No. 13/690,031, filed Nov. 30, 2012.
Preliminary Amendment dated Apr. 29, 2013, U.S. Appl. No. 13/690,031, filed Nov. 30, 2012.
Amendment dated Aug. 23, 2016, U.S. Appl. No. 13/690,031, filed Nov. 30, 2012.
Amendment dated Oct. 5, 2015, U.S. Appl. No. 13/690,031, filed Nov. 30, 2012.
Notice of Allowance dated Sep. 3, 2013, U.S. Appl. No. 10/583,176, filed Mar. 5, 2008.
Amendment dated Jul. 11, 2013, U.S. Appl. No. 10/583,176, filed Mar. 5, 2008.
Non-Final Rejection dated Jan. 16, 2013, U.S. Appl. No. 10/583,176, filed Mar. 5, 2008.
Amendment dated Oct. 1, 2012, U.S. Appl. No. 10/583,176, filed Mar. 5, 2008.
Non-Final Rejection dated May 1, 2012, U.S. Appl. No. 10/583,176, filed Mar. 5, 2008.
Amendment dated Apr. 5, 2012, U.S. Appl. No. 10/583,176, filed Mar. 5, 2008.
Final Rejection dated Nov. 17, 2011, U.S. Appl. No. 10/583,176, filed Mar. 5, 2008.
Amendment dated Aug. 22, 2011, U.S. Appl. No. 10/583,176, filed Mar. 5, 2008.
Non-Final Rejection dated May 20, 2011, U.S. Appl. No. 10/583,176, filed Mar. 5, 2008.
Notice of Allowance dated Jan. 26, 2011, U.S. Appl. No. 10/583,209, filed Oct. 18, 2007.
Amendment dated Jan. 26, 2011, U.S. Appl. No. 10/583,209, filed Oct. 18, 2007.
Amendment dated Dec. 20, 2010, U.S. Appl. No. 10/583,209, filed Oct. 18, 2007.
Final Rejection dated Oct. 19, 2010, U.S. Appl. No. 10/583,209, filed Oct. 18, 2007.
Amendment dated Jun. 16, 2010, U.S. Appl. No. 10/583,209, filed Oct. 18, 2007.
Non-Final Rejection dated Mar. 16, 2010, U.S. Appl. No. 10/583,209, filed Oct. 18, 2007.
Non-Final Rejection dated Feb. 3, 2011, U.S. Appl. No. 11/256,275, filed Oct. 21, 2005.
Amendment dated Apr. 20, 2010, U.S. Appl. No. 11/256,275, filed Oct. 21, 2005.
Final Rejection dated Feb. 3, 2010, U.S. Appl. No. 11/256,275, filed Oct. 21, 2005.
Amendment dated Sep. 9, 2009, U.S. Appl. No. 11/256,275, filed Oct. 21, 2005.
Non-Final Rejection dated Jun. 9, 2009, U.S. Appl. No. 11/256,275, filed Oct. 21, 2005.
Amendment dated Apr. 3, 2009, U.S. Appl. No. 11/256,275, filed Oct. 21, 2005.
Final Rejection dated Jan. 6, 2009, U.S. Appl. No. 11/256,275, filed Oct. 21, 2005.
Amendment dated Oct. 8, 2008, U.S. Appl. No. 11/256,275, filed Oct. 21, 2005.
Non-Final Rejection dated Jun. 9, 2008, U.S. Appl. No. 11/256,275, filed Oct. 21, 2005.
Response to Restriction dated May 14, 2008, U.S. Appl. No. 11/256,275, filed Oct. 21, 2005.
Restriction Requirement dated Feb. 5, 2008, U.S. Appl. No. 11/256,275, filed Oct. 21, 2005.
Notice of Allowance dated May 11, 2016, U.S. Appl. No. 14/498,735, filed Sep. 26, 2014.
Amendment dated Dec. 31, 2015, U.S. Appl. No. 14/498,735, filed Sep. 26, 2014.
Non-Final Rejection dated Sep. 15, 2015, U.S. Appl. No. 14/498,735, filed Sep. 26, 2014.
Preliminary Amendment dated Sep. 26, 2014, U.S. Appl. No. 14/498,735, filed Sep. 26, 2014.
Notice of Allowance dated Mar. 14, 2014, U.S. Appl. No. 10/583,175, filed Nov. 1, 2007.

(56) References Cited

OTHER PUBLICATIONS

Amendment dated Feb. 11, 2014, U.S. Appl. No. 10/583,175, filed Nov. 1, 2007.
Non-Final Rejection dated Nov. 22, 2013, U.S. Appl. No. 10/583,175, filed Nov. 1, 2007.
Advisory Action dated Oct. 10, 2013, U.S. Appl. No. 10/583,175, filed Nov. 1, 2007.
Amendment dated Sep. 27, 2013, U.S. Appl. No. 10/583,175, filed Nov. 1, 2007.
Final Rejection dated Jul. 29, 2013, U.S. Appl. No. 10/583,175, filed Nov. 1, 2007.
Amendment dated Jun. 14, 2013, U.S. Appl. No. 10/583,175, filed Nov. 1, 2007.
Non-Final Rejection dated Feb. 28, 2013, U.S. Appl. No. 10/583,175, filed Nov. 1, 2007.
Amendment dated Jul. 29, 2010, U.S. Appl. No. 10/583,175, filed Nov. 1, 2007.
Final Rejection dated Apr. 29, 2010, U.S. Appl. No. 10/583,175, filed Nov. 1, 2007.
Amendment dated Jan. 4, 2010, U.S. Appl. No. 10/583,175, filed Nov. 1, 2007.
Non-Final Rejection dated Oct. 2, 2009, U.S. Appl. No. 10/583,175, filed Nov. 1, 2007.
Notice of Allowance dated Jun. 26, 2014, U.S. Appl. No. 13/965,667, filed Aug. 13, 2013.
Response dated May 28, 2014, U.S. Appl. No. 13/965,667, filed Aug. 13, 2011.
Final Rejection dated Feb. 28, 2014, U.S. Appl. No. 13/965,667, filed Aug. 13, 2013.
Amendment dated Feb. 5, 2014, U.S. Appl. No. 13/965,667, filed Aug. 13, 2013.
Non-Final Rejection, dated Nov. 5, 2013, U.S. Appl. No. 13/965,667, filed Aug. 13, 2013.
Final Rejection dated Nov. 16, 2017, U.S. Appl. No. 14/069,021, filed Oct. 31, 2013.
Non-Final Rejection dated Mar. 9, 2017, U.S. Appl. No. 14/069,021, filed Oct. 31, 2013.
Final Rejection dated Dec. 2, 2015, U.S. Appl. No. 14/069,021, filed Oct. 31, 2013.
Amendment dated Sep. 23, 2015, U.S. Appl. No. 14/069,021, filed Oct. 31, 2013.
Non-Final Action dated Mar. 23, 2015, U.S. Appl. No. 14/069,021, filed Oct. 31, 2013.
Amendment dated Jan. 21, 2015, U.S. Appl. No. 14/069,021, filed Oct. 31, 2013.
Amendment dated May 17, 2017, U.S. Appl. No. 14/069,021, filed Oct. 31, 2013.
Non-Final Rejection dated Oct. 21, 2014, U.S. Appl. No. 14/069,021, filed Oct. 31, 2013.
Notice of Allowance dated May 9, 2013, U.S. Appl. No. 13/103,783, filed May 9, 2011.
Amendment dated May 9, 2013, U.S. Appl. No. 13/103,783, filed May 9, 2011.
Response dated May 2, 2013, U.S. Appl. No. 13/103,783, filed May 9, 2011.
Final Rejection dated Feb. 1, 2013, U.S. Appl. No. 13/103,783, filed May 9, 2011.
Amendment dated Feb. 28, 2012, U.S. Appl. No. 13/103,783, filed May 9, 2011.
Non-Final Rejection dated Nov. 28, 2011, U.S. Appl. No. 13/103,783, filed May 9, 2011.
Preliminary Amendment dated Jun. 8, 2011, U.S. Appl. No. 13/103,783, filed May 9, 2011.
Non-Final Rejection dated Nov. 1, 2016, U.S. Appl. No. 14/310,841, filed Jun. 20, 2014.
Amendment dated Sep. 27, 2016, U.S. Appl. No. 14/310,841, filed Jun. 20, 2014.
Final Rejection dated Jul. 7, 2016, U.S. Appl. No. 14/310,841, filed Jun. 20, 2014.
Amendment dated May 25, 2016, U.S. Appl. No. 14/310,841, filed Jun. 20, 2014.
Non-Final Rejection dated Feb. 8, 2016, U.S. Appl. No. 14/310,841, filed Jun. 20, 2014.
Response, dated Jan. 11, 2016 U.S. Appl. No. 14/310,841, filed Jun. 20, 2014.
Requirement for Restriction/Election dated Nov. 9, 2015, U.S. Appl. No. 14/310,841, filed Jun. 20, 2014.
International Search Report and Written Opinion from International Application No. PCT/US2004/042376, dated Mar, 24, 2005.
International Preliminary Report on Patentability from International Application No. PCT/US2004/042376, dated Jun. 20, 2006.
International Search Report and Written Opinion from International Application No. PCT/US2004/042792, dated Jul. 20, 2005.
International Preliminary Report on Patentability from International Application No. PCT/US2004/042792, dated Jun. 20, 2006.
International Search Report and Written Opinion from International Application No. PCT/US2004/012421, dated Sep. 13, 2004.
International Preliminary Report on Patentability from International Application No. PCT/US2004/012421, dated Oct. 28, 2005.
International Search Report and Written Opinion from International Application No. PCT/US2004/042377, dated Jun. 20, 2006.
International Preliminary Report of Patentability dated Jun. 20, 2006, from International Application No. PCT/US2004/042377, dated Jun. 20, 2006.
International Preliminary Examination Report, dated Nov. 12, 2004, International Application No. PCT/US03/28463, International Filing Date Sep. 9, 2003.
Amendment filed Mar. 13, 2018, U.S. Appl. No. 15/245,450, filed Aug. 24, 2016.
Non-Final Office Action dated Dec. 15, 2017, U.S. Appl. No. 15/245,450, filed Aug. 24, 2016.
Final Rejection dated Jan. 11, 2018, U.S. Appl. No. 12/139,359, filed Jun. 13, 2008.
Advisory Action dated Apr. 27, 2018, U.S. Appl. No. 12/139,359, filed Jun. 13, 2008.
Amendment dated Apr. 11, 2018, U.S. Appl. No. 12/139,359, filed Jun. 13, 2008.
Amendment dated Dec. 14, 2017, U.S. Appl. No. 12/139,359, filed Jun. 13, 2008.
Non-Final Rejection dated Jun. 14, 2017, U.S. Appl. No. 12/139,359, filed Jun. 13, 2008.
Amendment dated Apr. 19, 2017, U.S. Appl. No. 12/139,359, filed Jun. 13, 2008.
Advisory Action dated Mar. 31, 2017, U.S. Appl. No. 12/139,359, filed Jun. 13, 2008.
Amendment After Final dated Mar. 31, 2017, U.S. Appl. No. 12/139,359, filed Jun. 13, 2008.
Response After Final Action dated Mar. 23, 2017, U.S. Appl. No. 12/139,359, filed Jun. 13, 2008.
Final Rejection dated Nov. 23, 2016, U.S. Appl. No. 12/139,359, filed Jun. 13, 2008.
Amendment dated Sep. 14, 2016, U.S. Appl. No. 12/139,359, filed Jun. 13, 2008.
Non-Final Rejection dated Jun. 15, 2016, U.S. Appl. No. 12/139,359, filed Jun. 13, 2008.
Amendment dated Mar. 15, 2016, U.S. Appl. No. 12/139,359, filed Jun. 13, 2008.
Final Office Action dated Mar. 24, 2014, U.S. Appl. No. 13/690,094, filed Nov. 30, 2012.
Final Office Action dated Mar. 3, 2015, U.S. Appl. No. 13/690,094, filed Nov. 30, 2012.
Office Action dated Sep. 26, 2013, U.S. Appl. No. 13/690,094, filed Nov. 30, 2012.
Office Action dated Sep. 24, 2014, U.S. Appl. No. 13/690,094, filed Nov. 30, 2012.
Office Action dated Jul. 14, 2015, U.S. Appl. No. 13/690,094, filed Nov. 30, 2012.
Notice of Allowance dated Feb. 18, 2016, U.S. Appl. No. 13/690,094, filed Nov. 30, 2012.
Notice of Allowance dated Nov. 9, 2015, U.S. Appl. No. 13/690,094, filed Nov. 30, 2012.

(56) References Cited

OTHER PUBLICATIONS

Advisory Action dated May 12, 2015, U.S. Appl. No. 13/690,094, filed Nov. 30, 2012.
Amendment dated Feb. 18, 2016, U.S. Appl. No. 13/690,094, filed Nov. 30, 2012.
Amendment dated May 12, 2015, U.S. Appl. No. 13/690,094, filed Nov. 30, 2012.
Amendment dated Jun. 2, 2015, U.S. Appl. No. 13/690,094, filed Nov. 30, 2012.
Preliminary Amendment dated Aug. 14, 2013, U.S. Appl. No. 13/690,094, filed Nov. 30, 2012.
Response dated Apr. 29, 2015, U.S. Appl. No. 13/690,094, filed Nov. 30, 2012.
Amendment dated Feb. 5, 2016, U.S. Appl. No. 13/690,094, filed Nov. 30, 2012.
Amendment dated Oct. 14, 2015, U.S. Appl. No. 13/690,094, filed Nov. 30, 2012.
Amendment dated Jan. 19, 2015, U.S. Appl. No. 13/690,094, filed Nov. 30, 2012.
Amendment dated Dec. 18, 2013, U.S. Appl. No. 13/690,094, filed Nov. 30, 2012.
Final Office Action dated Jan. 14, 2016, U.S. Appl. No. 13/690,056, filed Nov. 30, 2012.
Office Action dated Aug. 10, 2015, U.S. Appl. No. 13/690,056, filed Nov. 30, 2012.
Office Action dated Mar. 7, 2016, U.S. Appl. No. 13/690,056, filed Nov. 30, 2012.
Office Action dated Sep. 1, 2016, U.S. Appl. No. 13/690,056, filed Nov. 30, 2012.
Office Action dated Nov. 15, 2016, U.S. Appl. No. 13/690,056, filed Nov. 30, 2012.
Office Action dated Mar. 7, 2017, U.S. Appl. No. 13/690,056, filed Nov. 30, 2012.
Notice of Allowance dated Jun. 14, 2017, U.S. Appl. No. 13/690,056, filed Nov. 30, 2012.
Notice of Allowance dated Jan. 19, 2018, U.S. Appl. No. 13/690,056, filed Nov. 30, 2012.
Amendment dated Oct. 28, 2016, U.S. Appl. No. 13/690,056, filed Nov. 30, 2012.
Amendment dated Jun. 6, 2016, U.S. Appl. No. 13/690,056, filed Nov. 30, 2012.
Amendment dated Oct. 5, 2015, U.S. Appl. No. 13/690,056, filed Nov. 30, 2012.
Preliminary Amendment dated Aug. 14, 2013, U.S. Appl. No. 13/690,056, filed Nov. 30, 2012.
Amendment dated Mar. 15, 2017, U.S. Appl. No. 13/690,056, filed Nov. 30, 2012.
Amendment dated Nov. 28, 2016, U.S. Appl. No. 13/690,056, filed Nov. 30, 2012.
Notice of Allowance dated Jan. 31, 2018, U.S. Appl. No. 15/152,248, filed May 11, 2016.
Response dated Oct. 12, 2017, U.S. Appl. No. 15/152,248, filed May 11, 2016.
Final Office Action dated May 12, 2017, U.S. Appl. No. 15/152,248, filed May 11, 2016.
Office Action dated Nov. 23, 2016, U.S. Appl. No. 15/152,248, filed May 11, 2016.
Preliminary Amendment dated Jan. 9, 2017, U.S. Appl. No. 15/152,248, filed May 11, 2016.
Preliminary Amendment dated Oct. 28, 2016, U.S. Appl. No. 15/152,248, filed May 11, 2016.
Amendment dated Mar. 23, 2017, U.S. Appl. No. 15/152,248, filed May 11, 2016.
Office Action dated Aug. 18, 2014, U.S. Appl. No. 29/452,640, filed Apr. 19, 2013.
Notice of Allowance dated Nov. 19, 2014, U.S. Appl. No. 29/452,640, filed Apr. 19, 2013.
Amendment dated Nov. 3, 2014, U.S. Appl. No. 29/452,640, filed Apr. 19, 2013.
Amendment dated Oct. 1, 2014, U.S. Appl. No. 29/452,640, filed Apr. 19, 2013.
Office Action dated Aug. 18, 2014, U.S. Appl. No. 29/440,594, filed Dec. 21, 2012.
Notice of Allowance dated Nov. 28, 2014, U.S. Appl. No. 29/440,594, filed Dec. 21, 2012.
Response dated Aug. 7, 2014, U.S. Appl. No. 29/440,594, filed Dec. 21, 2012.
Amendment dated Nov. 3, 2014, U.S. Appl. No. 29/440,594, filed Dec. 21, 2012.
Amendment dated Oct. 1, 2014, U.S. Appl. No. 29/440,594, filed Dec. 21, 2012.
Final Office Action dated Jan. 8, 2016, U.S. Appl. No. 13/690,031, filed Nov. 30, 2012.
Office Action dated Jul. 15, 2015, U.S. Appl. No. 13/690,031, filed Nov. 30, 2012.
Notice of Allowance dated Jun. 7, 2016, U.S. Appl. No. 13/690,031, filed Nov. 30, 2012.
Int'l Search Report and Written Opinion, PCT/US2012/071436, dated Apr. 10, 2013, 13 pages.
Int'l Search Report and Written Opinion, PCT/US2012/071461, dated Apr. 4, 2013, 14 pages.
Int'l Search Report and Written Opinion, PCT/US2012/071488, dated Feb. 8, 2013, 11 pages.
Int'l Search Report and Written Opinion, PCT/US2012/071450, dated May 24, 2013, 10 pages.
U.S. Appl. No. 60/464,860, filed Apr. 22, 2003, Christopher Pearce et al., 7 pages.
U.S. Appl. No. 60/530,151, filed Dec. 17, 2003, Christopher Pearce et al., 125 pages.
Office Action dated Jun. 14, 2018, U.S. Appl. No. 14/069,021, filed Oct. 31, 2013.
Notice of Allowance dated Jul. 13, 2018, U.S. Appl. No. 13/690,075, filed Nov. 30, 2012.
Notice of Allowance dated Jul. 13, 2018, U.S. Appl. No. 15/152,248, filed May 11, 2016.
Notice of Allowance dated Aug. 15, 2018, U.S. Appl. No. 15/245,450, filed Aug. 24, 2016.
Response to Final Office Action dated Jul. 27, 2018, U.S. Appl. No. 15/245,450, filed Aug. 24, 2016.
Final Office Action dated Jul. 13, 2018, U.S. Appl. No. 15/245,450, filed Aug. 24, 2016.
Amendment filed Aug. 23, 2018, U.S. Appl. No. 13/836,769, filed Mar. 15, 2013.

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

UTILITY MODULE SYSTEM

CROSS REFERENCE TO RELATED PATENT APPLICATIONS

This patent application is a divisional of and claims priority to U.S. patent application Ser. No. 13/690,031, filed Nov. 30, 2012, now U.S. Pat. No. 9,457,197, which is hereby incorporated by reference in its entirety. U.S. patent application Ser. No. 13/690,031 is a non-provisional of the following U.S. provisional applications, each of which was filed on May 8, 2012, and each of which is hereby incorporated in its entirety: U.S. Prov. Appl. 61/644,303; U.S. Prov. Appl. 61/644,308; U.S. Prov. Appl. 61/644,314; and U.S. Prov. Appl. 61/644,321.

This patent application may be found to be related to the following U.S. patent applications: application Ser. No. 13/690,094, entitled "Defibrillator Network System," filed Nov. 30, 2012 in the name of David Aoyama et al., now U.S. Pat. No. 9,289,621 (issued Mar. 22, 2016); application Ser. No. 13/690,056, entitled "Utility Module," filed Nov. 30, 2012, in the name of Barry Curtin et al.; and U.S. patent application Ser. No. 13/690,075, entitled "Utility Module Interface", also filed Nov. 30, 2012, in the name of David Aoyama et al.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

Advanced medical devices may be used to assist the CPR process by coaching a rescuer who performs CPR. For example, a medical device can issue instructions, and even prompts, for the rescuer to perform CPR more effectively.

While some advanced medical devices provide coaching, defibrillator operators may benefit from additional coaching.

BRIEF SUMMARY

The present description gives instances of devices, systems, software and methods, the use of which may help overcome problems and limitations of the prior art.

A defibrillator system is system is disclosed for enabling communications between a defibrillator and a utility module. The defibrillator may include an energy storage device for storing an electrical charge; a defibrillation port; a display; a defibrillator processor configured to control the display and when an electrical charge is applied to the defibrillation port for defibrillating a patient; a defibrillator data connect port. The utility module may include a parameter module configured to detect a parameter of a patient; a data outlet configured to engage the defibrillator data connect port of the defibrillator for transmitting data to or receiving data from the defibrillator; and a module processor configured to control the parameter module.

In an alternative embodiment, the utility module may include a communication module configured to transmit data from the first utility module; a data outlet configured to engage a defibrillator data connect port of the defibrillator for transmitting data to or receiving data from the defibrillator; and a module processor configured to control the communication module.

An illustrative method for providing coaching information to a defibrillator may include: providing a utility module with a patient parameter module and a communication module configured to transmit data from the utility module and a module processor configured to control the patient parameter module and the communication module; connecting the utility module to a defibrillator including an energy storage device for storing an electrical charge, a defibrillation port, a display, and a defibrillator processor configured to control the display and when an electrical charge is applied to the defibrillation port for a defibrillating of a patient; and providing coaching data from the utility module to the defibrillator for use in the defibrillating of the patient.

These and other features and advantages of this description will become more readily apparent from the following Detailed Description, which proceeds with reference to the drawings, in which:

BRIEF DESCRIPTION OF THE DRAWINGS

FIG. 1 is an illustrative diagram of a scene showing the use of an external defibrillator to save the life of a person according to this disclosure.

FIG. 2 is a table listing two illustrative types of the external defibrillator shown in FIG. 1, and who they might be used by.

FIGS. 28A, B are collectively referred to herein as FIG. 28.

DETAILED DESCRIPTION

Figures 1, 2:
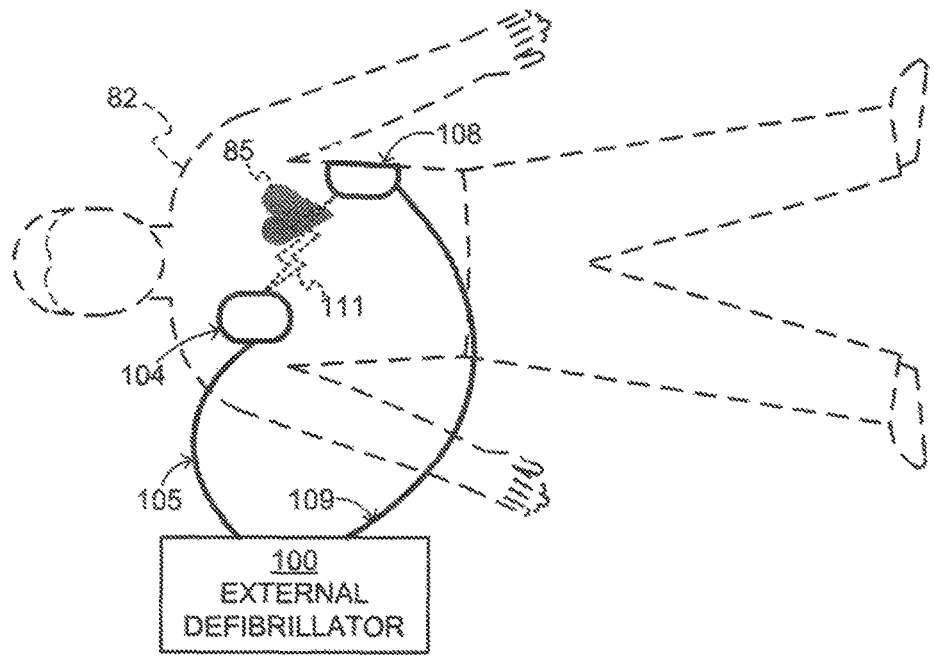

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
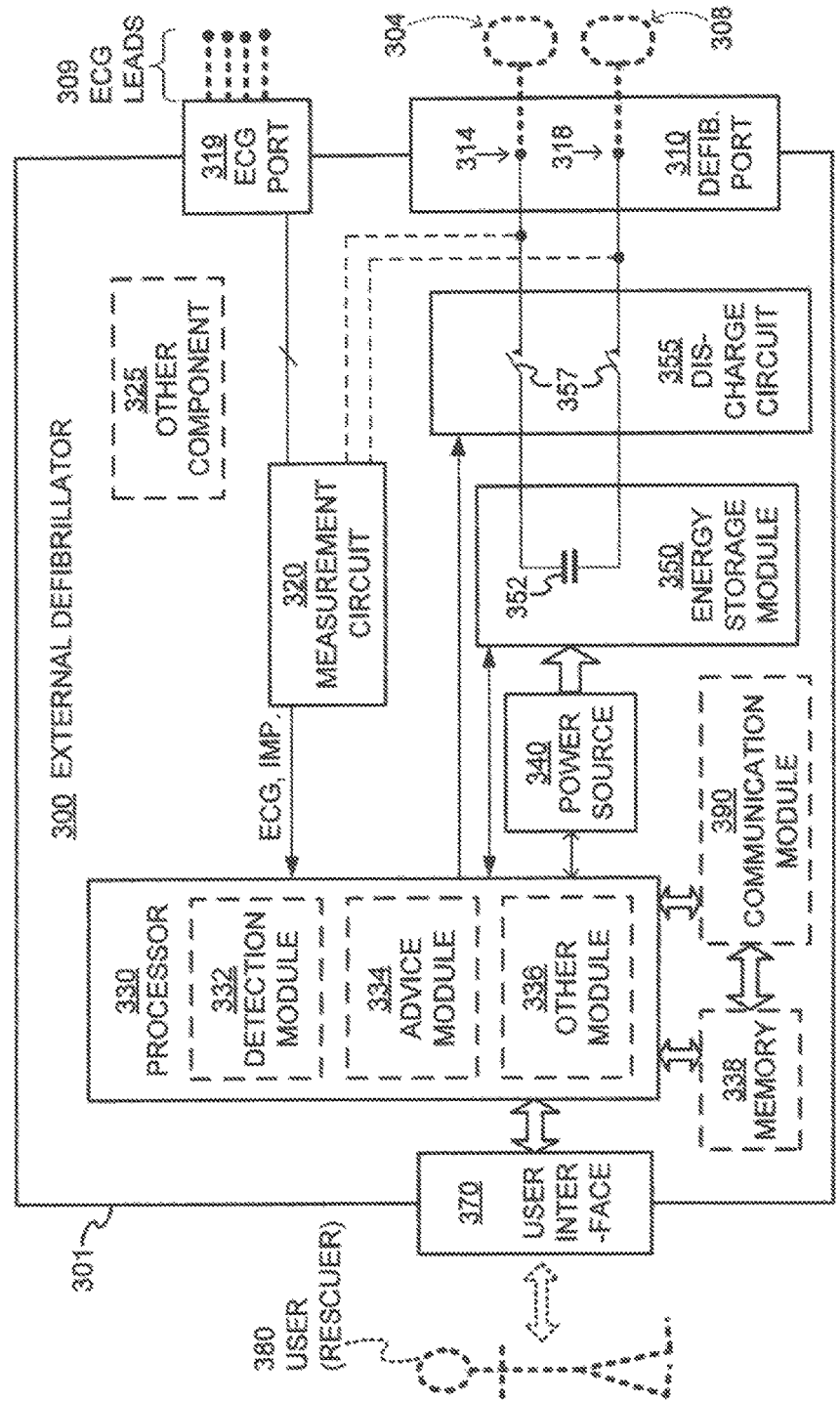
FIG. 3 is a diagram showing components of an external defibrillator, such as the one shown in FIG. 1, configured in an illustrative embodiment according to this disclosure.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Having thus introduced background on the general operation of a defibrillator, we now turn to features that are provided by this disclosure.

Figure 4:
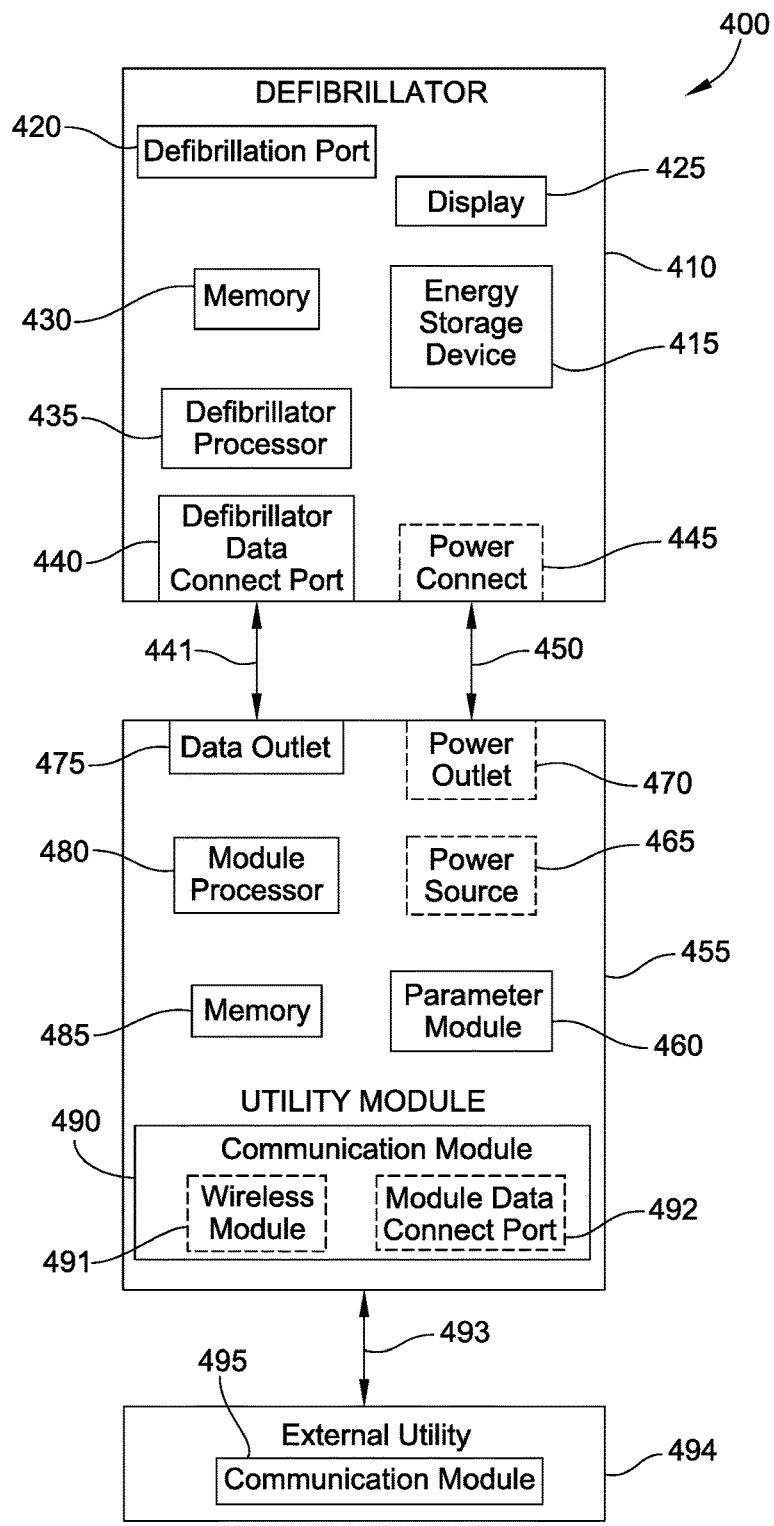
FIG. 4 shows a functional diagram of an illustrative defibrillator system of this disclosure.

FIG. 4 shows a functional diagram of a defibrillator system 400 comprising: a defibrillator 410 and a utility module 455. Defibrillator 410 comprises an energy storage device 415 for storing an electrical charge; a defibrillation port 420; a display 425; a defibrillator processor 435 configured to control the display 425 and when an electrical charge is applied to the defibrillation port 420 for defibrillating a patient; a memory 430; and a defibrillator data connect port 440. Defibrillator 410, and its various components, can be as already described with reference to FIG. 3 above.

Utility module 455 in FIG. 4 illustratively comprises a parameter module 460 configured to detect a parameter of a patient; a communication module 490 configured to transmit data from the utility module; a data outlet 475 configured to engage the defibrillator data connect port 440 of the defibrillator 410 for transmitting data to or receiving data from the defibrillator 410; and a module processor 480 configured to control the parameter module 460 and the communication module 490 and a memory 485. While the illustrative embodiment includes both the parameter module 460 and the communication module 490, it will be appreciated that other embodiments may include the parameter module without the communication module; or may include the communication module without the parameter module. In other words, each of the parameter module and the communication module may be used alone or in combination with the other module or still other modules in the disclosed utility module.

In an alternative embodiment, the defibrillator 410 may further include a power connect 445 and the utility module may further include a power outlet 470 configured to engage the power connect 445 of the defibrillator 410 for providing an electrical charge to the defibrillator 410 from a power source 465. In another alternative embodiment, the utility module is further provided with the power source 465.

The display 425 of the defibrillator 410 may be a visual display capable of displaying data transmitted from defibrillator processor 435. Displays for use with this disclosure may include an LCD screen, an e-paper display, or other bi-stable display, a CRT display or any other type of visual display.

The defibrillator data connect port 440 may illustratively be a hardware based data connector configured to connect with the data outlet 475 of the utility module as described below. Alternatively, the defibrillator data connect port 440 may be one or more ports that allow bidirectional flow of data between the defibrillator and the utility module. Illustratively, the defibrillator data connect port is an RS232 socket connector configured for connection to the data outlet 475 in a wired connection. Illustratively, the RS232 socket connector may connect with an RS232 plug connector forming the data outlet 475. Alternatively, the data outlet 475 may also be a socket connector and the RS232 socket connector of the defibrillator data connect port may be adapted to connect to the socket connector of the data outlet, such as through a cable terminating on either end with a plug connector. As another example, each of the defibrillator data connect port and the data outlet may be plug connectors that are adapted to be connected through a cable terminating on either end with a socket connector. Other connectors may be used for defibrillator data connect port 440 as are well known in the art.

While the foregoing disclosure of the defibrillator data connect port is illustrative based on the RS232 standard, it will be appreciated that defibrillator data connect port may include a USB or other wire connector. In addition, the defibrillator data connect port may be a wireless connector for wireless connection with the data outlet 475. In addition, while the illustrative defibrillator data connect port is disclosed as hardware based, it will be appreciated that the hardware may be configurable by software in which case the hardware and software together may together form the defibrillator data connect port of this disclosure.

The power connect 445 of the defibrillator may illustratively be a hardware based power connector configured to connect with the power outlet 470 of the utility module as described below. Alternatively, the power connect may be one or more power connectors that allow power to flow between the defibrillator and the utility module. Illustratively, the power connect is a plug connector configured for connection to the power outlet 470 configured as a socket connector in a wired connection. Alternatively, the power connect 445 may also be a socket connector and the socket connector of the power connect may be adapted to connect to the socket connector of the power outlet through a cable terminating on either end with a plug connector. As another example, each of the power connect 445 of the defibrillator and the power outlet of the utility module may be plug connectors that are adapted to be connected through a cable terminating on either end with a socket connector. Other connectors may be used for power connect 445 as are well known in the art. In addition, while the power connect 445 is disclosed as hardware based, it will be appreciated that the hardware may be configurable by software in which case the hardware and software together may together form the power connect 445 of this disclosure.

Referring now to the components that may make up the utility module 455, the parameter module can be any monitor configured to detect a parameter of a patient. The patient parameter may include one or more of the following measurements: a measurement of $CO_2$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The patient parameter of the $CO_2$ exhaled by a patient may be measured using capnography techniques. The patient parameter of the electrical activity of the heart of a patient may be measured using ECG techniques. The patient parameter of the exchange of air between the lungs of a patient and the atmosphere may be measured using ventilation techniques. The patient parameter of the measurement of the pressure of the blood in a patient may be measured using non-invasive blood pressure measurement techniques or invasive blood pressure measurement techniques. The patient parameter of the temperature of a patient may be measured using temperature measurement techniques. The patient parameter of the oxygen saturation in the blood of a patient may be measured using pulse oximeter techniques or tissue oximetry techniques. The patient parameter of the chest compression of a patient may be measured using chest compression detection and feedback techniques. The patient parameter of the image of the internal structure of a patient may be measured using ultrasound measurement techniques. The patient parameter of the oxygen saturation in the blood in the brain of a patient may be measured using cerebral oximetry techniques. The patient parameter of the acidity or alkalinity of fluids in a patient may be measured using non-invasive pH measurement techniques. These and other techniques and modules for generating the foregoing and other kind of patient parameter data for use with this disclosure are well known in the art.

Data outlet 475 is configured to engage the defibrillator data connect port 440 of the defibrillator for transmitting data to or receiving data from the defibrillator. The data outlet 475 may be one or more ports that allow bidirectional flow of data between the utility module and the defibrillator. Illustratively, the data outlet 475 is an RS232 plug connector configured for connection to the illustrative socket connector of the defibrillator data connect port 440 as described above in a wired connection.

Alternatively, the data outlet 475 may also be a socket connector adapted to connect to the socket connector of the defibrillator through a cable terminating on either end with a plug connector. As another example, each of the data outlet 475 and the defibrillator data connect port 440 may be plug connectors that are adapted to be connected through a cable terminating on either end with a socket connector. Other connectors may be used for data outlet 475 as are well known in the art. In addition, the data outlet 475 may be a wireless connector for enabling a wireless connection with the defibrillator data connect port 440. While the data outlet is disclosed as hardware based, it will be appreciated that the hardware may be configurable by software in which case the hardware and software together may together form the data outlet of this disclosure. When the data outlet receives and engages the defibrillator data connect port, a data communication link 441 is established for the bidirectional flow of data between the utility module and the defibrillator.

Communication module 490 is hardware and software configured to transmit data from the utility module. Illustratively, the communication module 490 is configured to transmit data from the utility module to an external utility 494. The external utility 494 may be a computer, a laptop, a server, a mobile computing device, or other computing device. Alternatively, the utility module may transmit data over the communication module 490 to the defibrillator 410. The bidirectional transmission of data from out of and to the utility module through the communication module 490 may be separate from and additional to the bidirectional flow of data occurring through the data outlet 475 and the defibrillator data connect port 440 of the utility module and the defibrillator, respectively, over the data communication link 441 described above. Alternatively, the data outlet 475 and the defibrillator data connect port 440 may be functionality that is provided by the communication module 490.

As illustrated in FIG. 4, the external utility 494 is likewise provided with a communication module 495. Together, the communication module 490, 495 of the utility module 455 and the external 495, respectively, enable a communication link 493 to be established between the utility module and the external utility for enabling the bidirectional flow of data between the two devices.

In an illustrative embodiment, the communication module may comprise a wireless module 491 and/or a module data connect port 492 as shown in FIG. 4 and described in greater detail below. The wireless module may illustratively be a Wi-Fi module. Alternatively, the wireless module 491 may be a blue tooth module, a CDMA module, or any other communication module that enables a wireless communication link for the bidirectional flow of data between devices wirelessly. The module data connect port 492 may be a hardware based data connector configured to connect with a data outlet of the external utility 494 (not shown) as described later below. The module data connect port 492 may be one or more ports that allow bidirectional flow of data between the utility module and the external utility 494. Illustratively, the module data connect port is an RS232 plug connector configured for connection to a socket connector (not shown) of the external utility 494 in a wired connection. Alternatively, the module data connect port may also be a socket connector and the RS232 socket connector of the external utility may be adapted to connect to the socket connector of the utility module through a cable terminating on either end with a plug connector. As another example, each of the module data connect port and the connector of the external utility may be plug connectors that are adapted to be connected through a cable terminating on either end with a socket connector. Other connectors may be used for module data connect port 492 as are well known in the art.

While the foregoing disclosure of the module data connect port is illustrative based on the RS232 standard, it will be appreciated that module data connect port may include a USB or other wire connector. In addition, while the module data connect is disclosed as hardware based, it will be appreciated that the hardware may be configurable by software in which case the hardware and software together may together form the module data connect port of this disclosure.

The module processor 480 of the utility module can be any microprocessor capable of accessing information stored in memory 485, performing actions based on instructions using information from memory 485 or some other source, and alternatively storing information in memory 485 or transmitting information. An example of transmitting information can be sending information from parameter module 460 to the defibrillator or the external utility as discussed later in this disclosure. The module processor 480 may be configured to control the parameter module in an embodiment where a parameter module is included in the utility module. The module processor 480 may be configured to control the communication module in an embodiment where a communication module is included in the utility module. The module processor 480 may also be configured to control both the parameter module and the communication module an embodiment where both a parameter module and a communication module are included in the utility module. While FIG. 4 shows a module processor 480 as a single processor, it will be appreciated that more than one processor may also be used for module processor 480 in accordance with this disclosure.

Memory 485 of the utility module can be any form of data storage. It may be at least one of random access memory (RAM) and/or read only memory (ROM). Information can be stored permanently until overwritten and/or stored temporarily for use while the unit is active.

The power outlet 470 is illustratively configured to engage the power connect 445 of the defibrillator for providing an electrical charge 450 to the defibrillator from the power source 465. Alternatively, the power connect 445 of the defibrillator may also provide power from the energy storage device 415 of the defibrillator to the power source 465 of the utility module when the utility module is without sufficient power to operate as described later below. The power outlet 470 of the utility module may illustratively be a hardware-based power connector configured to connect with the power connect 445 of the defibrillator as described below. Alternatively, the power outlet may be one or more power connectors that allow power to flow between the utility module and the defibrillator. Illustratively, the power outlet 470 is a socket connector configured for connection to the power connect 445 of the defibrillator configured as a plug connector in a wired connection. Alternatively, the power outlet 470 may also be a plug connector and the plug connector of the power connect may be adapted to connect to the plug connector of the power outlet through a cable terminating on either end with a socket connector. As another example, each of the power outlet 470 and the power connect of the defibrillator may be socket connectors that are adapted to be connected through a cable terminating on either end with a plug connector. Other connectors may be used for power outlet 470 as are well known in the art. While the power outlet is disclosed as hardware based, it will be appreciated that the hardware may be configurable by software in which case the hardware and software may together form the power outlet of this disclosure. When the power outlet 470 receives and engages the power connect 445, a power link 450 is established for the bidirectional flow of power between the utility module and the defibrillator.

Power source 455 can be can be a battery or fuel cell, a direct line from a wall outlet, current from a solar cell or any other power source sufficient to satisfy the power requirements for utility module 450.

Figure 5:
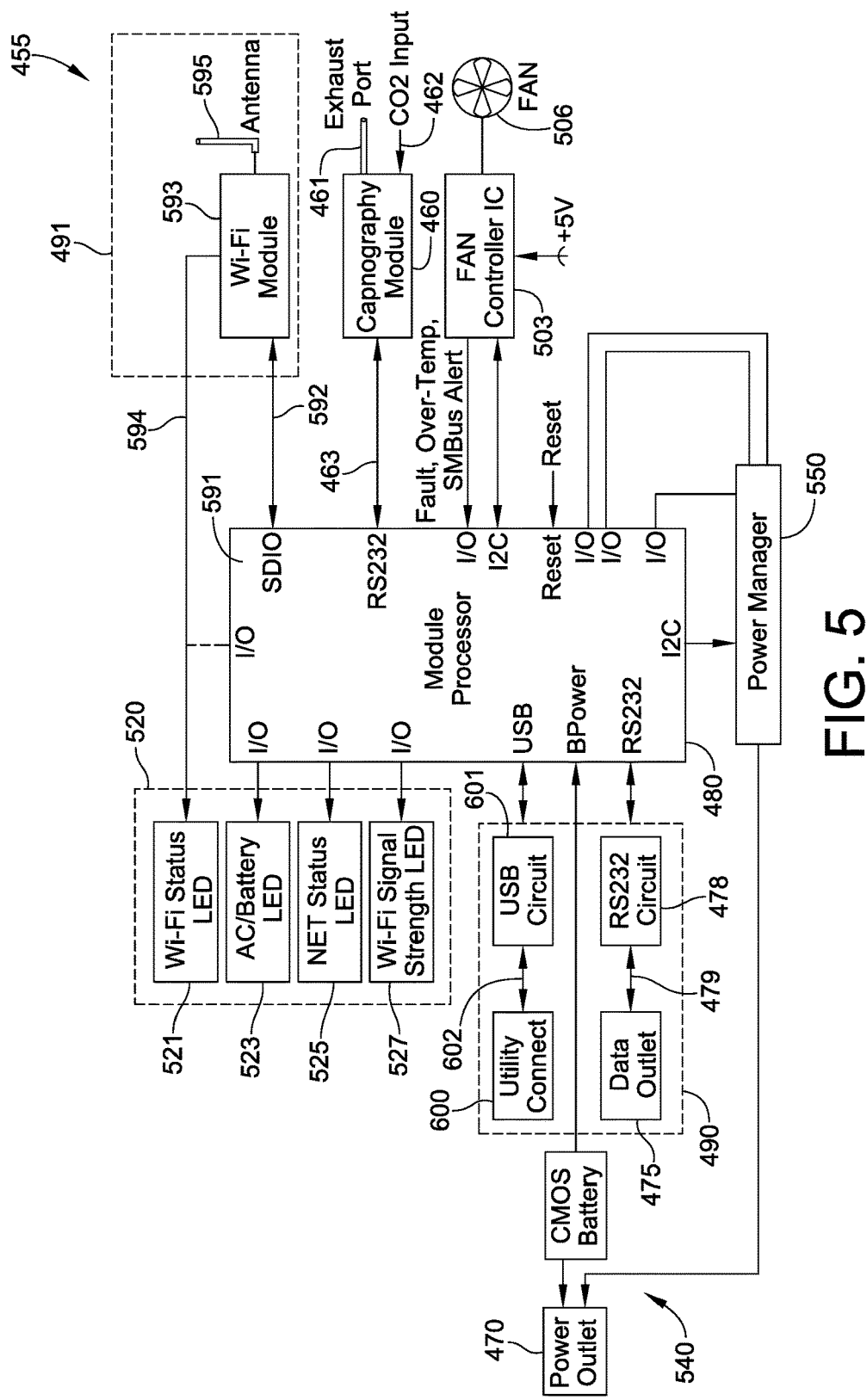
FIG. 5 shows an illustrative embodiment of the utility module of module shown in FIG. 4.

FIG. 5 shows an illustrative embodiment of the utility module 455 of FIG. 4. FIG. 5 shows the utility module 455 comprising the parameter module 460; the communication module 490; the power outlet 470; the data outlet 475 configured to engage the data connect 440 of the defibrillator 410 (shown in FIG. 4) for transmitting data to or receiving data from the defibrillator 410; and a module processor 480 configured to control the parameter module 460 and the communication module 490. These components in FIG. 5 are the same components as are shown in FIG. 4 bearing the same number, and the description and operation of these components in FIG. 5 are the same as the description and operation of these components in FIG. 4.

Figure 14:
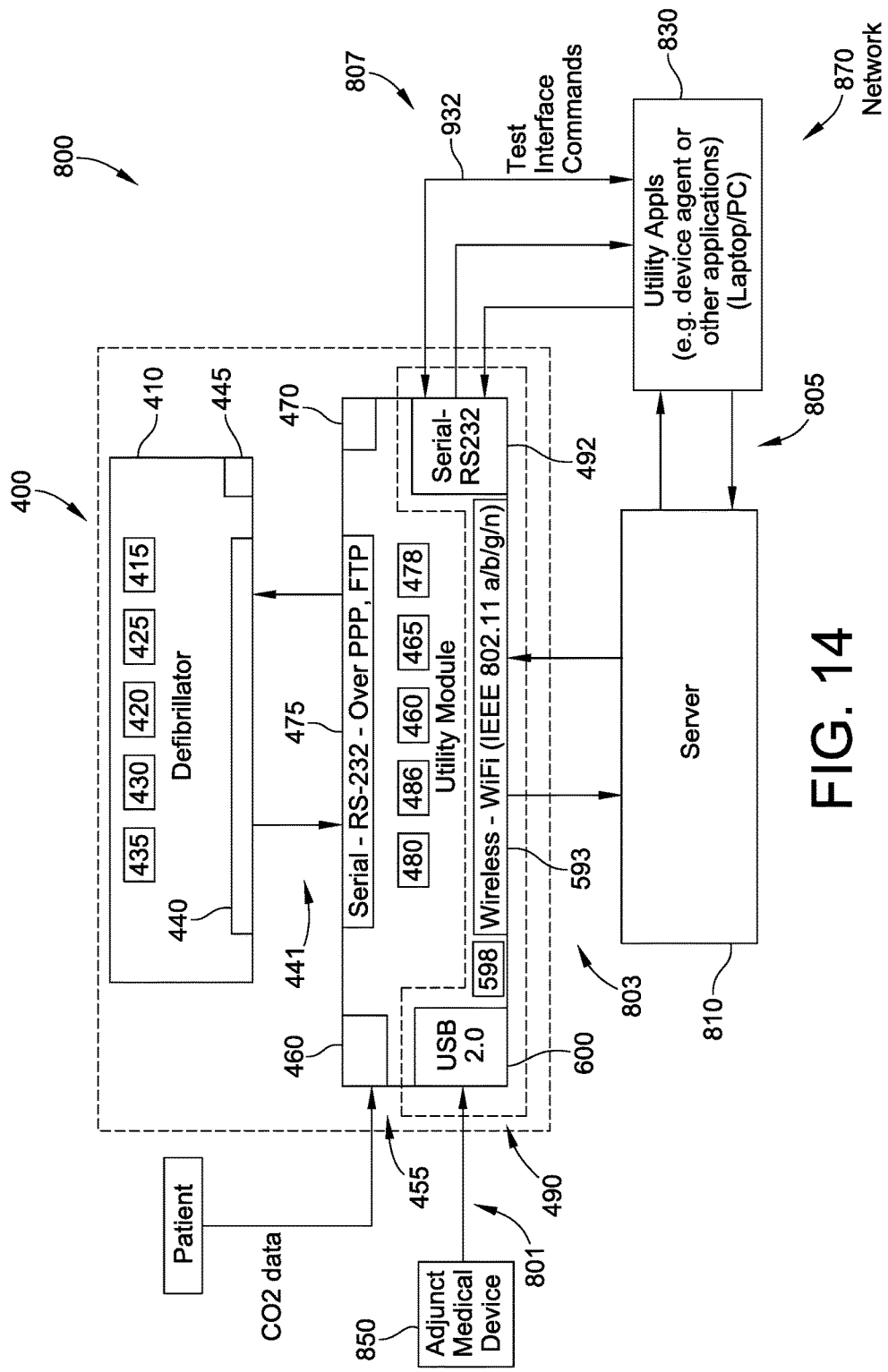
FIG. 14 shows an illustrative embodiment of another system of this disclosure employing the defibrillator system of FIG. 4 in a network.

In the illustrative embodiment, the module processor 480 controls the operation of all the modules that make up the utility module. Alternatively, the utility module may be provided with more than one processor for this purpose. As shown in FIG. 5, the module processor 480 may illustratively be a processor and associated chipset (not shown) that advantageously enables interfaces such as the Serial (UART), SDIO, and USB to be used for connecting the utility module to other components. For instance, the interfaces allow the processor to be connected to the defibrillator 410, the parameter module 460 (a CO2 module is shown in FIG. 5), a device agent (not shown but such as described in FIG. 14 illustratively through a data outlet 475 shown in FIG. 5 as described in FIG. 4), a Wi-Fi module 593 and external devices like an adjunct medical device (not shown but as described in FIG. 14 below illustratively through a utility connect 600 shown in FIG. 5). The module processor 480, which is also sometimes referred to as processor module, also enables other digital I/O interfaces such as to control LED status information on an indicator panel 520 and to power manager 550 of the utility module. Illustratively the module processor may be a CM-T3517 processor made by Compulab. Alternatively, any one or more processors that provide the functions that are within the scope of this disclosure may be used.

In the illustrative embodiment shown in FIG. 5, the parameter module 460 is a capnography module configured to detect CO2 of a patient. The capnography module measures the CO2, respiration rate and pulse rate of the patient. The patient breathes into a CO2 input 462 of the capnography module 460 with exhaust port 461 providing the exhaust port for this inhaled breath of air after analysis by the parameter module. The parameter module 460 digitizes the breath data of the patient and applies a stream of the digitized data over an RS232 communication link 463 for input to the module processor 480.

Figure 6:
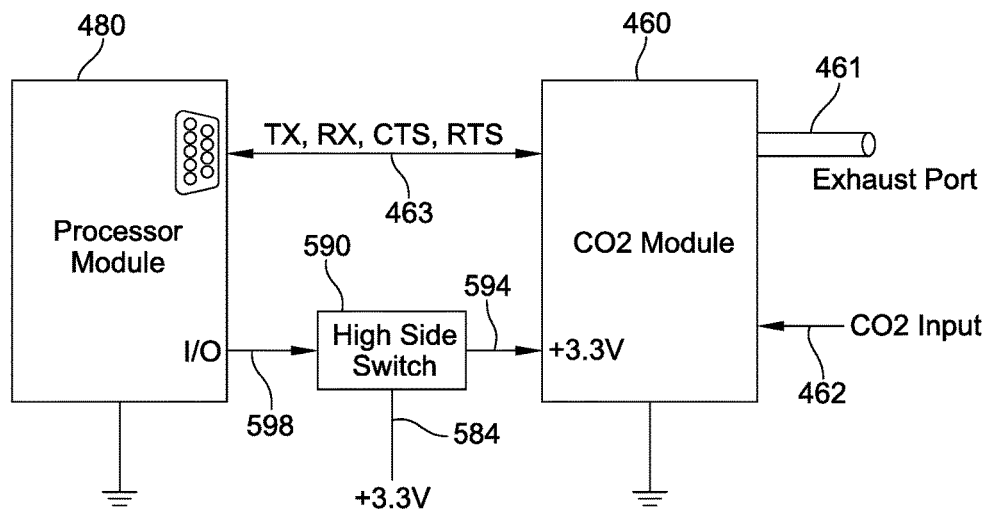
FIG. 6 is a enlarged view of the parameter module included in the utility module shown in FIG. 5.

FIG. 6 is an enlarged view of the parameter module 460 which also shows managed control of power to the parameter module 460 using a high side switch 593. High side switch 590 and its operation is described in greater detail in the description of the power manager 550 below. Generally speaking, high side switch 590 is controlled by the module processor 480 through a control signal applied by the module processor 480 to signal line 598. When the control signal is true, the high side switch 590 is turned on. This allows 3.3 volts of power on signal line 584 to be applied to signal line 594 and to the parameter module 460 causing parameter module to power on. Control of the parameter module 460 occurs through TX, RX, CTS, RTS signals that are applied by module processor 480 to RS232 communication link 463 using a serial UART interface. The RS232 communication link allows the module processor 480 to control the bidirectional transmission of data from the parameter module 460 throughout the utility module. Advantageously, this allows the utility module to make data from the parameter module available to the defibrillator and to other external devices as described in greater detail later below. Illustratively, the parameter module is a Micromedi-CO2 capnography module manufactured by Oridion. Alternatively, any module for monitoring patient parameter data may be used with this disclosure.

As previously discussed in connection with FIG. 4, the communication module 490 may illustratively comprise a wireless module 491 and a module data connect port 492. In the illustrative embodiment shown in FIG. 5, the wireless module 491 is a Wi-Fi module 593. In addition, the module data connect port 492 is shown in FIG. 5 illustratively comprising a USB circuit 601, and a USB connect 600. The USB circuit 601 and USB connect 600 and the Wi-Fi module 593 in the communication module 490 are illustratively configured to transmit data from the utility module 455. Specifically, Wi-Fi module 593 includes a radio transmitter and receiver and associated circuitry (not shown) for receiving and transmitting wireless data preferably according to the 802.11 Wi-Fi protocol. Alternatively, Wi-Fi module 593 may be configured to transmit and receive data by non-standardized protocols. In an alternative embodiment, another communication module may be used in place of the Wi-Fi module 593 and configured to receive and transmit wireless data according to other communication protocols, such as blue-tooth, CDMA, etc. Alternatively, the other wireless modules may be included with Wi-Fi module 593 in wireless module 491 shown in FIG. 4. As shown in FIG. 5, Wi-Fi module 593 is provided with an antenna 595 for receiving and transmitting Wi-Fi signals. Wi-Fi module 593 is configured to operate under the direction and control of module processor 480. For this purpose, Wi-Fi module 593 is connected to an SDIO port 591 of module processor 480 to enable module processor 480 to control the bidirectional flow of data to and from the Wi-Fi module 593. Module processor 480 may also control the processing of signals received by Wi-Fi module 593. The memory 485 (shown in FIG. 4) of the utility module may be used by the processor to perform the algorithms required for the Wi-Fi signal processing. Alternatively, a dedicated digital signal processor and associated memory included in the Wi-Fi module may be used to perform these algorithms to process the signals. In the latter case, the role of the module processor 480 may be to control the bidirectional flow of the wireless data processed by the Wi-Fi module through the utility module. Illustratively, the Wi-Fi module may be a Wi-Fi module RS9110-N-11-03 made by Redpine Signals. Alternatively, any Wi-Fi module that provides the functions detailed in this disclosure may be used.

Figure 7:
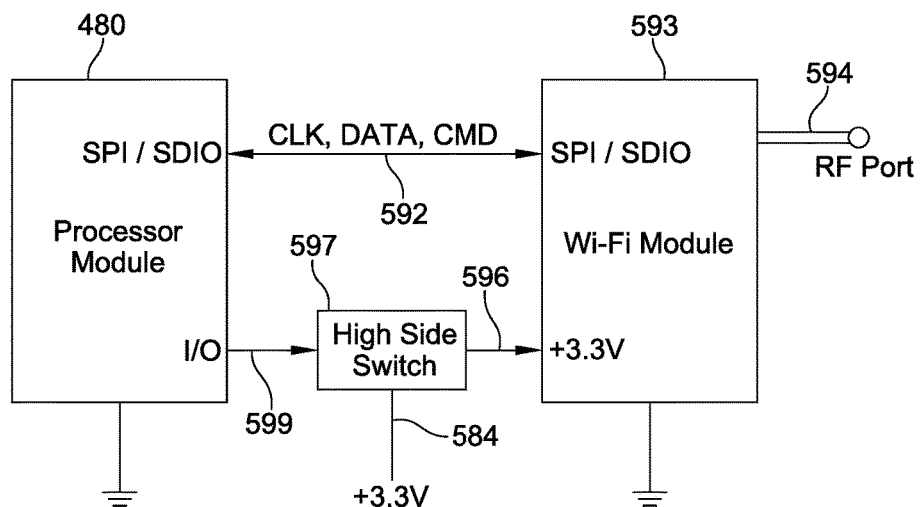
FIG. 7 is an enlarged view of the Wi-Fi Module included in the utility module shown in FIG. 5.

FIG. 7 is an enlarged view of the Wi-Fi Module 593 of FIG. 5 which also shows the control of power to the Wi-Fi Module 593 using a high side switch 597. High-side switch 597 and its operation are described in greater detail in the description of the power manager 550 later below. Generally speaking, high side switch 597 is controlled by module processor 480 through a managed control signal applied by module processor 480 to signal line 599. When the control signal is true, the high side switch 597 is turned on. This allows 3.3 volts of power on signal line 584 (illustratively the same signal line as in FIG. 6) to be applied to signal line 596 and to the Wi-Fi Module 593; causing the Wi-Fi module to power on. Control of the Wi-Fi module 593 occurs through clock, data, and CMD signals that are applied by module processor 480 to the Wi-Fi module 593. The SPI/SDIO signal lines 592 allows the module processor 480 to control the bidirectional transmission of data from the Wi-Fi module 593 throughout the utility module. Advantageously, this allows the utility module to import data from the Wi-Fi module which the utility module can make available to the defibrillator through data communication link 441 (see FIG. 4) and to other external devices through the communication module 490. The utility module may use the module data connect port 492 (See FIG. 4) of the utility module to export data to the external devices. More particulars on the communication between the utility module and external devices are described later below.

Referring again to FIG. 5, the Wi-Fi module 593 may also provide Wi-Fi-Status information to a user by displaying Wi-Fi status information on an indicator panel 520. The Wi-Fi status information may be provided using a Wi-Fi status LED 521 comprising one or more LED lights or banks of one or more LED lights. For instance, if only one LED is used, the light may be configured to turn "on" when the Wi-Fi module 593 is in an active mode of operation, "off" when the Wi-Fi module 593 is in inactive mode of operation, and "flicker on-off" when the Wi-Fi module 593 is transmitting or receiving data.

The USB circuit 601 of the communication module 490 is illustrative circuitry well known in the art for processing a signal for transmission over the USB connector 600. The USB connect 600 is configured to transmit data from the utility module 455 to an external utility such as adjunct medical device shown in FIG. 14 and described later below. The USB circuit 601 supports the USB connect 600.

An RS232 circuit 478 of the communication module is illustratively circuitry well known in the art for processing a signal for transmission over data outlet 475, which as illustratively described in FIG. 4 is configured according to the RS232 protocol. In FIG. 5, the data outlet 475 is illustratively configured to transmit data from the utility module in serial format to the defibrillator 410 shown in FIG. 4. As discussed below, this RS232 signal connector may be used for the bidirectional exchange of data between the utility module and the defibrillator. In alternative embodiments, additional RS232 outlets may be provided to allow for the bidirectional exchange of data between the utility module and devices external to the utility that are other than the defibrillator such as computers, servers, laptops, mobile computing devices, or other computing devices, as illustrated, for example, in FIG. 14.

The foregoing disclosure illustrates one of the advantages of the communication module 490 of this disclosure. The communication module of this disclosure enables the disclosed utility module to communicate bidirectionally with the defibrillator and external devices directly. In addition, the communication module allows the utility module to serve as a proxy for each or both the defibrillator and other devices external to the defibrillator; allowing the defibrillator and the other devices external to the utility module to communicate bidirectionally with each other through the utility module acting as proxy, with more details on the particulars of this implementation provided in greater detail later below. In other words, the disclosed utility module may be configured to serve as a proxy for the defibrillator by enabling the defibrillator to communicate through the utility module directly with an external device. Similarly, the disclosed utility module may be configured to serve as a proxy for devices external to the utility module by enabling the external devices to communicate through the utility module with the defibrillator. As proxy to either or both defibrillator and other devices external to the utility module, the utility module advantageously provides a gateway for a defibrillator and other devices external to the utility module to contact and communicate with each other. The ability of the utility module to both communicate directly with the defibrillator and external devices and to serve as a gateway for enabling communications between the defibrillator and external devices provides a powerful tool for integrating external devices and a defibrillator into an integrated defibrillation system according to this disclosure. Through this integration, one or more external devices may be brought into direct communication with a rescuer at the site of a defibrillation in order to observe and participate in the defibrillation process. This enables external devices to provide real-time coaching to the user of a defibrillator during a defibrillator process. The inclusion of a network of resources in the defibrillation process further enables a more holistic approach to be brought to the defibrillation process as compared to conventional approaches which are largely a private affair between the rescuer and the patient. In short, this disclosure advantageously makes possible the "virtual" participation of a network of resources in a defibrillation process.

Through this disclosure, external devices may also be educated with patient and other data obtained during and in connection with the defibrillation process which may be used in post-defibrillation procedures, coaching education, historical studies, and for other purposes. In addition to virtual participation by remote resources, the ability of the disclosed utility module to itself directly communicate with the defibrillator enables "physical" participation by a second team of rescuers using the utility module who are at the site of the defibrillation process but not actually administering the defibrillation. For example, where space constraints limit the number of rescuers that may occupy the immediate vicinity of the defibrillator, the utility module enables additional rescuers to assist in the defibrillation process from a contiguous or nearby vicinity in real-time since the utility module is in seamless communication with the defibrillator. In these and other configurations, the utility module 490 is seen to enable enhanced coaching and enhanced functionality to be brought to the defibrillator and/or the site of the defibrillation. These and other advantages are further elaborated upon and discussed below.

In the illustrative embodiment shown in FIG. 5, power source 465 shown in FIG. 4 is illustratively illustrated as the power manager 550. The power manager and included battery authentication and security schemes are described in detail later below.

Referring still to FIG. 5, utility module further comprises a fan 506 and a fan controller IC 503. The fan controller IC 503 applies a signal to fan 506 based upon a control signal applied by the module processor to the fan controller IC 503. The fan controller IC 503 generates its own fault or over temperature condition sensed by the fan controller IC for use by the processor in controlling the fan. The fan controller IC 503 is illustratively powered by a 5 volt signal from the power manager module 550. The fan 506 advantageously provides utility module 455 with circulating air to cool the components internal to the utility module 455 and to cool a docked defibrillator as described later in this disclosure.

Figure 8:
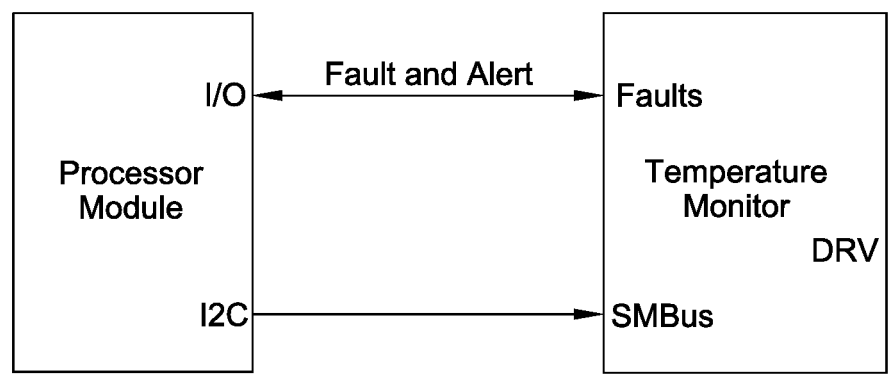
FIG. 8 is an enlarged view of the fan controller IC included in the utility module shown in FIG. 5.

FIG. 8 shows an enlarged view of the fan controller IC. Fan controller IC is illustrated in FIG. 8 as a temperature monitor to illustrate a feature of the fan controller IC 503 in controlling temperature. The electrical components inside the utility module generate heat and too much heat can lead to component failures. To prevent overheating, the temperature monitor includes a temperature sensor (not shown) configured to sense and monitor the temperature. The temperature monitor is controlled by module processor 480 (in FIG. 5) through a control signal applied by module processor through the I2C port. The module processor 480 communicates with the fan controller IC using an I2C protocol. The fan controller IC senses an overheating condition and triggers fault and alert information to the processor when the fan controller IC 503 detects an over-temperature condition or a failure of the SMBus. The processor may respond to fault and alert triggers from the temperature monitor by corrective signaling to adjust the speed of the fan or by utility module system turn-off in the event of a catastrophic overheating condition.

As previously discussed (FIG. 5), utility module 455 comprises an indicator panel 520. The indicator panel may comprise LED indicator lights for Wi-Fi status LED 521, AC/Battery LED 523, NET status LED 525, and Wi-Fi signal strength LED 527. The Wi-Fi status LED 521 has been previously described. The AC/Battery LED, NET status LED, and Wi-Fi signal strength LED are controlled by signals applied by the processor. For instance, the processor may signal the AC/Battery LED to turn "on" in order to indicate that there is an adequate charge on the battery and to turn "off" to indicate a need to recharge the battery. The NET status LED feature is a network service external to the utility module which may use the utility module of this disclosure as a proxy to coach the user of a defibrillator as indicated above and described in greater detail below. In connection with this feature, the processor may signal the NET status LED to be "on" to indicate that the NET service is connected or communicating with the utility module 455 and to be "off" to indicate a state in which the utility module is not connected or communicating with a NET service. The processor may also signal the Wi-Fi signal strength LED to indicate the strength of the Wi-Fi signal. For instance, the processor may signal the Wi-Fi signal strength LED light to be "on" to indicate that the Wi-Fi signal strength is strong, to be "flickering" to indicate that Wi-Fi signal strength is marginal, and to be "off" to indicate low Wi-Fi signal strength.

It will be appreciated that additional indicator lights and/or banks of indicator lights may be provided to the utility module of this disclosure to provide a user with more information. The additional information provided by the additional lights may include information on some other event, such as is whether a defibrillator is connected to the utility module or whether the defibrillator and the utility module are properly connected or whether the defibrillator is ready to place a charge on a patient. Alternatively, the additional information may be directed to more detailed information about any of the above or other pieces of information. For instance, a series of LEDs may be provided on the indicator panel 520 to provide more information about a single event such as the level of charge in a battery. For instance, a series of three lights may be used whereby the processor may signal all three lights to be "on" when the power available to the utility module is in a high power availability state. The processor may signal two lights to be "on" when the available power has dropped to an intermediate level; and one light to be "on" to alert the user that the power available to the utility module is low and the utility module should be connected to an AC outlet to be recharged. As yet another example pertaining to power, the processor may signal lights on the indicator panel to display fault conditions with the power system of the utility module 455. The ability to deliver effective and repeated charges from a defibrillator to a patient is fundamental to the successful use of the defibrillator and this disclosure enhances that ability. The indicator panel features of this disclosure including the Wi-Fi and NET connection and power availability features provide important coaching information to a user of a defibrillator useful in improving the success of a defibrillation.

Figure 9:
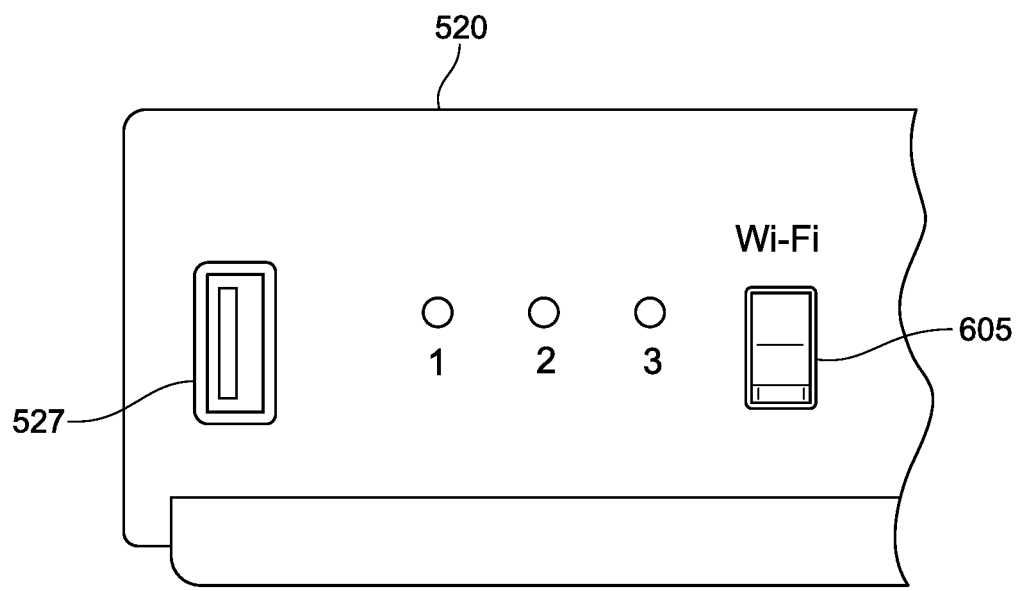
FIG. 9 shows an embodiment of the indicator panel included in the utility module shown in FIG. 5.

FIG. 9 shows an embodiment of the indicator panel 520 comprising a Wi-Fi signal strength gauge 527, a Wi-Fi manual ON/OFF switch 605, along with three LEDs illustratively one each for Wi-Fi status LED, AC/Battery LED, and NET status LED described above. The FIG. 9 panel is illustrative only and the particular information displayed and the arrangement of that display is a matter of design choice. It will also be appreciated that while the lighting has been shown as an LED lighting arrangement, any light source may be used to display the information on the indicator panel 520

The Wi-Fi manual ON/Off switch 605 is useful for quickly disabling Wi-Fi functionality where, for example, it is forbidden to use wireless communication. For instance, Wi-Fi is generally prohibited in a number of hospitals and in airplanes. If a patient undergoing defibrillation is being taken into a hospital or an airplane from an ambulance where, for example, the Wi-Fi functionality of the disclosed utility module was being used for coaching or for patient data downloads to an external device according to this disclosure, the user may simply flip the Wi-Fi switch off to prevent the utility module from interfering, for example, with hospital equipment, or with airplane avionics.

It will be appreciated from the discussion in FIGS. 4-9 above that utility module 455 may help optimize the timing and manner of applying a defibrillator charge to a patient based upon data provided by the utility module to the defibrillator and data provided by the defibrillator to the utility module. The data from the defibrillator may, for example be patient vital data and the data coming from the utility module may, for example be data generated internally to the utility module, such as patient parameter data from the parameter module 460 shown in FIG. 5. In addition as previously discussed, the data from the defibrillator may be passed by the utility module over to external devices and similarly the utility module may pass data from external devices to the defibrillator; in both cases with the utility module acting as a proxy to the source of the data. In either way, the utility module can use internally generated data and/or data provided by external devices to advantageously provide external coaching, to the user of the defibrillator to assist the rescuer to optimize the defibrillation results, such as the VF correction.

The ability of the utility module to serve as a proxy to both external devices and the defibrillator thus advantageously expands the paradigm of coaching available to a defibrillator from coaching that has conventionally been localized to coaching that may involve virtual resources that are connected to the defibrillator by a network through the disclosed utility module. As discussed in greater detail later below, the networked connection of external devices to a defibrillator through the utility module of this disclosure enables delivery of data from one or more external resources to the defibrillator; thereby enabling network participation in the defibrillation process such as by hospital monitoring of a patient or by coaching of the rescuer by trained medical personnel remotely in order to provide for a more effective defibrillation process. The external resources that may virtually participate in the defibrillation process and afterwards may illustratively be a medical director or an asset manager. These and other resources discussed below as well as users of the utility module are enabled by this disclosure to participate in the defibrillation process to provide a more holistic approach to the defibrillation process and a more effective defibrillation procedure.

To operate the defibrillator shown in FIG. 4, the defibrillator data connect port 440 and power connect 445 of defibrillator 410 are electrically connected to the data outlet 475 and the power outlet 470, respectively, of the utility module 455. In particular, defibrillator data connect port 440 of defibrillator 410 is received by data outlet 475 of utility module 455 to provide the data communication link 441 shown in FIG. 4 for the bidirectional transmission of data between defibrillator 410 and utility module 455. Similarly, power connect 445 is received by the power outlet 470 to provide the power link 450 shown in FIG. 4 for the transmission of power between the utility module and the defibrillator.

In operation, both the defibrillator and the utility module are first powered on. The power-on enables power to be transmitted from the defibrillator to the utility module or from the utility module to the defibrillator over the power link 450 as further described later below. Illustratively, the power source 465 of the utility module is provided with an electrical cord with a plug connector. Typically, the plug connector is connected to an AC outlet for providing AC power to the utility module from an AC power source when AC power is available. An AC-to-DC converter (not shown) internal to the power manager 550 (in FIG. 5) converts the AC power to the DC power levels required to operate the utility module as well as the DC power level that is applied to the power outlet 470 of the utility module for use by a defibrillator when connected. When AC power is unavailable or inadequate, the power manager 550 (see FIG. 5) is configured to switch the power that is used by the utility module and applied to the power outlet 470 of the utility module over from AC power to the power source 465 which provides DC power from a battery as described later below. The delivery of power within utility module is managed by a battery manager IC shown in FIG. 28 and discussed later below. In an alternative embodiment, if on power-up, there is neither adequate AC power available nor adequate charge in the DC source within the power source 465, then the defibrillator may be configured to provide power to the utility module over power link 450. In this example, the power from the energy storage device 415 of the defibrillator is used to power both the defibrillator and the utility module; although this is not a preferred mode of operation. More typically, it is the other way around with the utility module providing the power requirements for powering the defibrillator. In either case, the power manager 550 shown in FIG. 5 and described in FIG. 28 below of the utility module is configured to manage the power flowing between the two devices over power link 450 when both devices are powered on.

Hence, the utility module is seen to also provide defibrillators with a reserve of power to enable defibrillators to extend the length and number of charges that may be delivered by the defibrillator. This enables defibrillators to be used where power is unavailable and to enable defibrillators to deliver multiple charges more readily anywhere, anytime.

Once both devices are powered on, the data communication link 441 shown in FIG. 4 is established; thereby allowing data from the defibrillator and from the utility module to be transmitted to the other device over the data communication link 441. Illustratively, the transmission occurs in accordance with the RS232 protocol as previously discussed. Alternatively, the transmission of data over the data communication link 441 may occur using the USB protocol or other protocol. Data may also be transmitted using non-standardized methods. Further, while the RS232 protocol provides for the serial transmission of data, it will be appreciated that the data may be transmitted in parallel or other formats. In addition, while the data connection link 441 has been described as a wired connection, it will be appreciated that the data connection link 441 may also be a wireless data communication link.

Hence, at power-on, the defibrillator and the utility module in the disclosed defibrillation system are seen to share both their data and power resources with the other device which provides the user with additional functionality for use in improving the defibrillation process. For example, the bidirectional flow of data and power made possible by this disclosure allows the two devices to work together as a team in a system enabling the user to provide a more effective defibrillation to a patient. With respect to shared data resources, the system allows the utility module to provide the user of the defibrillator with coaching based on data generated by the utility module, such as patient parameter data; as well as data generated externally to the utility module by network resources and that the utility module passes through to the defibrillator as a proxy of the network resources as discussed herein. In addition, the system allows the defibrillator to provide the utility module and external devices with defibrillator data that enables the utility module and external resources to tailor their coaching of the defibrillator to fit the data as discussed in greater detail below. Moreover, the defibrillator data provides a valuable source of relevant data useful for post-defibrillation treatment. The defibrillator data may also be used for coaching-improvement activities, data studies, or other purposes.

Figure 10A:
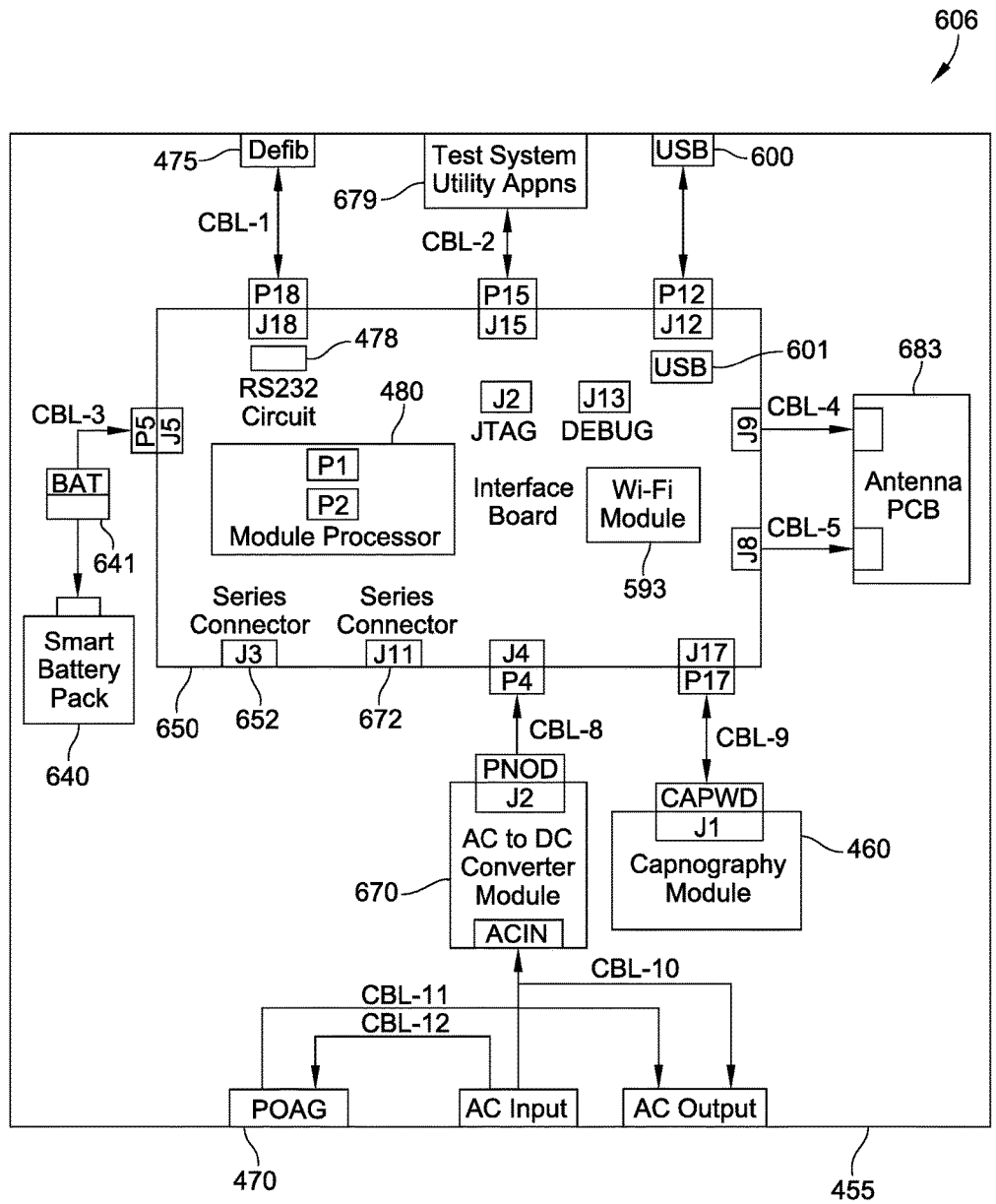
FIG. 10A shows an illustrative embodiment of an electrical circuit configuration for the utility module of FIG. 5 of this disclosure.

FIG. 10A shows an illustrative embodiment of an electrical circuit configuration 606 for the utility module 455 of FIG. 5 of this disclosure. The circuit configuration 606 comprises interface board 650, smart battery pack 640, antenna PCB 683, capnography module 460, and AC-to-DC converter module 670. The interface board 650 comprises a module processor 480 illustrative including a first processor P1 and a second processor P2, a Wi-Fi module 593, an RS232 circuit 478, a USB circuit 601, a series of connector outlets and a series of connectors as shown in the figure. The connector outlets and connectors shown in the FIG. are used to connect the elements shown in FIG. 10 to form electrical connections between the elements; such as connecting the smart battery pack 640 including battery 641 to the interface board 650; connecting a data outlet 475 to the interface board 650; connecting the interface board to a test system 679; connecting a utility connect 600 which is configured to receive a USB connector (not shown); connecting antenna 683 with the interface board 650; connecting the capnography module 460 to the interface board 650; and connecting an AC-to-DC converter module 670 to provide DC power to the interface board. An electric circuit printed on the interface board 650 provides the electrical signal lines for electrically connecting these components together into an illustrative utility module of this disclosure.

Advantageously, series connectors 652 and 772 are available for use in providing connections to other modules that may be added to the utility module to enable the utility module with more functionality. For example, the illustrative embodiment of FIG. 10A shows a utility module configured with a capnography module 460 which is used to measure the $CO_2$ exhaled by a patient. Series connectors 652 and 672 and other connectors may be used to configure the utility module for use with other parameter measuring modules as well; adding to the functionality enabled by the capnography module. For example, these and other series connectors may be used to configure the utility module with capnography module to also be used with a module that measures the electrical activity of the heart of a patient. The series connectors may be used to configure the utility module for use with a module that measures the pressure of the blood in a patient using non-invasive blood pressure measurement techniques or invasive blood pressure measurement techniques. The series connectors may be used to configure the utility module for use with a module that measures the temperature of a patient using temperature measurement techniques. The series connectors may be used to configure the utility module for use with a module that measures an oxygen saturation in the blood of a patient using pulse oximeter techniques or tissue oximetry techniques. The series connectors may be used to configure the utility module for use with a module that measures a chest compression of a patient using chest compression detection and feedback techniques. The series connectors may be used to configure the utility module for use with a module that measures an image of the internal structure of a patient using ultrasound measurement techniques. The series connectors may be used to configure the utility module for use with a module that measures an oxygen saturation in the blood in the brain of a patient using cerebral oximetry techniques. The series connectors may be used to configure the utility module for use with a module that measures the acidity or alkalinity of fluids in a patient is measured using non-invasive pH measurement techniques. Hence, connectors such as 652 and 672, as well as other wired or wireless ways of connecting a module to the interface board, provide a way for enabling the utility module with more robust functionality.

Figure 10B:
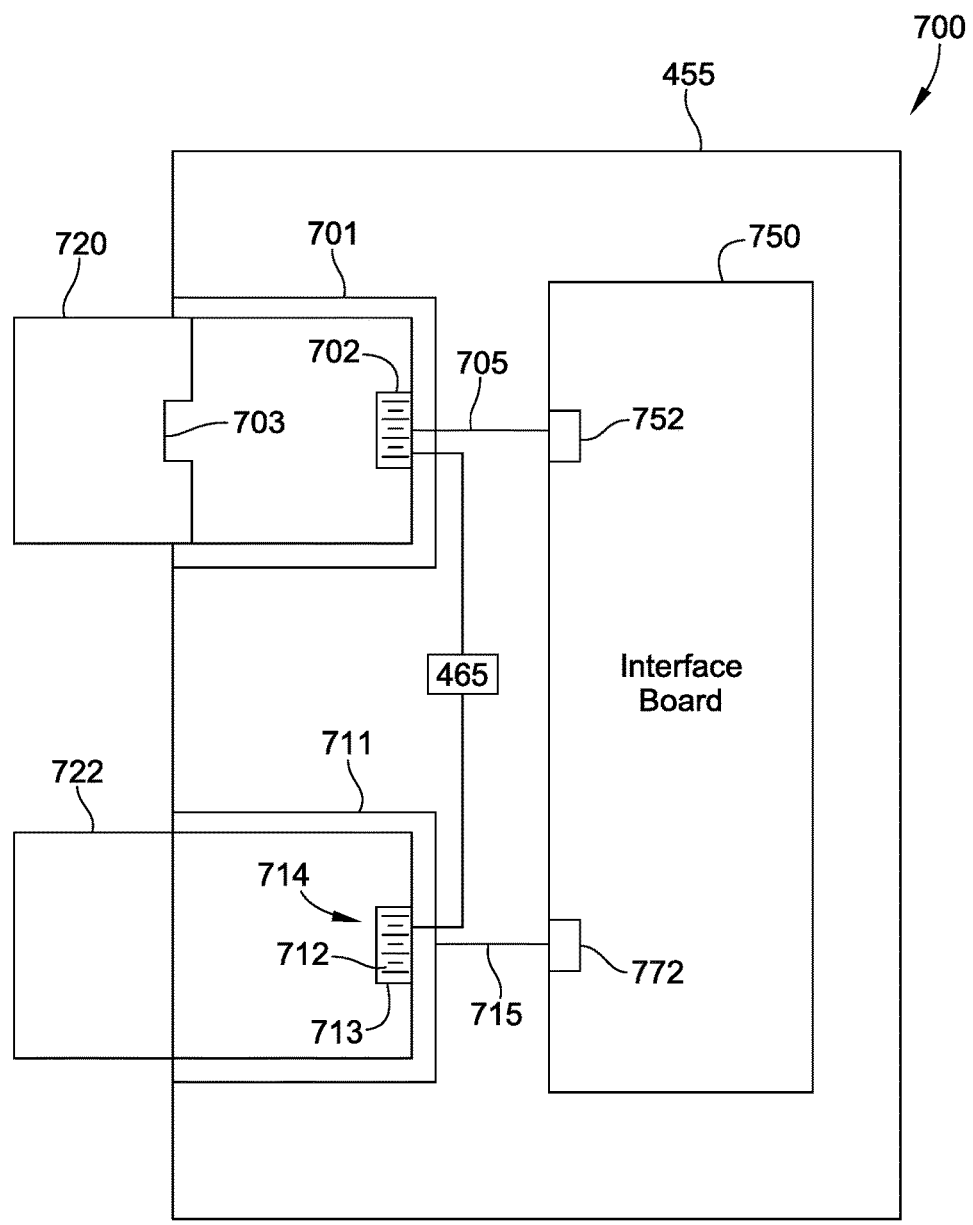
FIG. 10B shows an illustrative utility module of FIG. 5 with a modular design that may be readily scalable in performance by the inclusion of parameter or other module cartridges after manufacture to provide a bundled utility module.

The decision of whether or not to include one or more additional modules into a utility module may depend on the intended application of the utility module and also the cost. In some cases, a user may not want to include one or more additional modules at the time of purchase either because it is not needed or because doing so is cost-prohibitive. However, at some later point in time, the user may want one or more additional modules added to the purchased utility module to give it more functionality and/or robustness. As shown in FIG. 10B, this disclosure addresses this problem by providing a utility module with a modular design 700 that may be readily scalable in performance by the inclusion of one or more parameter module cartridges 720, 722, or other modules after manufacture; making the disclosed utility module configurable for any application or budget. In this scalability feature of this disclosure, the utility module 455 is provided with one or more receptacles 701, 711 for receipt of additional modules 720, 722 that may be provided as cartridges. The receptacles 701, 711 are each provided with an electrical connector 702, 712, which are in wired connection with electrical connectors 752, 772 of the interface board 750 previously described in connection with FIG. 10A as well as power source 465 of the utility module 455. The utility module cartridges 720, 722, are illustratively each likewise provided with electrical connectors 703, 713 for mating engagement with electrical connectors 702, 713. FIG. 10B shows one such mating engagement 714 formed between connectors 712 and 713 of receptacle 711 and utility module cartridge 722 respectively. The mating engagement provides an electrical connection of the utility module 722 both to the power source 465 and the data bus 705, 715. The power source provides the inserted utility module cartridges with power from the utility module 455 to operate and the data bus 705, 715 provide a data communication link between the inserted utility module cartridges 720, 722 and the utility module 455; enabling the inserted utility module to add its functionality to the functionality already provided by utility module 455.

Hence, the scalability feature of this disclosure described in FIG. 10B enables the utility module of FIG. 10A which is illustratively provided with capnography functionality only to be boosted in functionality by the inclusion into the utility module 455 of one or more additional utility module cartridges 720, 722 each containing an additional functionality. These utility module cartridges are illustratively parameter modules that measure parameters that are different from those measured by a capnography module. For example, the inserted utility module cartridge may include functionality that measures an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; or the acidity or alkalinity of fluids in a patient. Alternatively, one or more of the inserted utility module may include a plurality of the foregoing parameter modules to enable the capnography module illustrated in the FIG. 10A with even more functionality to monitor a plurality of patient parameters.

In addition, the one or more inserted utility module cartridges need not be modules that measure a patient parameter different from the capnography module used in the FIG. 10A example; or whatever other module an original utility module may be purchased with. Indeed, the additional module cartridges may also include one or more capnography modules which provide the utility module 455 with multiple capnography measuring capabilities; thereby allowing the utility module 455 to be used with different patients contemporaneously. In this example, at least one of the capnography modules may also be used for redundancy purposes, for use in the event one of the one or more other capnography modules fails.

Moreover, it will be appreciated that module cartridges other than parameter module cartridges may be used with this disclosure. For example, a utility module 455 that was purchased with a communication module (FIG. 4) that provides Wi-Fi functionality could be boosted in performance by inserting for utility module cartridge 720 shown in FIG. 10B, a utility module cartridge that is provided with Blue Tooth or CDMA functionality, for example. It is hence seen that a set of two or more utility module cartridges—each with its own one or more parameter or other modules connected to its own interface board in a manner similar to the way the capnography module is shown connected to the interface module in FIG. 10 or in other ways may be connected together with utility module 455 to provide a more functional and robust bundled utility module (e.g., in this example, the utility module with modular design 700 together with one or more utility module cartridges like utility module cartridges 720, 722 electrically connected thereto) for use with a defibrillator. The bundled utility module enhances the effectiveness of the coaching that may be provided to a rescuer performing a defibrillation since the coaches that are making use of the bundled utility module, whether located at the site of the utility module or remotely participating in the defibrillation process virtually over the network, have more patient data to work with as a result of the more functionality and/or robustness in one or more specific functionalities provided by the bundled utility module of this disclosure.

Figure 30:
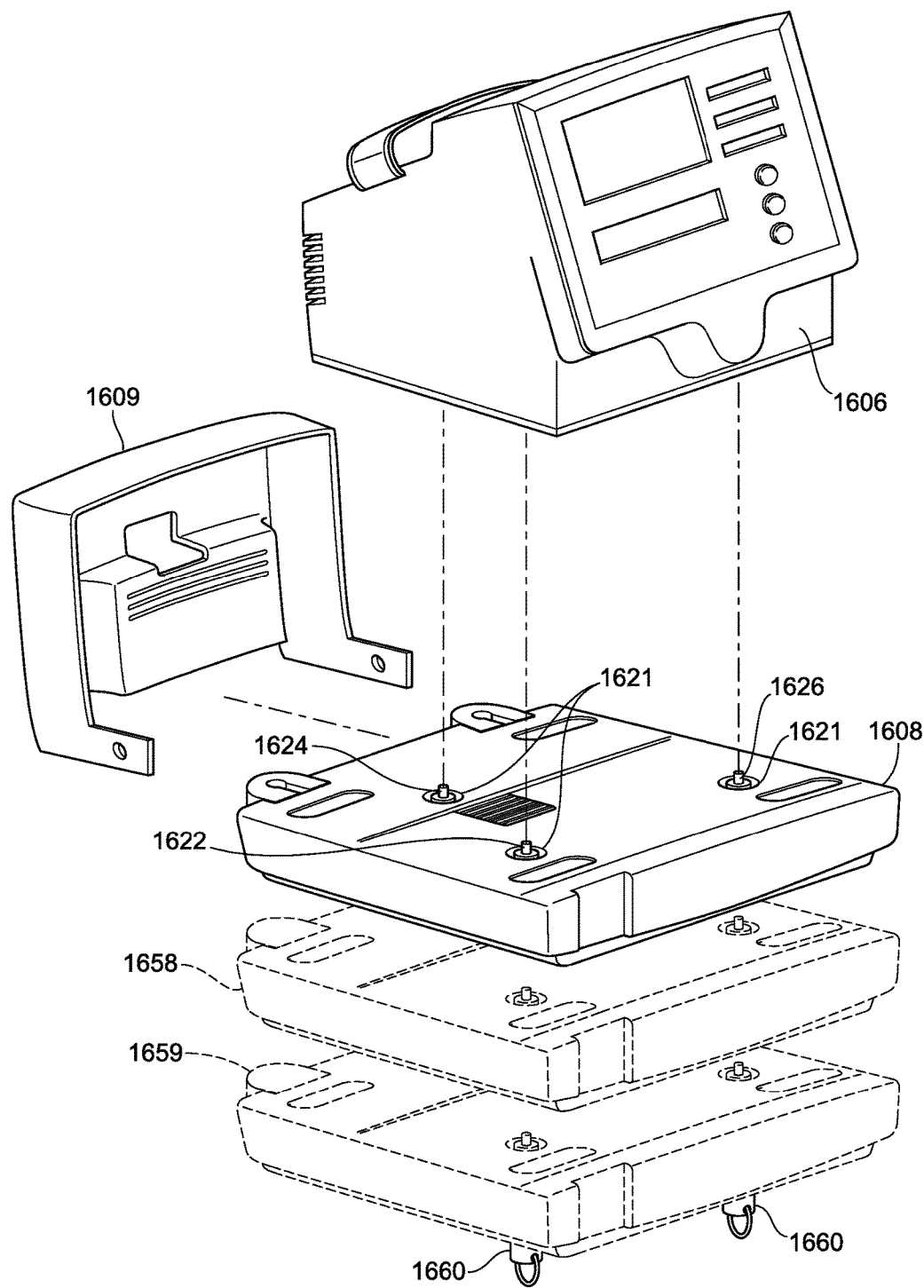
FIG. 30 is an exploded view of an assembly of a defibrillator and a plurality of stacked utility modules to provide a bundled utility module according to this disclosure.
Figure 33:
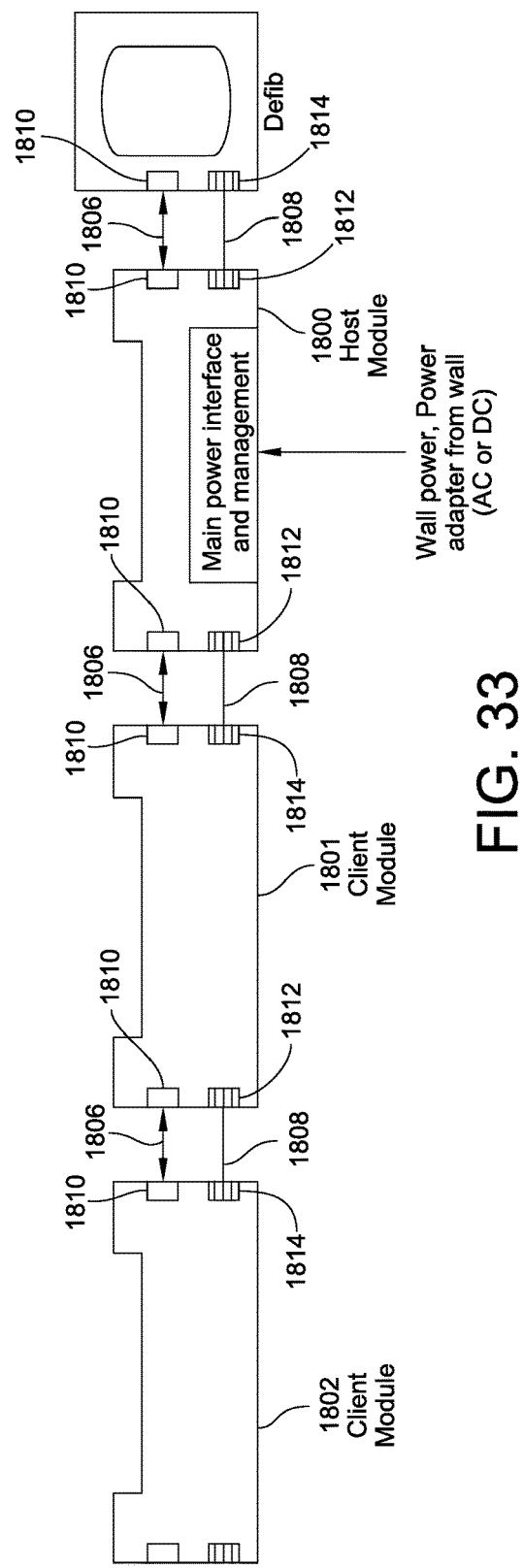
FIG. 33 depicts a first utility module electrically connected with additional utility modules for bidirectional communication with the additional modules and which are powered from the first utility module to provide a bundled utility module.

As an alternative to creating a bundled utility module using utility module cartridges, this disclosure provides additional ways in which a bundled utility module may be provided including arrangements involving electrically interconnecting two or more independent utility modules as discussed in connection with FIGS. 30 and 33 below. For example, FIG. 30 illustrates the use of individual utility modules bundled together in a vertical stacked arrangement. FIG. 33 illustrates how individual utility modules may be linked together in a daisy chain arrangement.

Figure 11:
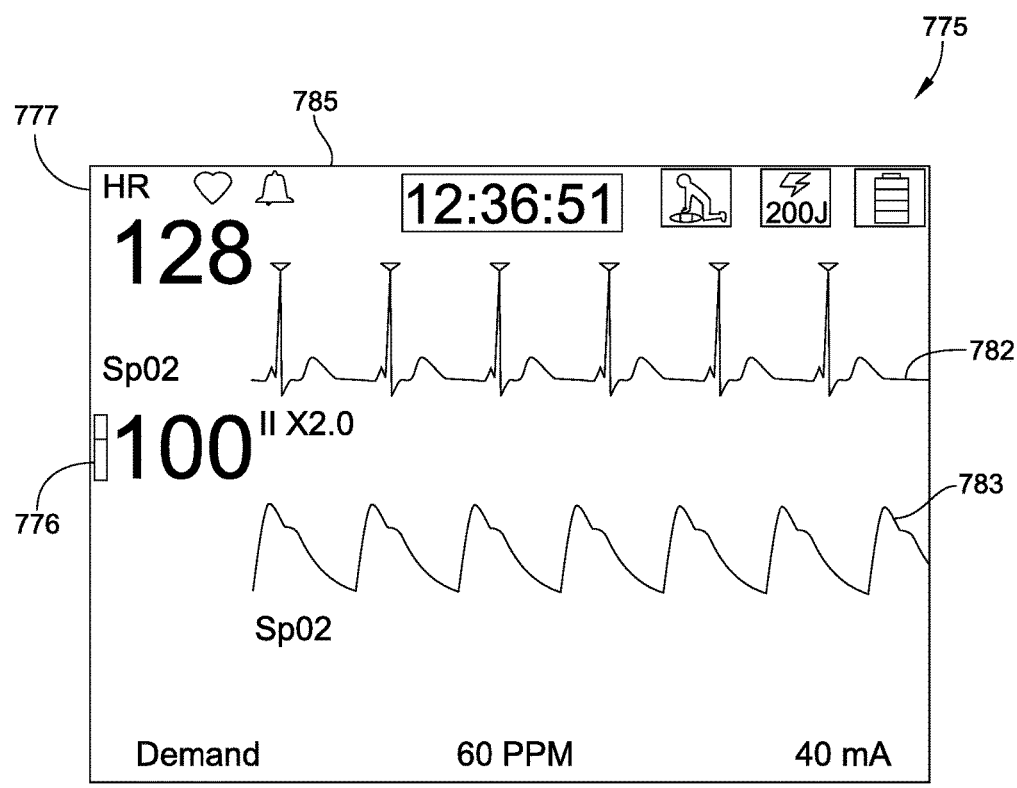
FIGS. 11, 12, 13 show illustrative examples of a display of certain information that may be displayed on a display of the defibrillator shown in FIG. 4 for the purpose of coaching the user on the use of the defibrillator when connected to the utility module in accordance with the disclosed system.

FIG. 11 shows one illustrative example of a display 775 of some information that may be displayed on a display 425 (FIG. 4) of the defibrillator for the purpose of coaching the user on the use of the defibrillator when connected to the utility module of FIG. 4 in accordance with the disclosed system. Display 775 shows a display screen 785 on defibrillator 410 (FIG. 4) which displays heart beat waveform 782 along with heart rate information of 128 together with an SpO2 waveform 783 along with SpO2 information of 100 and an iconic gauge 776 showing the SpO2 level of the patient. Both the heart beat information and the SpO2 levels are generated by the defibrillator in this example.

Figure 12:
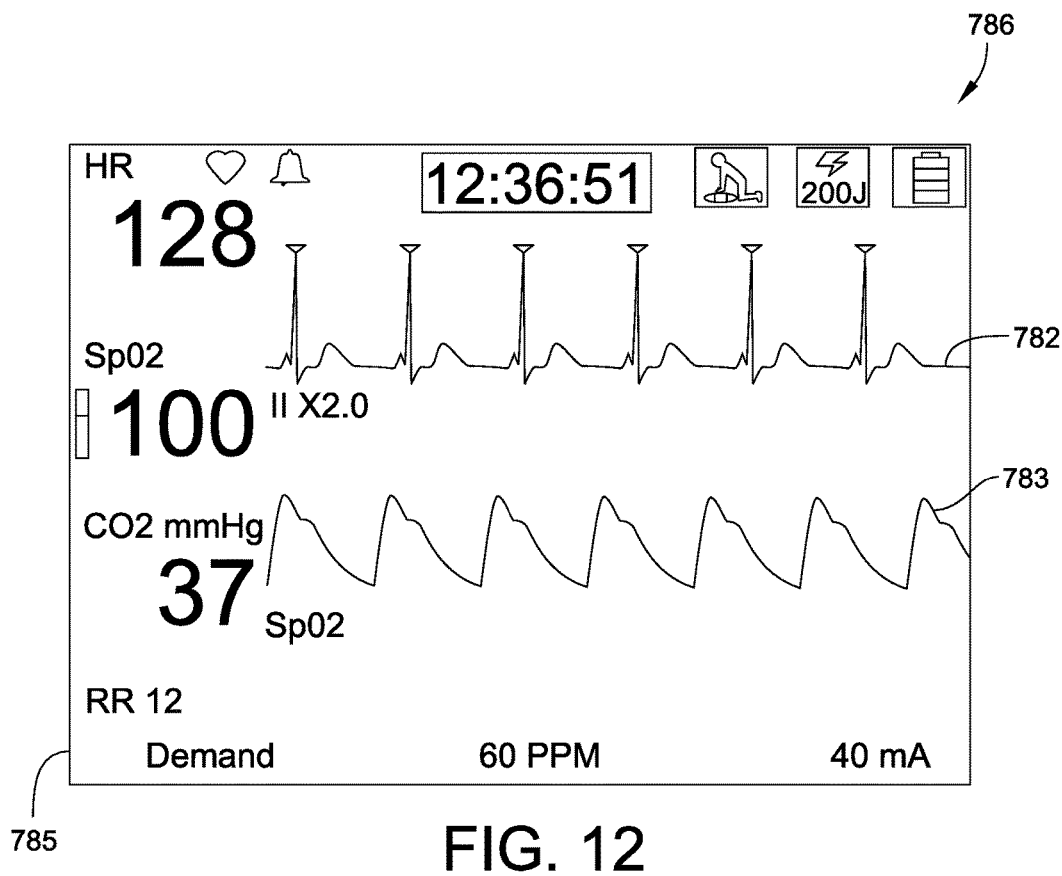

As previously discussed, the utility module of this disclosure illustratively includes a parameter module that is illustratively a CO2 parameter module. Referring now to FIG. 12, display 786 shows the advantages provided by this feature of the disclosure in that the CO2 information generated by the utility module is advantageously displayed on the display of the defibrillator shown in FIG. 12. The CO2 information is illustratively displayed by way of mmHg information which in this case is 37 mmHg. Hence, in FIG. 12, a utility module is seen to provide the user of the defibrillator with coaching based on the CO2 information of the patient which the user may advantageously use to improve the success of the defibrillation.

Figure 13:
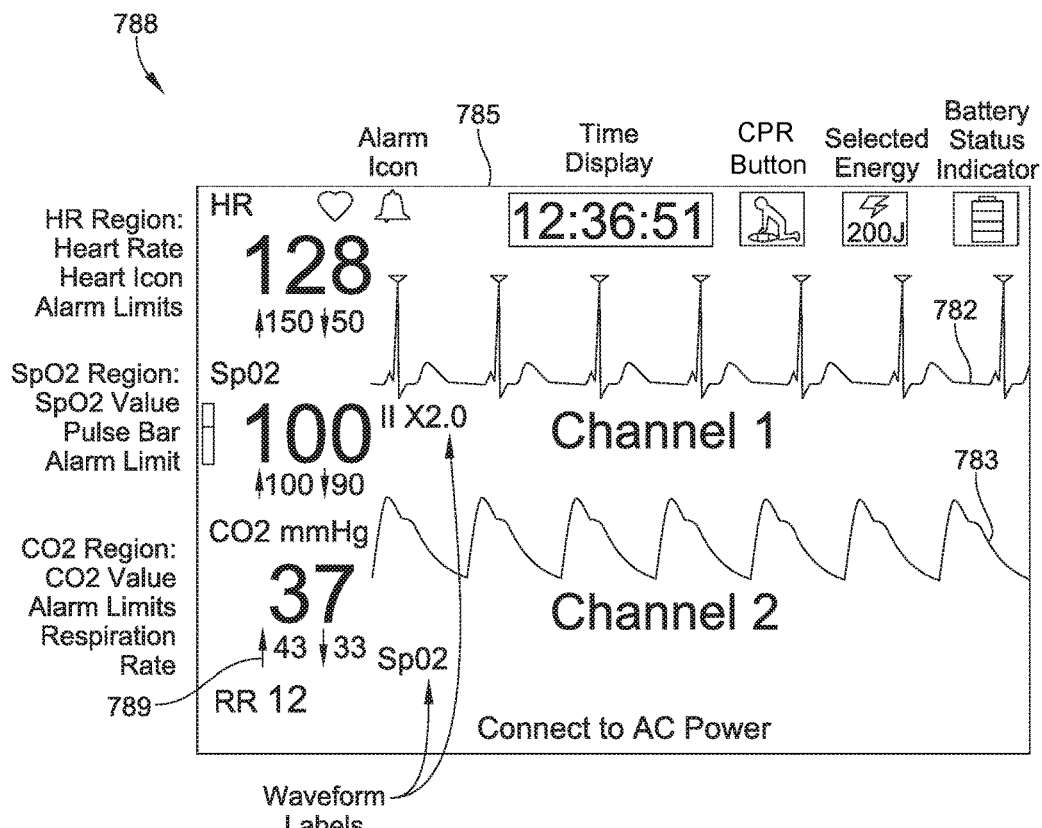

In FIG. 13, display 788 shows further information that may be provided to the defibrillator by the utility module of this disclosure. Display 788 shows a display screen 785 on defibrillator 410 (FIG. 4) which in addition to displaying the information in FIG. 12 is further displaying CO2 alarm limits in the form of the high and low range of CO2 789 in the breath of a patient which is shown as 43 mmHg and 33 mmHG, respectively, on the defibrillator display. This FIG. 13 hence further illustrates the advantageous feature of the disclosure in which a utility module is providing the user of the defibrillator with coaching based on the CO2 information of the patient which the user may advantageously use to improve the success of the defibrillation. In another illustrative embodiment, the CO2 signal itself may also be displayed on the defibrillator display. In addition, each of the heart information and the SpO2 information respectively shows the high and low alarm limits for each of the heart rate and the SpO2 rate. This range is typically calculated by the defibrillator processor but may be calculated in the module processor.

Alternatively, the module processor of the utility module of this disclosure may be used to make these and other more complex computations; thereby freeing up the processor of the defibrillator to perform other tasks. For this purpose, the defibrillator may down-load in real-time the heart and SpO2 data it generates to the utility module over the data communication link 441 (FIG. 4) that is established between the defibrillator and the utility module. The utility module processor may then perform the complex computations and return the computed data to the defibrillator for display on the defibrillator display. In this way, the utility module may free up the processor of the defibrillator to perform other vital operations; thereby advantageously serving the defibrillator with additional utility module resources to allow for a more effective defibrillation.

While the foregoing FIGS. 11-13 illustrate the display of CO2 data generated by the utility module on the display of the defibrillator for coaching purposes, it will be appreciated that data from other patient parameter modules included in the utility module may also be displayed on the display of the defibrillator for coaching purposes For example, the utility module may coach the defibrillator with data in connection with an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; and/or the acidity or alkalinity of fluids in a patient.

These data may be generated from parameter detection modules that: measure $CO_2$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; and the acidity or alkalinity of fluids in a patient.

Further, there may be other data that the utility module may generate internally or receive from external devices that the utility module may send to the defibrillator and this data too may be displayed on the display of a defibrillator. The display of data from the disclosed utility module (either generated internally or passed through from external resources) illustrates the coaching advantages made possible by this disclosure. Coaching information from external resources or the utility module is immediately available to a rescuer for use in the defibrillation. The coaching information can be made immediately available by display on the defibrillator display as indicated in the previous example. Alternatively, it may be made available in other ways, such as by triggering audible or visual data streams to assist in the defibrillation process. For example, the disclosed utility module may enable a live video or audio stream to be fed to the defibrillator in order to provide live or delayed audio or video to coach the rescuer through a defibrillation process, whether it be for coaching relating to setting or applying the charge to the patient, to the mechanics of CPR techniques that may be used in the process, or to other aspects of a defibrillation. As another example, the utility module may pass video feed from an external device through to the defibrillator for display on the defibrillator display for the purpose of providing the user with further coaching information. The video feed from the external device may include a video stream generated by an external device such as a laryngoscope or an ultrasound wand. In another illustrative embodiment, the utility module may be provided with a display and the utility module may display the video feed from the external device on the display of the utility module again for the purpose of providing the user with further coaching information. In this embodiment, the display of the utility module may also be used to show patient or device data as an adjunct to the defibrillator display; thereby freeing up space on the defibrillator's display. As yet another example, the disclosed utility module may trigger audible or visual alerts on the defibrillator when the defibrillation process moves close to or outside an operating envelope that has been defined for operation of the defibrillator.

In addition, the disclosed utility module enables the control of the defibrillator remotely whereby a remote resource may partly or completely take over control of the defibrillator functionality that determines the defibrillation operation such as settings, such as the charge level to be applied to a patient. This feature enables trained medical personnel to determine and set the proper operation, settings, etc. of the defibrillator in circumstances where the rescuer at the scene may be without the medical training to make these determinations; thereby increasing the likelihood of success of the defibrillation. As a result, defibrillator-monitors—which are intended to be used by persons in the medical profession, such as doctors, nurses, paramedics, emergency medical technicians, etc. who may be trained to provide medical treatment to the patient during a defibrillation process based upon information provided by the monitor—that are used with the disclosed utility module may be deployed more widely. No longer is it necessary to generally limit access to such a defibrillator-monitor to trained medical professionals. With the disclosed defibrillation system, the defibrillator-monitor may be used more widely in the field. In a normal mode of operation, these defibrillator-monitors that may be widely deployed may come with the functionality requiring trained medical expertise to operate disabled so as to allow the defibrillator part of the device to be used broadly by members of the public provided they have obtained first aid and CPR/AED training, much like the broad deployment conventionally seen with an AED. In a second mode of operation, such as a monitoring mode of operation, the monitoring functionality of the defibrillator-monitor that is used with the disclosed utility module may be enabled. In one embodiment, the enablement occurs by remote resources that can take over and use this functionality remotely. In another embodiment, the enablement may occur by a doctor or other medically trained personnel who happen to be at the site where the defibrillation is needed. In these instances, the monitoring functionality may be enabled by the trained medical personnel such as by entry of a password into a keyboard that may be provided on the defibrillator-monitor. In another example, the functionality may be enabled remotely after a network resource has validated the identity of the medical provider qualified to use the monitoring functionality. In either and other cases, the disclosed system enables more pervasive use of defibrillator-monitors in the field because of the controls on the use of the monitoring features that are provided by this disclosure.

In the above and other ways, a utility module configured with one or more of these parameter modules, or a set of utility modules with one or more of these parameter modules and bundled together in a stack or other arrangement, when used together with a defibrillator, form a defibrillator system that allows for a wide range of information to be made available to the user of the defibrillator to aid in the defibrillation process. The foregoing and other coaching provided by the utility module in the defibrillator system of this disclosure thus helps a user of a defibrillator to optimize the timing and manner of applying a defibrillator charge to a patient based upon these parametric conditions. The foregoing and other coaching provided by the utility module in the defibrillator system of this disclosure helps assist the rescuer optimize the timing and manner of applying a defibrillator charge to a patient. The utility module in the defibrillator system of this disclosure enables external devices to better coach users of the defibrillator through data transmitted to the defibrillator through the utility module as a proxy for the external devices as described in greater detail below. The utility module of this disclosure may also receive data from the defibrillator during or before or after defibrillation for use by the utility module or for transmission by the utility module as proxy to the defibrillator to external devices also as described in greater detail below. The utility module in the defibrillator system of this disclosure also helps provide defibrillators with a seamless communication link for the communication of data between the defibrillator and the one or more external devices. The utility module in the defibrillator system of this disclosure also helps provide defibrillators with a seamless integration with one or more external devices into a system that can provide a more holistic approach to the defibrillation process and a more effective defibrillation process.

FIG. 14 shows an illustrative embodiment of a defibrillator system 800 comprising the defibrillator system 400 of FIG. 4 and a network 870. The defibrillator system 400 comprises defibrillator 410 and utility module 455 of FIG. 4. The defibrillator 410 components of defibrillator port 420, energy storage device 415, defibrillator processor 435, memory 430, defibrillator data connect port 440, and power connect 445; as well as the utility module 445 components of a module processor 480, a memory 485, a communication module 490, a parameter module 460, a power source 465, and a power outlet 470 are the same in description and operation as like number components in FIG. 4. The utility module components of utility connect 600, USB circuit 601, RS232 circuit 478, Wi-Fi module 593, module data connect port 492 are the same in description and operation as like number components in FIG. 5 The network 870 comprises a server 810, and a utility application 820 (e.g., a device agent or other application) on a computer (e.g., laptop or PC). While the device agent on computer is shown in this illustrative figure to reside externally to the utility module, it will be appreciated that the device agent may be configured to reside on the utility module. The network 870 may additionally or alternatively comprise an adjunct medical device 850 and/or other existing applications on a computer.

Server 810 may be any computer configured to serve the requests of client programs running on the same or other computers on a network. The computer configured to serve the requests of client programs is known as the host computer. The programs running on the same or other computer that are served by the host computer are known as clients. The clients provide the graphical user interface and perform some or all of the processing requests it makes from the server which maintains the data and processes the requests. Depending on the computing service that server 810 is configured to offer, server 810 may include one or more of a file server for storing and making files accessible for reading and writing to the client, a print server that manages one or more printers, a network server that manages network traffic, a mail server that manages mail on a network, a database server that allows clients to interact with a database, and/or a hospital server for managing hospital records. Server 810 may also be in communication with one or more other servers that themselves may include one or more of the foregoing or other servers.

Utility applications 820 may be a device agent or other application. The device agent is a client software program that is configured to act for utility module 455 as an agent. Hence, the utility module 455 may serve as the host for the device agent in this example. FIG. 14 shows device agent illustratively residing on a laptop or personal computer external to the utility module. The external computing device may be a personal computer, a laptop computer, a tablet, a mobile computing device, or a server. Alternatively, device agent may reside in the memory unit 485 of the utility module itself. The adjunct medical device 850 is a programmed computer that provides tools for monitoring the technique of a rescuer during the defibrillation process, such as applying CPR or proper positioning of the electrodes for application of a defibrillation charge on the patient. Illustratively, the device may monitor CPR chest compressions provided before or after defibrillation shock. For example, the device may measure the depth of a CPR chest compression, compare it to what it should be, and provide feedback to the user by way of instructions to go faster, deeper, etc. Alternatively, the adjunct medical device may be any other device that monitors defibrillation techniques and provides feedback to a rescuer at the site of the defibrillation.

Utility applications 820 may also include existing applications that may be one or more software applications running on one or more computing device external to the utility module for performing a dedicated function. Examples of such functions include: performing specific services or tests. The external computing device may be a personal computer, a laptop computer, a tablet, a mobile computing device, or a server.

As previously described in connection with FIG. 4, the defibrillator data connect port 440 and power connect 445 of defibrillator 410 are received by the data outlet 475 and power outlet 470 of the utility module which each function and operate in the manner previously described in connection with the like numbered components described in connection with FIG. 4. In FIG. 14, communication module 490 includes the USB connect 600 with associated USB circuit (not shown), the Wi-Fi module 593, an RS232 circuit 478 interfacing with data outlet 475 which all function and operate in the manner previously described in connection with the like numbered components described in connection with FIG. 5. Communication module 490 in FIG. 14 further includes an RS232 interface 801 which functions and operates in a like manner previously described in connection with RS232 circuit 478 and data outlet 475 in connection with FIG. 5.

As shown in FIG. 14, power 450 from power outlet 470 is received by power connect 445 for use by defibrillator 410. In addition, bidirectional data over data communication link 441 passes between utility module and the defibrillator through data outlet 475 and defibrillator data connect port 440. In the defibrillator system 400 of FIG. 4, it was described how the defibrillator system 400 advantageously allows for the flow of bidirectional data between the utility module and the defibrillator. This data may include CO2 and capnography data transmitted from parameter module 460 of the utility module to the defibrillator as described in FIG. 5. As FIG. 14 further illustrates, this flow of bidirectional data advantageously enabled by the defibrillator system 400 (FIG. 4) may also flow from the defibrillator to the utility module and include patient episode data and device self test status.

The system 800 shown in FIG. 14 expands the coaching capabilities of the FIG. 4 defibrillator system by including the network in the system and enabling several communication links for providing bidirectional flows of data between the utility module, the defibrillator, and external devices in the network. For example, the system advantageously provides for the bidirectional flow of data between the utility module and the defibrillator as previously described. For example, the utility module may provide the defibrillator with CO2 or other physiological data from a parameter module and receive vital patient data from the defibrillator. The memory of the utility module may also provide additional memory capability to the defibrillator by storing patient data that is unable to be stored in the defibrillator's memory because the defibrillator memory is full; thereby providing memory back-up and redundancy to the defibrillator for supporting the defibrillation process and user coaching. Further, the system advantageously provides data communication links 441, 803, 805, 807 for the bidirectional flow of data between the defibrillator and one or more external devices through the utility module acting as proxy for whichever device (e.g., the defibrillator or the external device) is the source of the data. For example, the utility module may transmit the patient episode data received by the utility module from the defibrillator over to the server 810 of the network by way of data communication link 803. This patient episode data from the utility module to the server may be reformatted by the utility module or simply passed through the utility device in the format in which the defibrillator has put that data. In the former case, the utility module additionally provides a formatting functionality to the patient episode data. In the latter case, the utility module serves as a conduit for the transfer of the patient episode data received from the defibrillator directly over to the server 810.

In addition, the utility module may also transmit and receive data transmitted between the utility applications 820 and the defibrillator over communication link 807. For example, device agent may update the software and software configuration settings on the defibrillator by providing the utility module with update device software/setup data for pass-through to the defibrillator. Data flow in the other direction may include the utility module passing through to the utility applications 820 enrollment information provided by the defibrillator.

In addition, the system advantageously provides for the bidirectional flow of data generated by the utility module between the utility module and one or more external devices. For instance, the CO2 and capnography data generated by the parameter module 460 of the utility module may be transmitted by the utility module over to the server 810 of the network 970 over communication link 803 according to this disclosure. The utility module may also transmit other data to the server 810 such as data from an adjunct medical device, utility module status data, and device self status data. The utility module may also transmit and receive data from the device agent. For example, device agent may update the software and software configuration settings on the utility module and/or the defibrillator by providing the utility module with update device software/setup data for use by the utility module or for the utility module to pass on through to the defibrillator. The device agent may also provide the utility module with a listing of preferred networks for the Wi-Fi module of the utility module to use when connecting wirelessly within the network. Data flow in the other direction may include the utility module providing the device agent with enrollment information on the utility module and/or the defibrillator. The utility module may also provide the device agent with a list of available networks detected by the Wi-Fi module 593 of the utility module for the agent to use in compiling the list of preferred networks that the device agent may send to the utility module instructing the utility module which network to use.

The utility module may also transmit and receive data from adjunct medical device 850 over communication link 801 as shown in FIG. 14. In this illustrative embodiment, the adjunct medical data is transmitted to the utility module through the utility connect 600, which is illustratively a USB connector in this example.

The utility module may also transmit and receive data from other applications over a communication link, which may be one of the wired or wireless communication links illustrated in FIG. 14 or other wired or wireless communication link established by the utility module. In addition, the system advantageously provides for the bidirectional flow of data between the one or more external devices and one or more other external devices with the utility module acting as a proxy for the source of the data. For example, information from the adjunct medical device may be passed over to the utility module through communication link 801; through the utility module; and then passed over to the server 810 through communication link 803.

Figure 15:
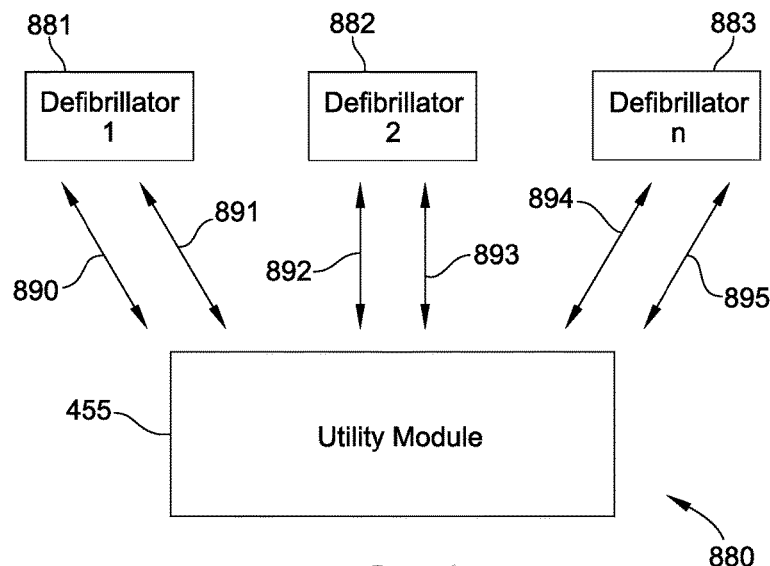
FIG. 15 shows a plurality of defibrillators that may be electrically connected to a utility module of FIG. 4 of this disclosure to provide data communication links and power links between the defibrillators and the utility module in order to enable the utility module to coach a plurality of defibrillators contemporaneously.

In addition, the system advantageously provides for the bidirectional flow of data between a plurality of defibrillator devices and the utility module. As shown in FIG. 15, in an illustrative defibrillator system 880, a plurality of defibrillators 881, 882, 883, may be electrically connected to a utility module 455 to provide the data communication links 890, 892, 894 of defibrillators 881, 882, 883, respectively, as well as the power links 891, 893, 895 of defibrillators 881, 882, 883, respectively, in order to enable the utility module to coach a plurality of devices contemporaneously.

Hence this disclosure enables bidirectional communication between the utility module and the defibrillator device; between the defibrillator and one or more of the server 810, the utility applications (e.g., device agent or other applications), and the adjunct medical device, and/or other external devices and/or programs; between the utility module and one or more of the server 810, the utility applications (e.g., device agent or other applications), the adjunct medical device 850, and/or other external devices and/or programs; between external devices and other external devices through the utility module acting as a proxy for the device that is the source of the data; and a plurality of defibrillator devices and the utility module.

In addition, the defibrillator system 800 shown in FIG. 14 expands the coaching capabilities of the FIG. 4, 5 defibrillator system 400 even further by advantageously enabling one or more devices external to the utility module that are part of the network 870 to communicate between themselves for the purpose of educating the network so that more informed support may be brought to the user of the defibrillator through the utility module. For example, as shown in FIG. 14, the server 810 may be configured for bidirectional communication with the device agent 820 over data communication link 805. As one example, the server may communicate device and utility module software setup information to the device agent which the device agent may then download to the utility module for configuring the settings and downloading software to the utility module or the defibrillator. As another example, the device agent may communicate device and utility module enrollment information to the server 810 which the server may then use to determine which software to download to the device agent.

Figure 16:
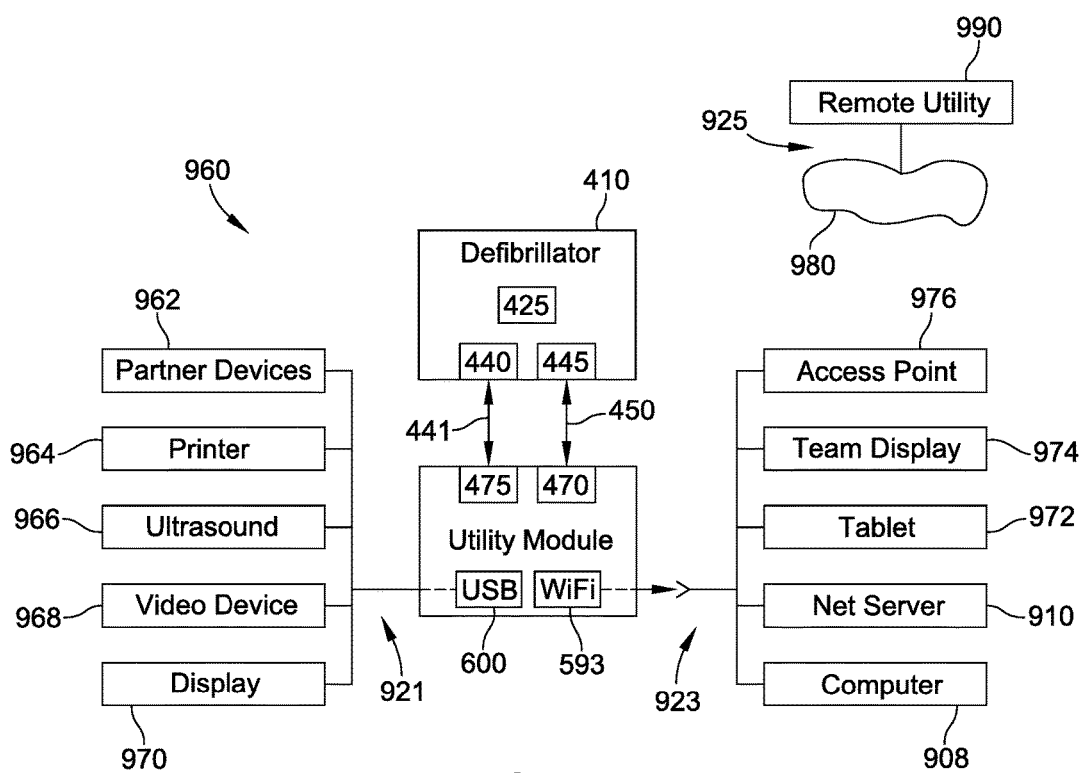
FIG. 16 shows an illustrative range of services that a network may provide the utility module in supporting the user of the defibrillator in the defibrillator system of FIG. 14.

FIG. 16 shows an illustrative range of services 960 that the network may provide the utility module in supporting the user of the defibrillator. FIG. 16 shows defibrillator data connect port 440 of defibrillator 410 received by data outlet 475 of utility module to enable bidirectional data communication between the defibrillator and the utility module over data communication link 441 as discussed in FIGS. 4 and 5. Power connect 445 of the defibrillator is also received by power outlet 470 of the utility module to allow power 450 to be made available from the utility module for powering the defibrillator or for other shared power purposes as also discussed in FIGS. 4 and 5. FIG. 16 further shows utility connect 600, which is a USB connector in this illustrative embodiment, connected with a display 970, a video device 968, an ultrasound device 966, a printer 964, and partner devices 962. Each of display 970, video device 468, ultrasound 960, printer 964, and partner devices 962 provide an additional service to the utility module. For example, the video device 968 enables a user of the defibrillator to take photos or video streams of data of the patient throughout the defibrillation process so that the condition of the patient may be recorded throughout defibrillation for use in connection with the defibrillation or for some post-defibrillation purpose, such as for use by medical professionals in providing post-defibrillation treatment or for use by coaches on the network in providing more effective coaching services going forward.

As another example, the ultrasound 966 enables the user to take ultrasound measurements of a patient during the defibrillation process to provide imaging information of the internal structure of a patient during defibrillation or for use in post-defibrillation medical treatment or coaching applications. The display 970 may allow a monitor, for instance, to be connected to the utility module to allow for a broader or easier viewing of information that is either being displayed on the display of the defibrillator; is being generated by the utility module and not displayed on the defibrillator display; is generated by a device external to the utility module that is part of the network supporting the utility module and is providing coaching to the user of the defibrillator; or other information. The display 970 may provide a supplemental display to the display that may be available on the defibrillator and/or utility module or display 970 may provide the only display available to the user of the utility module and/or the defibrillator. The display 970 may allow more people to view the defibrillation process. It may also allow people who are using the defibrillator and/or the utility module to view a larger screen than may be available on the utility module or defibrillator As illustrated in FIG. 16, the display 970, video device 968, ultrasound 966, printer 964, and partner devices 962 are connected to the utility module to provide bidirectional data communication over data communication link 921 via utility connect 600, which is illustratively a USB connector port in this illustrative example. It will be appreciated that these functions could also be provided to the utility module through any other wired connection or through a wireless connection according to this disclosure. The foregoing list of devices that may be connected with the utility module are illustrative only. It will be appreciated that any other device may be tethered to the utility module to provide the utility module with additional functionality for use by the user of the defibrillator during a defibrillation procedure FIG. 16 further shows further functionality that the network may provide the utility module in supporting the user of the defibrillator in this case through Wi-Fi module 593. It will be appreciated that these functions could also be provided to the utility module through a wired connection. As illustrated in FIG. 16, the Wi-Fi module 593 enables wireless communication over data communication link 923 between the utility module and a computer 908, a Net server 910, a tablet 974, a team display 974, and an access point 976. The server 910 has been previously described in connection with FIG. 14 which description is applicable to the use of the server in the illustrative embodiment of FIG. 16. The tablet is an example of a mobile computing device in the form of a tablet that may wirelessly communicate with the utility module via Wi-Fi module 593 of the utility module. Alternatively, any mobile computing device may be used in place of or in addition to the tablet, including a laptop computer, a smart phone, or any mobile computing device. These mobile computing devices may allow medical professionals and others to communicate with the utility module and with each other as a part of the network in providing assisted coaching to the user of the defibrillator through the utility module of this disclosure. Team display 994 may be a monitor or a flat screen TV; and is illustratively a large flat screen TV that allows groups of professionals to observe data provided by the utility module or by another network device for the purpose of coaching the user of the defibrillator through the utility module of this disclosure.

The wired and wireless bidirectional data communication links between utility module and the network illustratively such as made possible by data communication link 921 and data communication link 923 may further be used to provide data from the defibrillator and/or the utility module to the network as previously discussed. For example, the parameter module 460 configured to detect a parameter of a patient as previously described in connection with FIG. 4 may transmit patient data by hardwire, such as over the data communication link 921, or wirelessly to the display 970 or other local secondary display. Similarly, this data may be transmitted wirelessly, such as over data communication link 923, or by hardwire to team display 974 or another local secondary display. In addition, this data may be transmitted wirelessly, such as over data communication link 923, or by hardwire through access point 976 to a remotely located display. Hence, data from the utility module and/or defibrillator may be pushed out to local or remote resources for use in providing coaching feedback, education, or other purposes.

In the previous examples of devices that are in communication with the Wi-Fi module 593, the communication may be a local area network communication connection such as including well known point-to-point communication methodologies and standards. The access point 976 shown in FIG. 16 illustrates a way of even further broadening the reach of the network that is supporting the utility module in coaching a user of the defibrillator. Communications between the Wi-Fi module 593 and the access point 976 may be over a communication link 925 in accordance with the 802.11 standards or may occur by other wireless methods that allow for the network supporting the defibrillator and utility module of this disclosure to broaden out even further to include public networks and other private networks. In effect, the access point 976 enables the utility module to reach through cloud 980 for the purpose of accessing any remote utility 990 in any public or private network that may be useful to the utility module in providing coaching to the user of the defibrillator. This feature arms the disclosed utility module with even more network resources for providing even more effective coaching of the user of the defibrillator. The foregoing communications may occur contemporaneously during a defibrillation process or may occur after the defibrillation for the purpose of post-defibrillation medical treatment or use in teaching the network how to provide more effective coaching in the future, or for asset management purposes.

Figure 17:
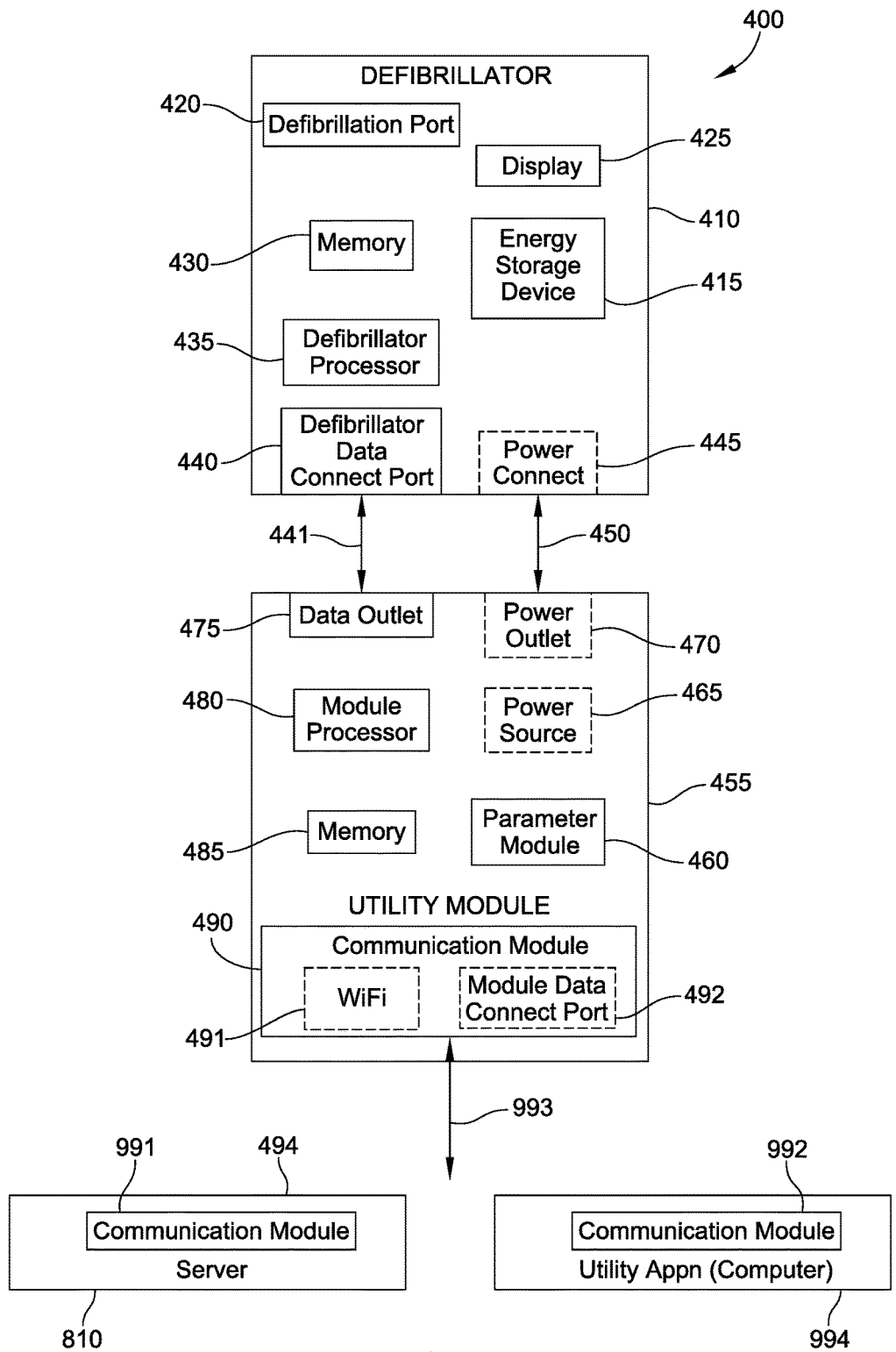
FIG. 17 illustrates the defibrillator system of FIG. 4 configured to create a bidirectional communication link with each of a server and an event agent/application computer.

FIG. 17 illustrates the defibrillator system of FIG. 4 but configured to create a bidirectional communication link 993 with each of a server 810 and utility application (computer) 994. The defibrillator 410 components of defibrillator port 420, energy storage device 415, defibrillator processor 435, memory 430, defibrillator data connect port 440, and power connect 445; as well as the utility module 445 components of a module processor 480, a memory 485, a communication module 490, a parameter module 460, a power source 465, and a power outlet 470 are the same in description and operation as like number components in FIG. 4. The utility module components of Wi-Fi module 491 and module data connect port 492 are the same in description and operation as like numbered components in FIG. 5 The server 810 is the same in operation and description as like numbered component in FIG. 14. Utility application (computer) 994 is an application on a computer that is configured to schedule the triggering of downloading data, such as patient data, from the defibrillator using the utility monitor as a proxy and is described in detail later below. Each of the server 810 and the utility application (computer) 994 includes a communication module 991 and 992, respectively, which are identical in description and function to the communication module 490 of FIG. 4 and which provides one terminal end for the data communication link 993, the other end of the data communication link 493 formed by the communication module 490 of the utility module. In FIG. 14, the server 810 is shown connected to the utility module wirelessly whereas the device agent 820 is shown communicating with the utility module by wired connection. FIG. 17 illustrates that the server and another computer with a utility application (computer) 994 in the example, may be connected wirelessly or by wired connection. The operation of the server and event agent/appln computer are discussed further later below.

Figure 18:
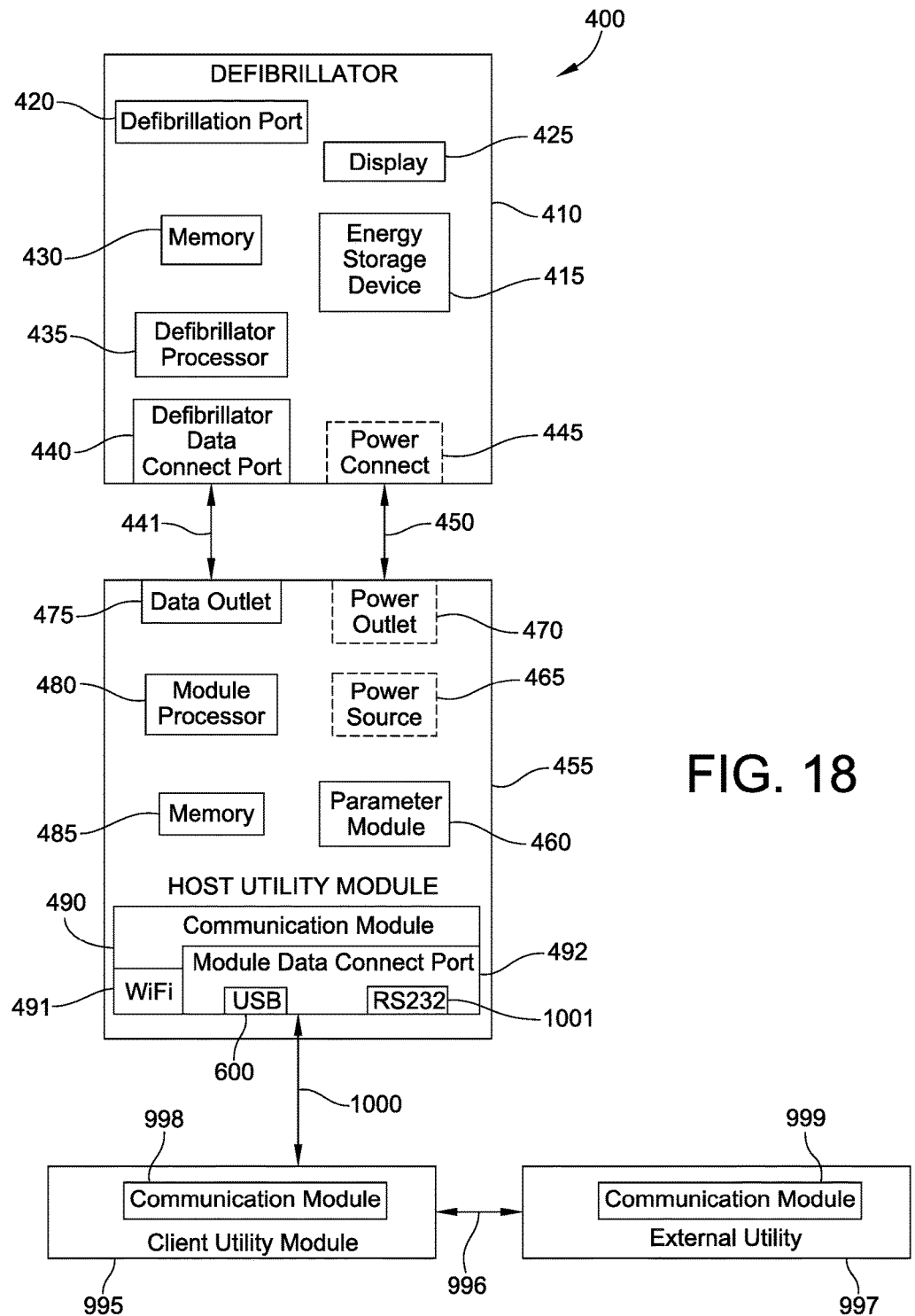
FIG. 18 illustrates the defibrillator system of FIG. 4 configured to create a bidirectional communication link between the utility module and an external client utility module and a bidirectional communication link between the client utility module and an external utility.

FIG. 18 illustrates the defibrillator system of FIG. 4 but configured to create a bidirectional data communication link 1000 between the utility module 455(configured to operate as a host utility module in this case) and a client utility module 995 and a bidirectional data communication link 996 between the client utility module and an external utility 997. The defibrillator 410 components of defibrillator port 420, energy storage device 415, defibrillator processor 435, memory 430, defibrillator data connect port 440, and power connect 445; as well as the utility module 445 components of a module processor 480, a memory 485, a communication module 490, a parameter module 460, a power source 465, and a power outlet 470 are the same in description and operation as like number components in FIG. 4. The utility module components of Wi-Fi module 491, module data connect port 492, utility connect 600 (configured as a USB in this case), is the same in description and operation as like utility connect 600 in FIG. 5. RS232 connect 1001 is a data outlet configured to operate according to the RS232 standard. Client utility module is a program on a computer that is configured to act as a client for the utility module 455. External utility 997 is a program on a computer that is configured to provide some utility function to the host utility module or the client utility module. Each of the client utility module 995 and the external utility 997 illustratively includes a communication module 998 and 999, respectively, which are identical in description and function to the communication module 490 of FIG. 4 and which provides one terminal end for the data communication links, the other end of the data communication links being provided by a data communication link found in the device to which it is connected. The foregoing further demonstrates the ease with which the utility module may be connected to external devices through direct or indirect data communication links in order to facilitate the coaching by the network of a user of the defibrillator. It will be appreciated that each of the client utility module 995 and/or the external utility 997 may be configured to be connected to each other in other ways including through a direct power link provided between these or other external devices and the utility module.

In FIG. 18, the client utility module 995 is denoted as the "client" and the utility module 455 as the "host" since the client is performing calculations for use by the host in this example.

Figure 19:
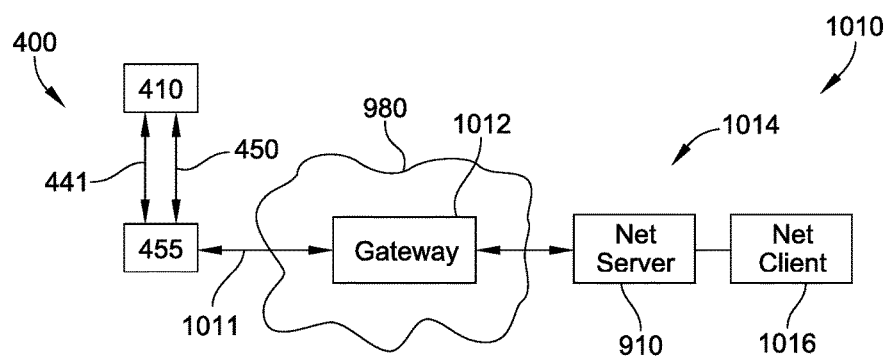
FIG. 19 illustrates the use of a utility module of FIG. 4 of a defibrillator system 400 in engaging a network comprising a server and a client in connection with coaching a user of the defibrillator.

FIG. 19 illustrates a defibrillator system 1010 comprising the use defibrillator system 400 of utility module 455 defibrillator 410 of FIG. 5 and a network 1014 comprising a netserver 910 (in like description and operation as net server 910 in FIG. 16) and a net client 1016 for coaching a user of the defibrillator. In FIG. 19, the utility module is in data communication with the defibrillator over data communication link 441 and in power communication with the defibrillator over power link 450 in a manner previously described. In this example, the server net 910 and net client are in a private network 1014 and the utility module 455 is outside that private network. FIG. 19 shows that the utility module 455 may establish communication with server 910 and client 1016 by going through cloud 980 (in like description and operation as cloud 980 in FIG. 16). In this example, the private network 1014 is provided with a gateway 1012 to the cloud 980. The gateway provides a public portal to the private network that is physically addressable and hence reachable from the public network. In this example, the utility module reaches the server 910 by addressing the gateway 1012 to the private network 1014. The utility module may reach the gateway through a Wi-Fi access port such as shown in FIG. 16. Alternatively, the utility module may reach the gateway using WAN or using other communication technologies. The gateway may validate the utility module and then switch the data communication link 1011 that has been established between the gateway and the utility module over to the server 910 which is connected to the client 1016. This enables the client to communicate with the utility module and the defibrillator in order to provide more robust coaching to the user of the defibrillator.

The network 1014 may support transmission of relevant patient data from the defibrillator 410 in the field to emergency departments, cardiac catherization labs, and other cardiac care locations to enable prompt and optimal diagnosis and treatment or appropriate post-review of the data by qualified medical personal. The network 1014 also enables organizations to manage their material assets and provides tools for remote physician consultation through the use of network consulting application.

Network 1014 may also provide event patient reports and data. Any report or data transaction that occurs during a patient monitoring or therapy event may be transmitted by the utility module 455 to the net server 910. The patient event data may assist qualified medical personnel in making accurate diagnosis, disposition, and therapy decisions. Event patient reports created by a defibrillator may be transferred through utility module 455 to the net server 910. The netserver 910 may be in a private network or a public network. If the net server 910 is in a public network, the net PC gateway 1012 may be used for the utility module to reach the network in which net server 910 resides as previously described. Through the net PC gateway, the utility module may establish bidirectional data communication with the net server for the purpose of transmitting patient event data from the defibrillator to the net server from which third party monitoring devices may retrieve the data and communicate with the defibrillator for the purpose of coaching the user of the defibrillator.

The net server may also enable reports to be generated from the data taken from the patient event and transmitted as needed after the event. This information may be useful in post-event analysis to support post-event medical treatment. For example, non-real-time data transfers of ePCR reports may be used in post-event analysis to document the treatment, patient state, and diagnosis provided by pre-hospital care providers. This information may also be useful as data for use in post-event training of medical professionals in order to train medical professionals to provide better coaching in connection with future events.

Figure 20:
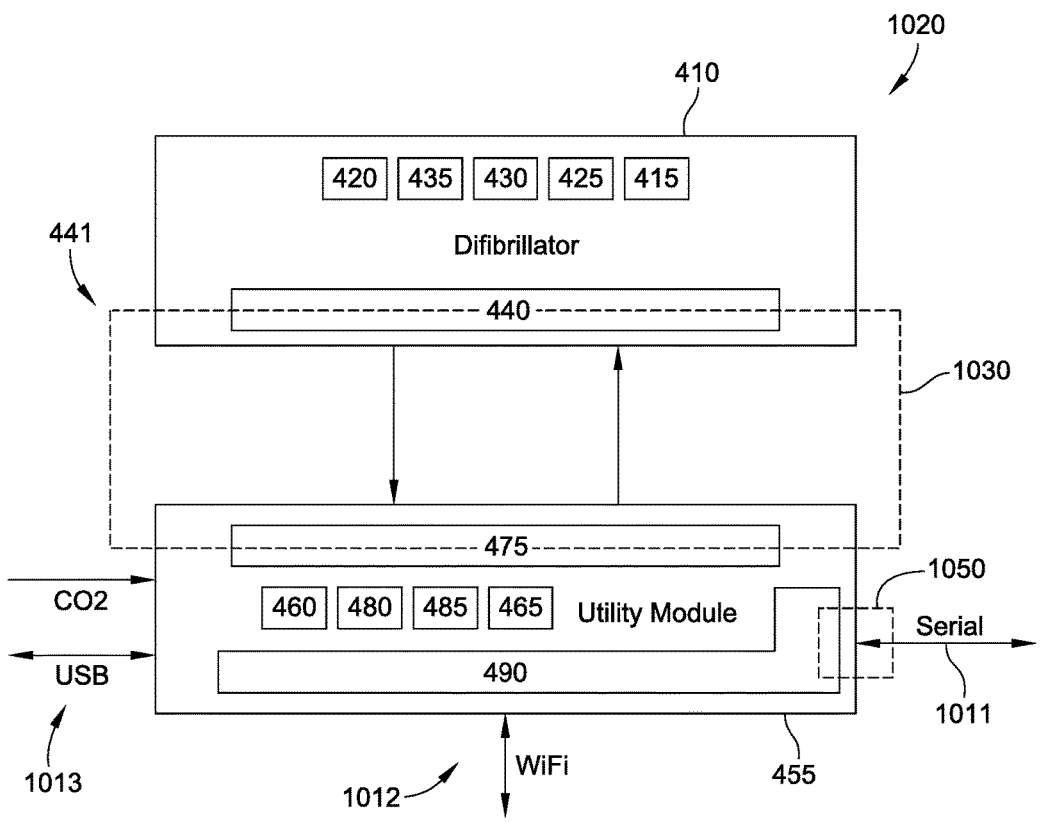
FIG. 20 shows an illustrative data communication system of this disclosure comprising a data interface for enabling communication between a utility module of FIG. 5 and a defibrillator and a serial interface for enabling communication between the utility module and external devices.

FIG. 20 shows an illustrative data communication system 1020 of this disclosure comprising a data interface 1030 for communication between the utility module 455 and the defibrillator 410 and a serial interface 1050 for communication between the utility module 455 and external devices (not shown). The defibrillator 410 components of defibrillator port 420, energy storage device 415, defibrillator processor 435, memory 430, and a defibrillator data connect port 440; as well as the utility module 445 components of a module processor 480, a memory 4485, a communication module 490, a parameter module 460, and a power source 465, are the same in description and operation as like number components in FIG. 4. As shown in FIG. 20, the bidirectional flow of data between the defibrillator 410 and the utility module 455 occurs across interface 1030 and includes test interface commands, patient episode data, device self test status, $CO_2$ waveform, vital signs, device status, data transfer status, and vital signs. Interface 1030 is the hardware and software architecture that enables the bidirectional data flow, as described in FIG. 4, across the data communication link 441 between the defibrillator and the utility module through the data outlet 475 of the utility module and the defibrillator data connect port 440 of the defibrillator. Before describing more about the bidirectional data flow of data and the illustrative data and commands that may be included in that data flow, it is important to describe the illustrative architecture that may make up interface 1030.

Figure 21:
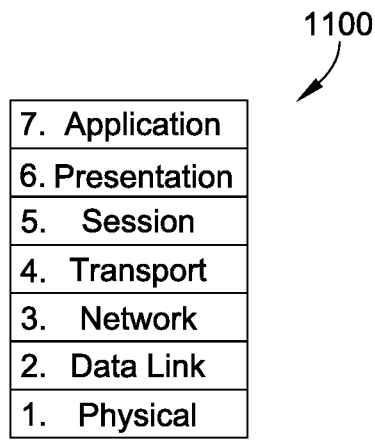
FIG. 21 shows a standard OSI module that may be used as described in this disclosure to provide the data interface of FIG. 20 of this disclosure.

FIG. 21 shows a standard OSI module that may be used as described below to provide interface 1010 of this disclosure. The illustrative architecture is portrayed using the 7-layer open systems interconnection (OSI) model. The OSI model defines a networking framework for implementing protocols in seven layers and is well known in the art. Control is passed from one layer to the next, starting at the application layer in one station, and proceeding to the bottom layer, over the channel to the next station and back up the hierarchy.

As shown in FIG. 21, interface 1010 (FIG. 20) illustratively comprises a physical layer, a data link layer, a network layer, a transport layer, and an application layer. Alternatively, the interface 1110 may further include a session layer and a presentation layer although these layers are not included in the illustrative embodiment.

Illustratively, the Physical Layer 1 of interface 1010 (FIG. 20) is illustratively an RS-X hardware defined by data outlet 475 (FIG. 4) which receives the defibrillator data connect port 440 (FIG. 4) of the defibrillator 410 to complete the hardware connection between the defibrillator and the utility module. The RS-X hardware conveys the bit stream between the defibrillator and the utility module through the network at the electrical and mechanical level in accordance with the RS232 protocol. Illustratively, the bit stream is an electrical bit stream. Alternatively, a bit stream of light, radio signals, or other data streams may be used with this disclosure. Hence, in the disclosure of FIG. 21, the RS-X hardware provides the means for sending and receiving data by electrical signals between the utility module and the defibrillator, with the data outlet 475 and defibrillator connect port 440 defining the cables, cards and physical aspects of that physical layer connection. While interface is illustratively RS-X hardware, it will be appreciated that ISTN, ADSL, ATM, FDDI, CAT 1-5, coaxial cables, and other protocols with physical layer components may be used to provide the bidirectional data flow in the interface enabling the data communication link 441 of this disclosure.

Referring again to FIG. 21, illustratively, Data Link Layer (2), is illustratively an SLIP PPP protocol for encoding and decoding the data packets into bits as described by the Point-to-Point Protocol ("PPP") known as RFC 1661 as extended by RFC 1570 (PPP LCP Extensions). Alternatively, the data link layer 2 may include RFC 1661 updates such as RFC 2153 (vendor specific packets) and RFC 5342 (IANA considerations and IETF protocol usage for IEEE 802 parameters). The PPP 1162 protocol furnishes transmission protocol knowledge and management and handles errors in the physical layer, flow control and frame synchronization. The data link layer is divided into two sub layers: The Media Access Control (MAC) layer (not shown) and the Logical Link Control (LLC) layer (not shown). The MAC sub layer controls how the defibrillator and the utility module in the defibrillator system of this disclosure gains access to the data and permission to transmit it. The LLC layer controls frame synchronization, flow control and error checking.

Figure 22:
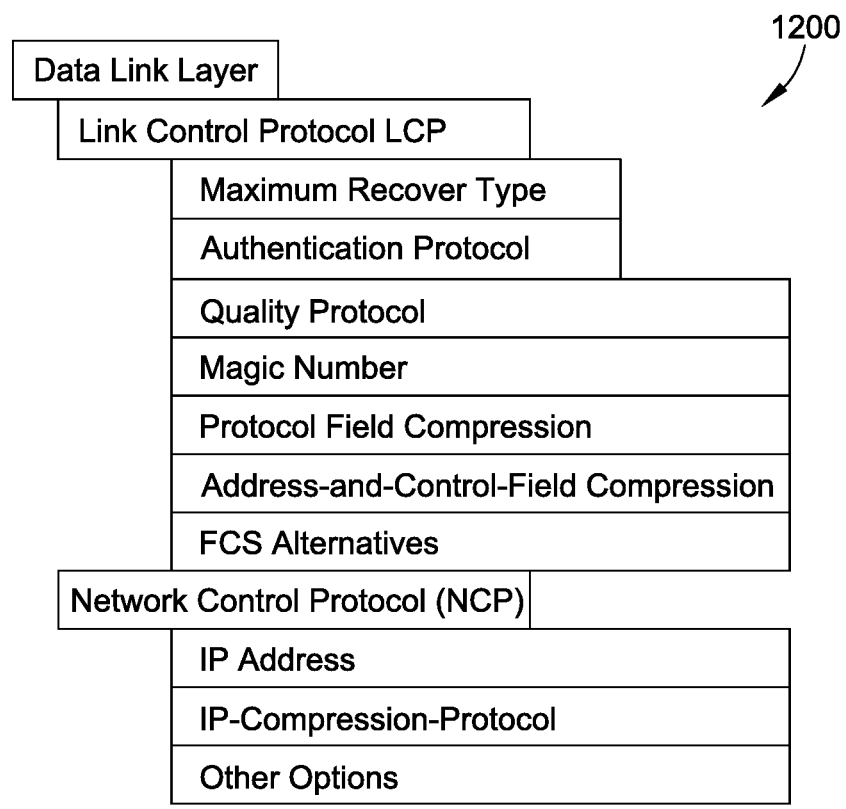
FIG. 22 illustrates a PPP Protocol for the Data Link Layer according to this invention.

Referring to FIG. 22, the PPP Protocol 1200 of the Data Link Layer will more specifically illustratively include a Link Control Protocol (LCP) and a network control protocol (NCP). The PPP LCP is configured for setting up, maintaining, and terminating the link between devices such as the defibrillator and the utility module and between the utility module and an external device when the utility module is acting as proxy for the external device in connection with communications between the external device and the defibrillator. The LCP may be configured with one or more of the following or other options: maximum receive type option; authentication protocol option; quality protocol option; magic number option; protocol field compression option; address-and-control-field compression option; and FCS alternatives option.

The Maximum-Receive-Unit is illustratively set to allow for extension of the use of the utility module with a wide number of devices. The Authentication-Protocol (type 3) is illustratively an authentication used to prevent unauthorized connections to the defibrillator and the utility module. Illustratively, the authentication protocol is based on RFC 1661. RFC 1661 identifies two protocols (PAP (RFC 1334) and CHAP (RFC)) for providing authentication of a connecting device. PAP is a simple request/reply authentication protocol. The PAP provides very little protection against many security risks, but may be sufficient for the connection between the defibrillator and the utility module and so illustratively is used. Alternatively, the CHAP may be used to authentication the connection of the devices.

Referring still to FIG. 22, the Quality-Protocol option may be a type 4 quality protocol. Illustratively, the link quality monitoring feature is disabled by default. Alternatively, the protocol may be enabled to provide quality monitoring. Magic-Number option is a type 5 is illustrative not negotiated and is not used in the illustrative defibrillator to utility module connection. The Protocol-Field-Compression option is a type 7 protocol field compression. Compression may be utilized to optimize available bandwidth.

Address-and-Control-Field-Compression option is illustratively a type 8 address and control field compression.

Still referring to FIG. 22, Network Control Protocol (NCP) supports the encapsulation of many different layer three datagram types. Some of these require additional setup before the link can be activated. After the general link setup is completed with LCP, control is passed to the PPP NCP specific to the layer three protocol being used on the PPP link. As IP at the network layer level is used over the PPP connection, Internet Protocol Control Protocol (IPCP (RFC 1332)) is used as the NCP. The link will remain configured explicit LCP or NCP packets close the link down, or some external event occurs (such as holding CTS low, or some inactivity timer expires).

Alternatively, the Network Control Protocol may include an IP-Address of type 3; an IP-Compression-Protocol of type 2; and Other Options 1233 such as DNS Server could also be used; albeit in the above indicated example, these features are not used The data transmission speeds of LCP and NCP may be determined by restart timers (not shown) which may be used to set and change the data transfer speed between the defibrillator and the utility module for itself or as proxy to an external device.

Figure 23:
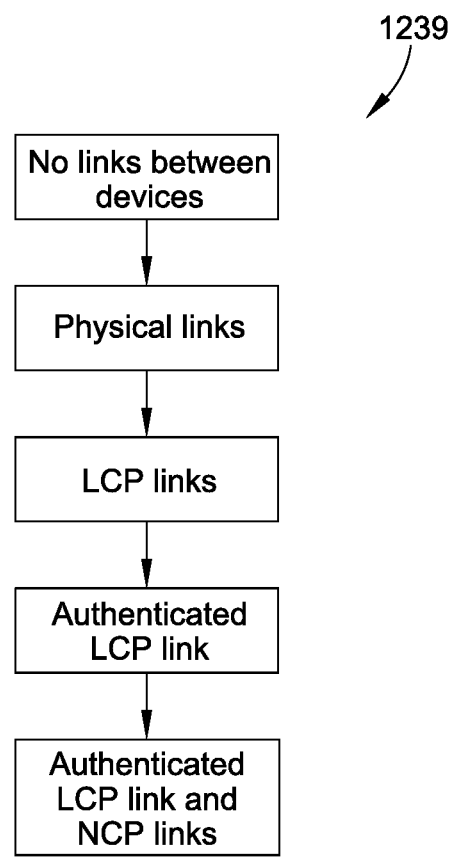
FIG. 23 shows a process by which the PPP LCP of the PPP Protocol of FIG. 22 may be configured for setting up, maintaining, and terminating the link between devices such as the defibrillator and the utility module and between the utility module and an external device when the utility module is acting as proxy for the external device in connection with communications between the external device and the defibrillator.

FIG. 23 shows a process for configuring PPP LCP 1239 for setting up, maintaining, and terminating the link between devices such as the defibrillator and the utility module and between the utility module and an external device when the utility module is acting as proxy for the external device in connection with communications between the external device and the defibrillator. At the start of the process, there are no communication links established between the utility module and the defibrillator. At this point, the PPP LCP process 1239 detects the existence of no links between the utility module and the defibrillator (i.e., link dead). When the data outlet 495 (see FIG. 4) receives defibrillator data connect port 440 (see FIG. 4), the PPP LCP process 1239 detects the physical connection between the defibrillator and the utility module and the PCP LCP protocol attempts to establish a communication link between the defibrillator and the utility module. If the PCP LCP protocol is unsuccessful in establishing the communication link between the defibrillator and the utility module, the PCP LCP protocol returns to the link dead state to again wait to detect the physical connection between the defibrillator and the utility module. If the PCP LCP protocol is successful in establishing the communication link between the defibrillator and the utility module, the PCP LCP protocol advances to a step of establishing the communication link between the defibrillator and the utility module. This step is shown as a link established in the physical layer. In the PCP LCP process 1239, the PCP LCP advances to the step of authenticating the particular defibrillator as a device that is authorized to be used with the particular utility module and vice-versa (i.e., authenticating that the particular utility module is authorized to be used with the particular defibrillator.) If the PCP LCP fails to authenticate that the defibrillator and the utility module are authorized to be used with each other, the PCP LCP process 1239 advances to a link termination step whereby the PCP LCP proceeds to terminate the LCP link. This step is shown as LCP link. If the PCP LCP process successfully authenticates the use of the defibrillator and the utility module with each other (or if no authentication is required), the PCP LCP process 1239 advances to the network layer protocol. The step of successful authentication is shown as an authenticated LCP link. The PCP LCP process then advances to negotiate a successful NCP configuration. If unsuccessful, the PCP LSP process 1239 terminates the link. If the NCP configuration is successfully negotiated, the process 1239 advances to an open link. In the process 1239, the negotiation of NCP configuration is shown as authenticated LCP link and NCP links.

Referring again to FIG. 21, illustratively, Network Layer 3 is illustratively Internet protocol version 4 for providing switching and routing technologies, creating logical paths, known as virtual circuits, for transmitting data from node to node in networks. Routing and forwarding are functions of this layer, as well as addressing, internetworking, error handling, congestion control and packet sequencing are well known in the art. More specifically, the network layer interface between defibrillator and the utility module is the Internet Protocol (IP or IPv4) as described by RFC 791. It is responsible for logical device addressing, data packaging, manipulation, and delivery and routing. In addition, the network layer interface may include ICMP (Internet Control Message Protocol; RFC 792) as an integral part of IP. It is typically used to send error messages such as when a datagram cannot reach its destination. In an illustrative peer-to-peer embodiment, the ICMP is not used. However, in alternative embodiments of peer-to-peer and otherwise, the ICMP may be useful in providing message control for communications. The IP header includes a number of items including the source and destination addresses. The defibrillator will illustrative utilize a unique IP address. The utility module will utilize another unique IP address. Both of these addresses are illustratively within the block of IP addresses reserved for private internets per RFC 1918.

Transport Layer 4 is illustratively a transmission protocol (TCP) for providing transparent transfer of data between end systems, or hosts. TCP is responsible for end-to-end error recovery and flow control and ensuring complete data transfer and is well known in the art. More specifically, Transport Layer (4) between the defibrillator and the utility module will be Transmission Control Protocol (TCP) as described by RFC 793. It is used to guarantee the delivery of the message or entire files. TCP assumes that an IP protocol is available at the lower levels of the communication stack. Illustratively, the FTP utilizes TCP to guarantee the delivery of entire files.

Session Layer 5 and Presentation Layer 6 are illustratively not used in the illustrative embodiment. Alternatively, Session Layer 5 and Presentation Layer 6 may be used on alternative embodiments. The Session Layer 5 establishes, manages and terminates connections between applications. The session layer sets up, coordinates, and terminates conversations, exchanges, and dialogues between the applications at each end and deals with session and connection coordination. The Presentation Layer 6, sometimes called the syntax layer, provides independence from differences in data representation (e.g., encryption) by translating from application to network format, and vice versa. The presentation layer works to transform data into the form that the application layer can accept and formats and encrypts data to be sent across a network, providing freedom from compatibility problems. Both Session Layer 5 and Presentation Layer 6 are well known in the art.

Application Layer 7 supports application and end-user processes. Application layers may include applications for e-mail, news-groups, web applications, file transfer, host sessions, directory services, network management, file services, and other network services. These applications identify communication partners, quality of service, user authentication and privacy, and any constraints on data syntax. This layer of application-specific and end user processes is well known in the art.

More specifically with respect to Application Layer (7) in the illustrative embodiment, the defibrillator and the utility module illustratively communicate in normal mode data via sockets—except when the device is passing through test interface commands—and the utility module will pull stored patient data and device test reports via FTP. FTP is described by RFC 959 (updated by 2228 (FTP Security Extensions), 2640 (Internationalization of the File Transfer Protocol)). RFC 2773 (Encryption using KEA and SKIPJACK) is not used in the illustrative embodiment but may be used in alternative embodiments to provide more encryption functionality.

Illustratively, FTP is used only to retrieve patient and device records when the defibrillator is not actively being used on a patient. In the FTP protocol configuration, the defibrillator is configured to act as the FTP server, and utilizes a username and a password for access control. Supported FTP commands are listed in the FTP protocol. Illustratively, commands may include commands to read or access data or to create or delete directories and files may be utilized or supported. The utility module may retrieve the current content of the attached defibrillator through commands that determine which files/records to retrieve including device test logs and patient records.

If the defibrillator transitions from a normal mode into an archives mode, then the utility module may repeatedly issue commands looking for a request to send a patient record denoted by content in an outbox element. The defibrillator may identify files that it wants to transmit (if any) by populating an outbox element. The utility module may retrieve the indicated record(s) through commands. After an outbox file is retrieved, the defibrillator may remove it from subsequent directory objects.

If the defibrillator startup reason is in a self test and the self test is complete, the utility module may retrieve the directory of unsent records by getting the directory object. The utility module may utilize the content of the directory object to successively retrieve the continuous ECG and code summary records for each unsent patient record (as noted by a record previously sent record attribute) using FTP commands. After all unsent patient records are retrieved, the utility module may also retrieve the device test log record using an FTP command.

Regardless of the startup reason, after a patient record has been retrieved by the utility module, and the utility module has successfully transmitted the record to an external device, the utility module may transmit commands to the defibrillator to mark a record as being sent. Subsequent directory object contents may indicate that the record has been sent to prevent repeated transmissions. When the defibrillator startup reason is a self test and all unsent records have been retrieved and transmitted to a network system, such as a network server, or when the network system link is no longer available, the utility module may command the device to shutdown through a test interface command.

Sockets are primarily a concept used within the Transport Layer. With the addition of custom data, these become layer-like messages. An IPv4/stream/TCP socket (described by RFC 147) will be created by the utility module to carry bi-directional messages between the defibrillator and the utility module. A predetermined port may illustratively be used. The utility module will act as the server, and will listen for connections. The defibrillator will connect to the socket created by the utility module. After a connection has been established, periodic messages will be exchanged during normal mode as detailed in the following sections.

Message Framing and Encoding. Messages are passed through a TCP based socket which includes its own framing and guaranteed delivery so no additional framing is required. Multiple messages can be sent in a single transmission as the receiver sees the messages as a simple stream of bytes.

Check Value. Although each message is transported by protocols to ensure the integrity of the message, a check value can be used to determine if an invalid message was generated at the source, or corrupted by the receiver after reception.

Message Rates. The Monitoring Mode (CO2 waveform) is illustratively 5 Hz. The overall message rate of the system is driven by the CO2 sample rate. The CO2 module samples waveform data at 20 Hz (i.e., every 50 ms). Hence, illustratively after every 4 samples the utility module CO2 Waveform message (2001) normal mode message is sent from the utility module to the defibrillator (i.e., every 200 ms). If the utility module does not have the CO2 Module or this module has a malfunction, the utility module will send a null message.

FTP Data Transfer Mode. The FTP data transfer mode is illustratively 1 Hz. In FTP Data Transfer Mode, messaging is reduced to 1 hz and message traffic is reduced to increase bandwidth available for FTP data transfers. The utility module Device Data Transfer Status packets are sent at a data rate of 1 hz. The defibrillator illustratively sends Device Status packets at 1 hz.

Figure 24:
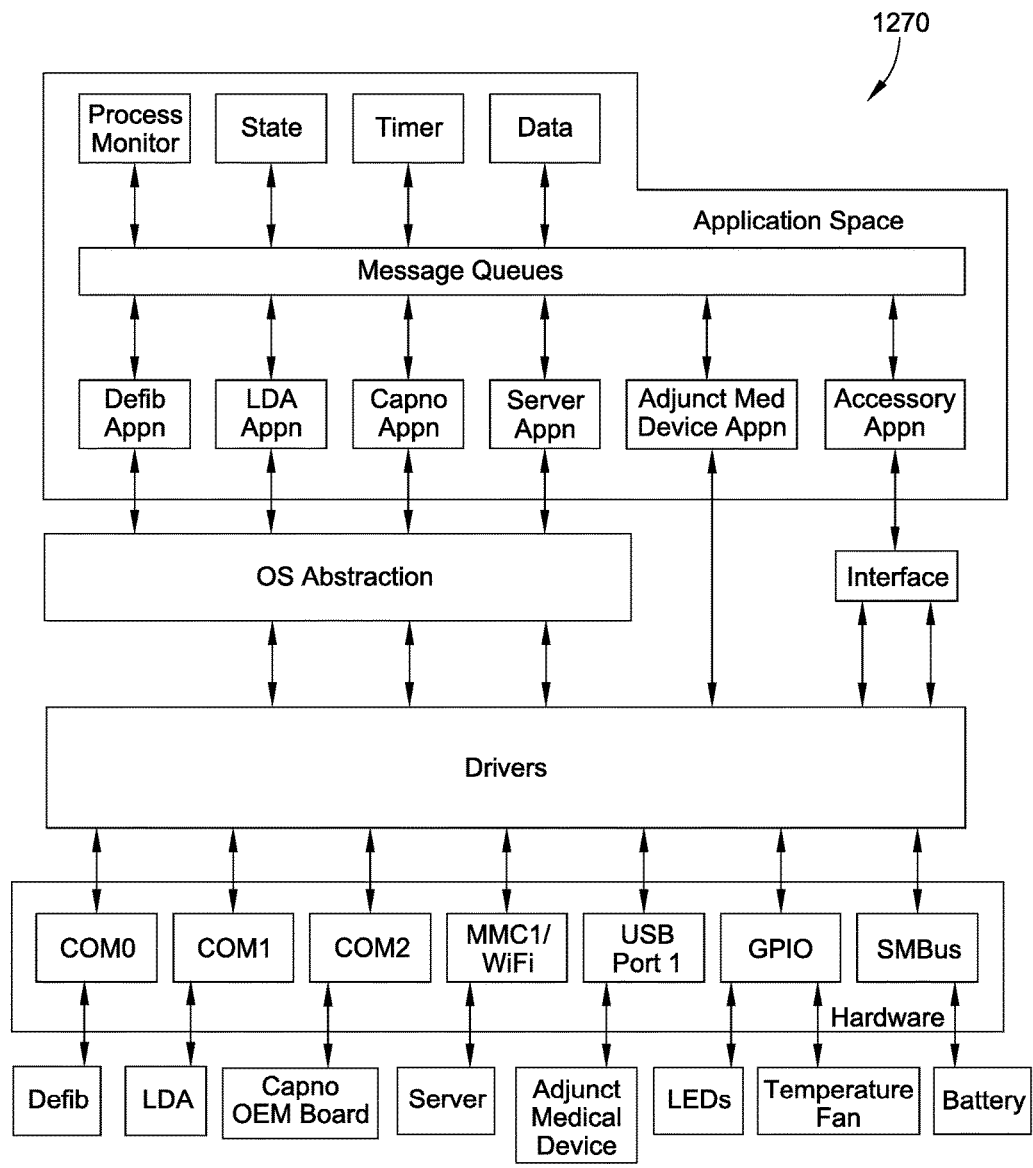
FIG. 24 shows illustrative data links 1270 using the hardware and software architecture 1100 of FIG. 21.

FIG. 24 shows illustrative data links 1270 using the hardware and software architecture 1100 of FIG. 21 of this disclosure. Data links 1270 includes physical layer, data layer, network layer, and application layer. Physical layer includes a data connect COM0; physical connector COM1 to a communication module 490, physical connector COM2 to a capnography module, an MMC17 Wi-Fi connect to a server; a USB PORT 1 to an adjunct medical device; a GPIO connect to LEDS and temperature fan; and an SMBus connect to a battery. These pieces of hardware connect through drivers to an OS abstraction or an interface. The OS Abstraction creates sockets and commands to connect the data to and the intermediary driver also connects data to the application space. The application space comprises a variety of applications such as defibrillator application, LDA application, capno application, server application, adjunct medical device application, accessory application. For instance, the LDA application supports application and end-user processes for the device agent. The server application supports application and end-user processes for the server 910, allowing for the bidirectional exchange of data between socket and message queues.

As discussed in connection with the FIGS. above, an RS232 serial connection is illustratively used for data communications between the utility module and the defibrillator. More specifically, the bidirectional data 441 travels over a hardwire connection that is established once the defibrillator data connect port 440 of the defibrillator is received by the data outlet 475 of the utility module as discussed in FIG. 4. Advantageously, the RS-232 serial connection uses two different protocols during the communication sessions. The utility module initializes its serial port on its power on to provide test interface functionality which is described in connection with FIG. 20 as the test interface commands. The foregoing test interface commands and responses may be used by external devices to communicate with the defibrillator through the utility module at the manufacturing test interface level. In this case, the utility module acts as a pass-through for all test interface commands between an external device and the defibrillator. The test interface commands and responses and the PPP protocol commands can occur contemporaneously. In other words, the foregoing pass-through can occur with the PPP protocol running or without the PPP protocol. The external devices that may initiate and respond to test interface commands may include the device agent, the capnography unit, the server 810, and the adjunct medical device 850 described in connection with FIG. 14. In addition, the utility module may also use the foregoing test interface commands and responses for its own communication with the defibrillator. Hence, the utility module is configured to communicate with the defibrillator for its own purposes as well as to communicate for the external devices by proxy using test interface test interface commands.

To enable a Point-to-Point (PPP) connection between the defibrillator and the utility module, the disclosed hardware and architecture of FIG. 21 advantageously dedicates one or more of the test interface commands to enabling a Point-to-Point (PPP) connection between the defibrillator and the utility module. PPP is used as a data link layer protocol used to support IP network layer connections, TCP transport layer connections and FTP application layer connections. Illustratively, one test interface command is used to initiate a Point-to-Point Protocol (PPP) direct communication in the illustrative disclosure of FIG. 21. Hence, the RS-232 serial communication between the utility module and the defibrillator utilizes test interface commands to both perform test interface level communications between the utility module and the defibrillator and between external devices and the defibrillator through the utility module acting as proxy to the external devices and PPP level communications between the defibrillator and the utility module for use by the utility module itself or as a proxy to one or more external devices.

The PPP command enables the communication between the defibrillator and the utility module for use by the utility module itself or with the utility module acting as proxy to one or more external devices. The data generated by the PPP command is network enabling, that is, useful for communicating over the network. As described in connection with FIG. 20, this network enabling data may include defibrillator device self test status data; utility module data transfer status data; a device status data that each of the utility module and defibrillator, respectively, may send to the other to indicate the status of the device; patient episode data that the defibrillator may send to the utility module; CO2 waveform data that the utility module may send to the defibrillator; and vital signs data that each of the utility module and defibrillator, respectively, may send each other.

As previously discussed, this network enabling data enables these and other network based communications to occur between the defibrillator and the utility module in connection with the exchange of network based data between the defibrillator and the utility module and in connection with the exchange of network based data between the defibrillator and the utility module when acting as proxy for one or more external devices (i.e., for the utility module to pass through to the external devices.)

Referring still to FIG. 20, one network based communication between the defibrillator and the utility module when acting as proxy for one or more external devices may be enabled by the device self test status data which is a command that originates from the defibrillator to the utility module. With the device self test status command, the defibrillator tells the utility module that it is ready to download data that is contained in defibrillator (such as in the memory unit 430 of the defibrillator 410 as shown in FIG. 4) to the utility module for the utility module to store or to pass through as proxy to an external device.

One application that takes advantage of the device self test data is the server application shown in FIG. 24. The server application is shown in FIG. 24 residing in the application space of the hardware and system architecture implementing data links 1270 using the utility module 455 as shown in FIG. 24. Advantageously, the server application may provide an event service that allows for the scheduled downloading of data from the defibrillator for storage in the utility module or for pass-through to an external device through the utility module acting as proxy for the external device. In either case, the utility module processor 480 (FIG. 4) may be configured to execute the instance of the event service provided by the server application shown in FIG. 24 in order to provide data communications from the defibrillator to the utility module or to an external device through the utility module acting as proxy. In one illustrative embodiment, the external device may be the server 810 of FIG. 14. Hence, the event service may be used to enable data communications to pass from the defibrillator to the utility module for use by the utility module or to the external device, through the utility module acting as proxy, for use by the external device.

In the foregoing example, the server event service that enables scheduled downloading of data communications from the defibrillator resides on the utility module as a client. Alternatively, the event service that provides data communications from the utility module may be configured to reside on a computer such as the utility applications (computer) 820 shown in FIG. 14. In either case, this event servicing application providing the instructions for controlling processor 480 of the utility module to download defibrillator data advantageously enables the defibrillator system of this disclosure to provide scheduled downloads of defibrillator data to the utility module or to the external device through the utility module acting as a proxy.

Advantageously, the transmission of the data by the event service that enables data communications from the defibrillator to the utility module to either use or pass through to an external device may occur at a predetermined period of time. The predetermined period of time at which the transmission of data by the event service that provides data communications from the utility module from the defibrillator may illustratively occur substantially at or about 3 o'clock in the morning. Illustratively, the 3 o'clock in the morning time may be based on the time zone in which the defibrillator is being used. This allows the download of data from the defibrillator to occur at a time of the day when the defibrillator is least likely to be used. Where a defibrillator system of this disclosure is being managed across several time zones, the 3 o'clock in the morning time may be based on one of the time zones within that managed region.

While the preferred time of day for the download of data to occur is at or around 3 o'clock in the morning for the reasons previously discussed, it will be appreciated that the predetermined period of time at which the transmission of data by the event service that provides data communications from the utility module from the defibrillator may be other than 3 o'clock in the morning and may also be managed in other ways. For instance, the predetermined period of time at which the transmission of data by the event service that provides data communications from the utility module from the defibrillator may be scheduled to occur once a day. Alternatively, it may be scheduled to occur more than once a day. In addition, it may be scheduled to occur every other day, weekly, or at other regular or irregular periods of time. Where irregular periods of time are used, a random number generator may be used to instruct the event service what time to make the downloads each day. As another example, the predetermined period of time at which the transmission of data by the event service that provides data communications from the utility module from the defibrillator may occur between the hours of midnight and 6 am in the morning. The defibrillator may come from the factory preprogrammed with a specific time for the download to occur. Alternatively, the specific time may be provided to the defibrillator at a later point in time in connection with an update to software or configuration settings. Illustratively, the specific time may be included in rules that may be downloaded to a defibrillator at any time. For instance, a rule may prescribe that the download is to occur at 3 o'clock in the morning unless the defibrillator is being used at that time. If the defibrillator is being used at 3 o'clock in the morning, the rule may prescribe that the download will occur at a predetermined period of time after the defibrillator has last been used. If this programmed predetermined period of time after defibrillator use is one hour and the last activity of the defibrillator is confirmed by the utility module to be 3:27 am, then the foregoing rule would schedule the next download of data one hour later, or at 4:27 am in the morning, on the same day.

As previously indicated, the transmission of the data by the event service that provides data communications from the utility module from the defibrillator may be to a server. Alternatively, it may be to a computer which is not configured to serve other computers. In the event the communication of the downloaded data from the defibrillator is to server 810 as shown in FIG. 14, the download to the server may be within a private network or may occur over the public network such as over the internet. In the case of a download of data over a public network, the transmission may occur through gateway as shown and described in connection with FIG. 19.

Turning now to the operation of the data communication link of the defibrillator system of this disclosure, upon defibrillator and utility module startup or after a controlled reset, the baud rate is illustratively reset to a baseline baud rate. The baseline baud rate will serve as the baud rate for the communications between the defibrillator and the utility module communication and also between both the defibrillator and the utility module and an external device. The utility module will utilize a test interface command to initiate changing the baud rate and the defibrillator will respond, and both the defibrillator and the utility module will switch baud rates. After a short time delay, the utility module will utilize a command to confirm that the baud rate switch has been made. The test interface commands are used by the defibrillator and the utility module and the external devices in initiating and effecting these communications. A defibrillator and utility module is configured to respond to the commands the same way with or without the utility module connected to the defibrillator. To accommodate this, the utility module may act as a pass-through for all existing test interface commands—this can occur with the PPP protocol running or without the PPP protocol running. In this embodiment, the utility module will intercept new commands, as well as other commands normally intended for the defibrillator.

On power up, the defibrillator sends an ASCII banner over the test interface. Following receipt of the banner, the utility module can use test interface commands to request information it needs from the defibrillator. The utility module may respond to the banner by sending the open and external commands. Depending upon the utility module operating mode, various other commands may be issued. For example, the communications baud rate will be changed using a specific command, and a normal mode communications session will be established using a utility module initiate command. Additional defibrillator and utility module commands may be used.

Intercepted Test Interface Commands. The utility module contains an external serial port that is intended to replicate the functionality of the defibrillator's external serial port. This serial port may be used by external components and programs such as the utility applications (computer) 820 (FIG. 14) that includes a device agent to communicate with and control the defibrillator and utility module. All commands from an external device except those described below will be passed through to the defibrillator device for handling when the device is in normal mode and the utility module is not utilizing the test interface of the device. For example, with a specified external device command, the utility module will intercept the external command, and respond that the test interface is now accessible. The utility module will respond to subsequent external commands with an error message. With the baud rate select command (except as noted later), the utility module will respond to the external program as if the defibrillator was responding and change its communication rate on the external serial port accordingly. With a reboot command, the utility module will pass the reboot command through to the defibrillator, but in addition the utility module will reset its external baud rate. The utility module will respond to external commands when utility module is utilizing the test interface command with a message that the external device command is not accepted. The utility module will transmit a command prompt on the external serial port whenever it receives a banner from the defibrillator on its internal serial port Pass-Through Operation. There is a need for the utility module to quickly pass-through test interface commands from an external device to the defibrillator without interference (for example, when performing a software load through the utility module). To accomplish this, when the utility module receives an open command on the external serial port and the defibrillator is powered on, the utility module will stop responding to the utility module command and send a stop command to the defibrillator so that defibrillator also stops sending the utility module command. The defibrillator will respond to the utility module with a command prompt. Upon receipt of the command prompt, the utility module will transmit the opened response on the external serial port.

Figure 25:
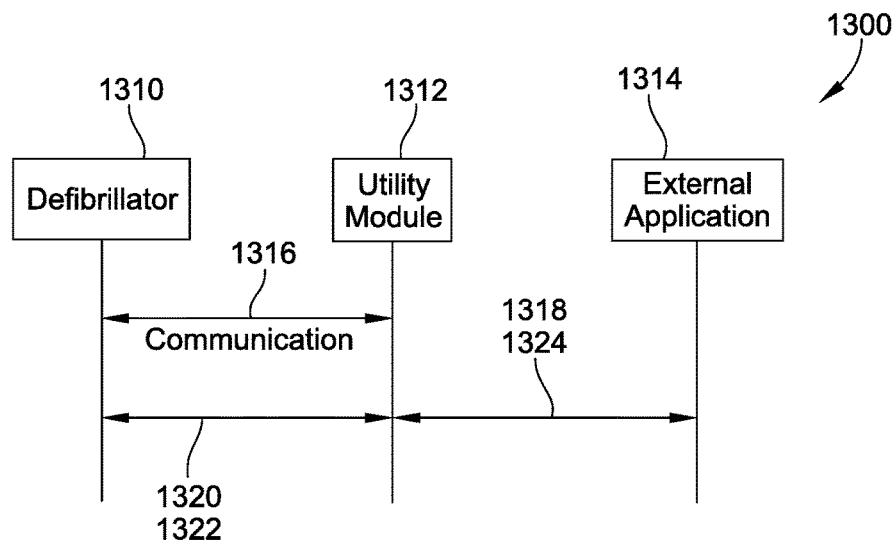
FIG. 25 further illustrates the operation of a command on the external serial port and more specifically, the operation of the command in a communication session occurring between the utility module of FIG. 5 and a defibrillator.

FIG. 25 further illustrates the operation 1300 of the open command 1318 on the external serial port. More specifically, FIG. 25 illustrates the operation of the open command 1318 in a communication session occurring between the utility module 1312 and defibrillator 1310. The open command 1318 is initiated by an external application 1314 such as a device agent of utility applications (e.g., device agent or other applications) 820 (FIG. 14), a parameter module 460 (FIG. 5), a server 810 (FIG. 14), or an adjunct medical device 850. Prior to the time the open command 1318 is initiated by the external application, FIG. 25 shows a communication session 1316 involving the bidirectional flow of data occurring between the defibrillator and the utility module. When the open command 1318 is received by the utility module, the utility module immediately issues a stop command 1320 to the defibrillator 1310. The defibrillator immediately responds by sending the utility module 1312 an acknowledge command 1322. On receipt, the utility module sends the external application an opened signal 1324 which then configures the utility module to quickly pass-through test interface commands from the external application 1314 to the defibrillator without interference.

More specifically, at that point, the utility module will enter into pass-through operation—examining each command received from the external port, responding to commands meant for the utility module, passing-through all other commands to the defibrillator and passing-back the defibrillator response to the external serial port. Illustratively, when in pass-through operation, certain commands may require special processing. When this occurs, external programs are not able to send test interface commands and see $CO_2$ data on the defibrillator at the same time. However, if this need may exist for verification teams, the communication between the utility module and the defibrillator may be re-established using a utility module initiate command. Upon receipt of this command, the utility module will initiate communication with the defibrillator using the utility module command.

If the defibrillator is not powered on when the open command is sent, the utility module will transmit the opened signal response on the external serial port. The utility module will then respond normally to commands meant for the utility module and give no response to other commands. The utility module response to defibrillator commands (no response) simulates the performance of the defibrillator when powered off.

Networked Interface. During normal operations, the defibrillator and the utility module will communicate with each other over a networking based connection. This mode of operation will be initiated by the utility module with the defibrillator utility module initiate command. The relationship of the various communication layers to each other have been previously described in connection with FIG. 21. The utility module and the defibrillator illustratively implement those layers/protocols as previously discussed in connection with FIG. 21.

In an illustrative message stream for $CO_2$ data transmitted from the utility to the defibrillator from the utility module to the defibrillator, the normal mode message may be sent from the utility module to the defibrillator at a periodic interval. If the $CO_2$ Module is present and operating normally, this timing will be driven upon receipt of a periodic sample. If the $CO_2$ Module is not present or has a malfunction, the utility module will emit this message on its own internal timing. The CO2 messages are illustratively sent at a rate of 5 Hz assuming that waveform data is sampled by the CO2 module at a 20 Hz rate which allows for one message to be sent on the sampling of the fourth sample. The message is conveyed by the utility module when the defibrillator is in a normal mode of operation and continues until FTP is started. When FTP is started the FTP protocol messaging preempts the CO2 messaging as described below. The CO2 waveform is sent only when the utility module is present and there is no major malfunction of the CO2 module. A null message is sent when the utility module does not contain CO2 or a major malfunction is detected within the utility module.

The incremented sample numbers are encapsulated into CO2 data fields and encapsulated by an IP header field and a TCP header field for controlling the path of the message according to the IP and TCP protocols. The encapsulated data message is sent from the utility module to the defibrillator through the physical layer with an address field, control field, protocol field, check bits, and flag controlling the destination and path taken by the message from the utility module to the defibrillator through the physical layer.

As another illustrative example, the utility module may send vital signs to the defibrillator. The vital signs may include ambient pressure, breath detected, EtCO2 value, FiCO2 value, respiration rate, IPI, and CRC. Using appropriate sampling rates, this data may be encapsulated into the IP and TCP header fields and further encapsulated into the physical layer fields to enable the routing of the vital signs message through the network layer down to the physical layer of the utility module and then over to the physical layer of the defibrillator for passing up to the network layer of the defibrillator for use by the defibrillator.

Illustratively, the utility module device status control signal is encapsulated with network and physical layer protocol information in a manner similar to the manner described above. In the case of device control status, the data includes information like the power status of the battery of the utility module.

The test interface commands include fields on the type of message, length of message, and the test interface command itself. The utility module transfer status message includes fields on the type and length of message, as well as a battery status indicator which causes the defibrillator to display a "Low Battery: Connect AC Power" message on the defibrillator display. Other messages may be sent between the utility module and the defibrillator in order for the utility module to coach the user of the defibrillator to perform a more effective defibrillation.

Similarly, in an illustrative message stream for SpO2 and HR data, the normal mode message is sent from the defibrillator to the utility module at a prescribed time interval. The messages with the HR and SpO2 data are illustratively sent at a rate that is slower than the rate at which the waveform data is sampled by the defibrillator. The message is conveyed by the defibrillator when the utility module is in a normal mode of operation and continues until FTP is started. When FTP is started the FTP protocol messaging preempts the messaging as described below. The waveform is sent only when the defibrillator is present and there is no malfunction of the HR and SpO2 module of the defibrillator.

The HR sample number is encapsulated in HR field and the SpO2 sample number is encapsulated in SpO2 field. The encapsulated HR and SpO2 data fields are encapsulated by the IP header field and TCP header field for controlling the path of the message according to the IP and TCP protocols. The encapsulated data message is sent from the defibrillator to the utility module through the physical layer with the flag field, address field, control field, protocol field, check bits, and flag controlling the destination and path taken by the message from the defibrillator to the utility module through the physical layer.

As another illustrative example, the defibrillator may send vital signs to the utility module. The vital signs may include ambient pressure, breath detected, EtCO2 value, FiCO2 value, respiration rate, IPI, SpO2, pulse rate, and CRC. Using appropriate sampling rates, this data may be encapsulated into the IP and TCP header fields, and further encapsulated into the physical layer fields to enable the routing of the vital signs message through the network layer down to the physical layer of the defibrillator and then over to the physical layer of the utility module for passing up to the network layer of the defibrillator for use by the defibrillator.

Illustratively, the utility module device status control signal is encapsulated with network and physical layer protocol information in a manner similar to the manner described above. In the case of device control status, the data includes information like the monitoring status of the utility module (i.e., manual or AED), power status of the battery of the defibrillator.

Figure 26:
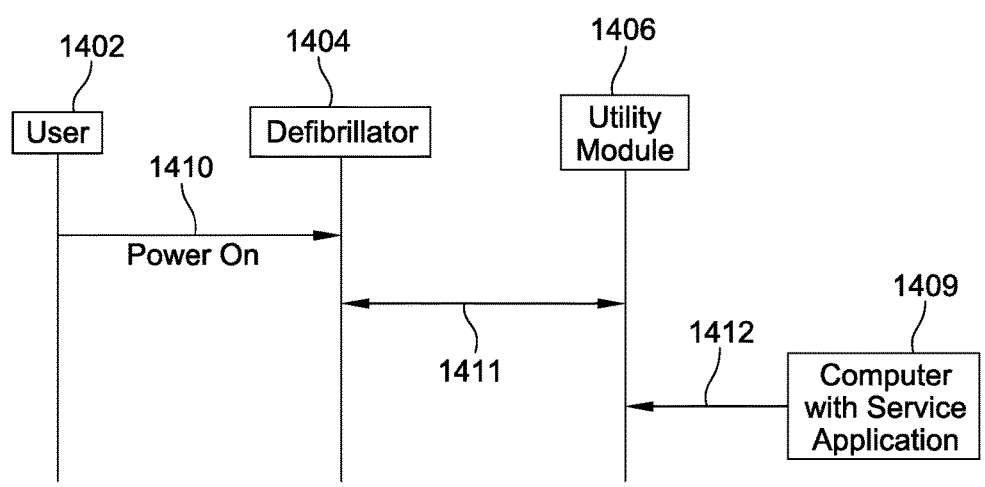
FIG. 26 shows a possible relationship of events for user power on of a defibrillator that is in electrical connection with a utility module of FIG. 5 of this disclosure.

FIG. 26 shows a possible relationship of events for user power on of a defibrillator 1404 that is in electrical connection with a utility module. At step 1410, the user 1402 powers on the defibrillator 1404. On power on, the defibrillator 1404 exchanges messages 1411 with the utility module 1406. A service application on a computer 1409 external to the utility module sends the utility module an open command 1412, and so on. The command can be applied to the serial port of the utility module (1050 in FIG. 20) that is configured to receive serial commands from external devices. In the illustrative embodiment shown in FIG. 26, the utility module is configured with a CO2 parameter module which operates in a manner previously discussed. The defibrillator can start a PPP client and then initiate a PPP connections message. The utility module is acting as the server to the defibrillator, listening for these connections. The defibrillator connects to a data socket created by the utility module and connects to the utility module control channel. The utility module connects to a data socket created by the defibrillator and connects to the defibrillator control channel. Throughout this process, the defibrillator could be polling the utility module to confirm that the foregoing connections have been made. With the SpO2, PR channel and the CO2 sockets open between defibrillator and utility module, the defibrillator begins to send SpO2, PR data to the utility module over the SpO2, PR data socket. The defibrillator controls the data transfer over that socket at a predetermined data rate using the utility module control channel. In addition, the utility module begins to send CO2 data to the defibrillator over the CO2 data socket. The utility module controls the data transfer over that socket at a predetermined data rate using the defibrillator control channel. The foregoing bidirectional flow of data between the defibrillator and the utility module continue until terminated by the operator.

Figure 27:
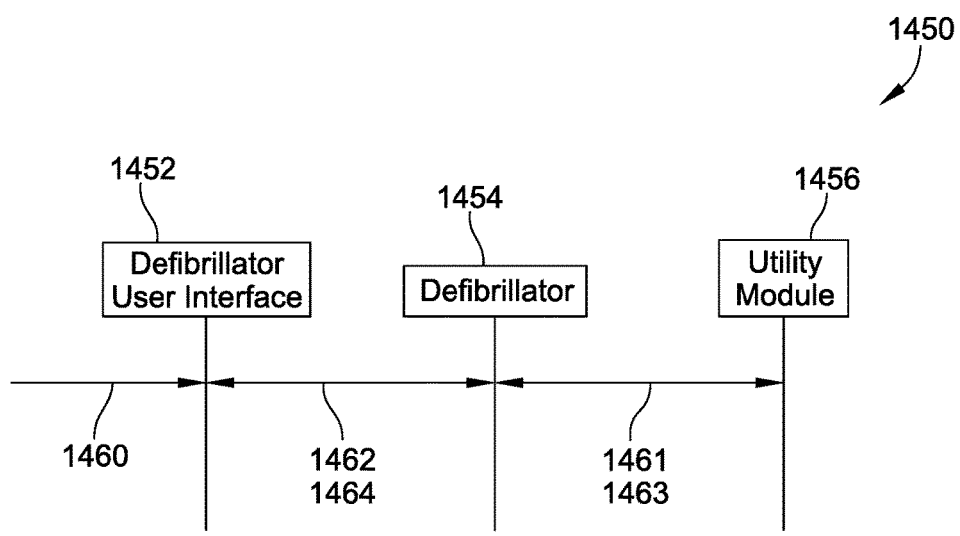
FIG. 27 shows an illustrative communication sequence between the utility module of FIG. 5 of this disclosure and the defibrillator.

FIG. 27 shows an illustrative communication sequence 1450 between the utility module and the defibrillator. The file transfer mode of operation between the defibrillator and the utility module of FIG. 5 is activated by a send data command 1460. Prior to a notify utility module command 1462, there is a bidirectional flow of data 1461 between the defibrillator and the utility module that may occur during a patient monitoring mode of operation as described above, whether or not the defibrillator is being used in a patient monitoring procedure. Messages from the defibrillator have an FTP byte flagged off since there is no transfer of FTP files in the illustrated patient monitoring mode of operation in this illustration. With the send data activated command 1460, the file transfer mode of operation has been activated. Illustratively, this activation may occur by a user pressing an activation button on the defibrillator interface 1452. Alternatively, this activation may occur by trigger signals that may be generated internally to the defibrillator, such as by programmed software. Alternatively, the trigger signals may be generated by the utility module or by an external device for application to the defibrillator by or through the utility module for providing a synchronous or asynchronous download of patient data and/or defibrillator settings for use by the utility module or the external device.

On activation of the activating the file transfer mode of operation between the defibrillator and the utility module, the user interface 1452 in this example, prompts the defibrillator with a command 1462 to change to a file transfer mode of operation. In response, the defibrillator changes over to a file transfer mode of operation. In this mode of operation, the defibrillator begins the transmission of an FTP file illustratively of patient and/or configuration settings. A file message is transmitted from the defibrillator to the utility module. By protocol, the utility module recognizes a message to be file data by the FTP byte which is flagged-on for file data messages. In the example, the utility module recognizes the message from the defibrillator to be a file message since the FTP byte of this message is flagged-on.

While the defibrillator is transmitting FTP files to the utility module, the utility module illustratively responds by sending messages back to the defibrillator indicating the status of the file download. The defibrillator continues to send the FTP file. The utility module continues to recognize this message to be a message file since the FTP byte of the message is flagged-on. The utility module continues to transmit messages back 1463 to the defibrillator on the status of the file download. Throughout this process, the utility module continues monitoring the FTP Byte of messages received from the defibrillator in order to know when the defibrillator has finished downloading its file. When the utility module recognizes that an FTP file has been downloaded, by detecting the flag-off of the FTP Byte in incoming messages, the utility module flags-on a byte of its download status message to indicate the success or failure of the FTP file download. On receipt of this message, the defibrillator illustratively sends the defibrillator user interface a notify transmission success or fail command 1464 for the purpose of alerting the user that the FTP file download has been successful or a failure so that the user can have tranquility that the file was successfully downloaded or re-activate the file download process in order to try to download the file again. After the user interface has been alerted on the success or failure of the download, the defibrillator switches from file transfer mode back to patient monitoring mode of operation whereupon the defibrillator returns to sending message data to the utility module. In this example, the FTP byte is flagged-off; indicating to the utility module that the message is a data and not a file message. The utility module returns to patient monitoring mode of operation whereupon the utility module resumes sending its data messages.

Advantageously, the file download enables external devices and/or the utility module to provide more informed coaching to a user of the defibrillator by enabling information available in downloaded patient data and configuration setting files to be used in coaching a user during a defibrillation process. In addition, with real-time download of batch patient and setting configuration information made possible by this disclosure, medical personnel have this information immediate availability for use in post-defibrillation treatment, instead of having to wait to retrieve this information after the defibrillation process is over and the data is downloaded. In addition, by having the real-time data of this disclosure to observe during a defibrillation process, medical personnel may understand better the correlation of patient vital data to the defibrillation data which can lead to better coaching techniques. These and other purposes are served by the real-time download of batch data from a defibrillator of this disclosure.

In the above example, the data from the utility module to the defibrillator is dedicated to informing the defibrillator on the status of the file download. In alternative embodiments, the utility module may continue transmitting data to the defibrillator while at the same time monitoring the file download and providing status on the file download to the defibrillator. Advantageously, this allows real-time utility module data, such as $CO_2$ data, to continue to be streamed from the utility module to the defibrillator while the defibrillator is downloading the file data. Hence, utility module and/or the external devices through the utility module are enabled in this embodiment to continue coaching a user during a defibrillation process during download of these files In an alternative embodiment, the utility module may further include a motion sensor (not shown) configured to detect a change in position of the utility module relative to its surroundings. Illustratively, the motion sensor is an accelerometer. Alternatively, the motion sensor may be any sensor configured to detect a change in motion by electrical, mechanical, or other methods.

Information from the motion sensor may be used to optimize the performance of the utility module and the coaching that is made possible using the utility module. For example, the user of a utility module may be coached by one or more external devices to move the utility module in a specified direction for advantage. For example, information from a sensor in a utility module in an ambulance vehicle may be used by the system to provide instructions to the driver of the vehicle on which hospital a patient should be taken to. As another example, the system may use the information to instruct the user of a utility module to reposition the utility module for better operation, such as to move the utility module to a position where it may receive better reception of a wireless signal or where it may provide better coaching to the defibrillator. For example, if a utility module is optimized for use within a restricted area, information from the sensor may be used to alert the user that the utility module has been moved outside the optimum area so that the user may take corrective action in order to improve the defibrillation process.

Information from the sensor may also be used to protect the utility module and to make it more secure. For instance, in the above example, the information that is generated by the sensor in the case of a breach of the restricted area by a user may be used to secure the device. For example, on the occurrence of the breach, the utility module may be programmed to do an automatic power-down or to enter a sleep mode operation of the device until the security breach is corrected. Alternatively, the event may trigger an alarm on the utility module and/or at an external device in order that action may be taken to make the utility module secure.

In an alternative embodiment, the communication module 490 shown in FIG. 4 may include a Radio Frequency Identification ("RFID") reader, which can also be called an on-board RFID reader. The on-board RFID reader may be configured for communicating with RFID tags, or another RFID reader, for the purpose of automatic identification and tracking. The RFID tags and the other RFID reader may be attached to objects in the environment external to the utility module. The environment may be any location in which the utility module is designed to be found, such as a location for testing the manufacture of the device, an ambulance, a hospital or other patient care center, etc. The RFID reader enables the utility module to discern where it is located with respect to its environment in order to use this information for enabling a more effective defibrillation process. For instance, if defibrillation is being performed in an office building by non-medical personnel, the RFID reader may alert the rescuer that a trained medical personnel is nearby in another office to assist because the RFID reader has detected an RFID tag embedded in an identification card carried by the medical personnel in the nearby office.

In an alternative embodiment, the communications module 491 shown in FIG. 4, other components of the utility module, and/or the housing of the utility module may include an RFID tag, which can also be called a status RFID tag. The RFID tag may be used for automatic identification and tracking of the utility module by an RFID reader external to the utility module. This tracking information may enable the network that is connected to the utility monitor to factor tracking information into the coaching that the network may provide the defibrillator.

In another embodiment, the utility module includes both an on-board RFID reader and a status RFID tag. The on-board RFID reader may be configured to provide or update data residing on the status RFID tag concerning patient data, configuration settings, etc. This updated patient data, configuration settings, etc. available to the utility module, including from the defibrillator or an external device, becomes available to an RFID system for automatic identification and tracking each time the RFID system interrogates the RFID tag by an external RFID reader. Hence, an RFID system for identifying and tracking utility modules may be improved since the RFID system is being synchronized with an RFID tag which is being updated by the internal RFID reader with more frequency. This result is an RFID system that contains data that is more current than the data that is internal to utility modules. In addition, any data available to the utility module may be immediately written onto the status RFID tag by the on-board RFID reader and picked up by an external RFID reader more quickly; thereby providing the RFID system also with the most current data on the utility module. These and other RFID features of this disclosure enables improved identification and tracking of the utility module in the RFID system which in turn enables improved coaching. For example, the system may use the feedback information from the RFID system to instruct the user of a utility module to reposition the utility module for better operation, such as to move the utility module to a position where it may receive better reception of a wireless signal or where it may provide better coaching to the defibrillator. The system may also use the feedback from the RFID system to reconfigure settings in the utility module or defibrillator or external devices being used with the utility module in order to optimize the performance of the utility module based on the RFID system feedback.

The RFID communication of this disclosure can occur at any suitable frequency. Examples of such frequencies are centered around 130 KHz, 13.56 MHz, 900 MHz, 2.4 GHz, and so on. The higher the frequency, the faster the data communication will be. The RFID tags can be passive or active. The RFID readers and passive RFID tags in the 900 MHz frequency range can be part of the standardized Class 1 Generation 2 UHF Air Interface Protocol, also known as the "Gen 2 Spec". It will be appreciated that other RFID communication methods and protocols may also be used with this disclosure.

Figure 28A:
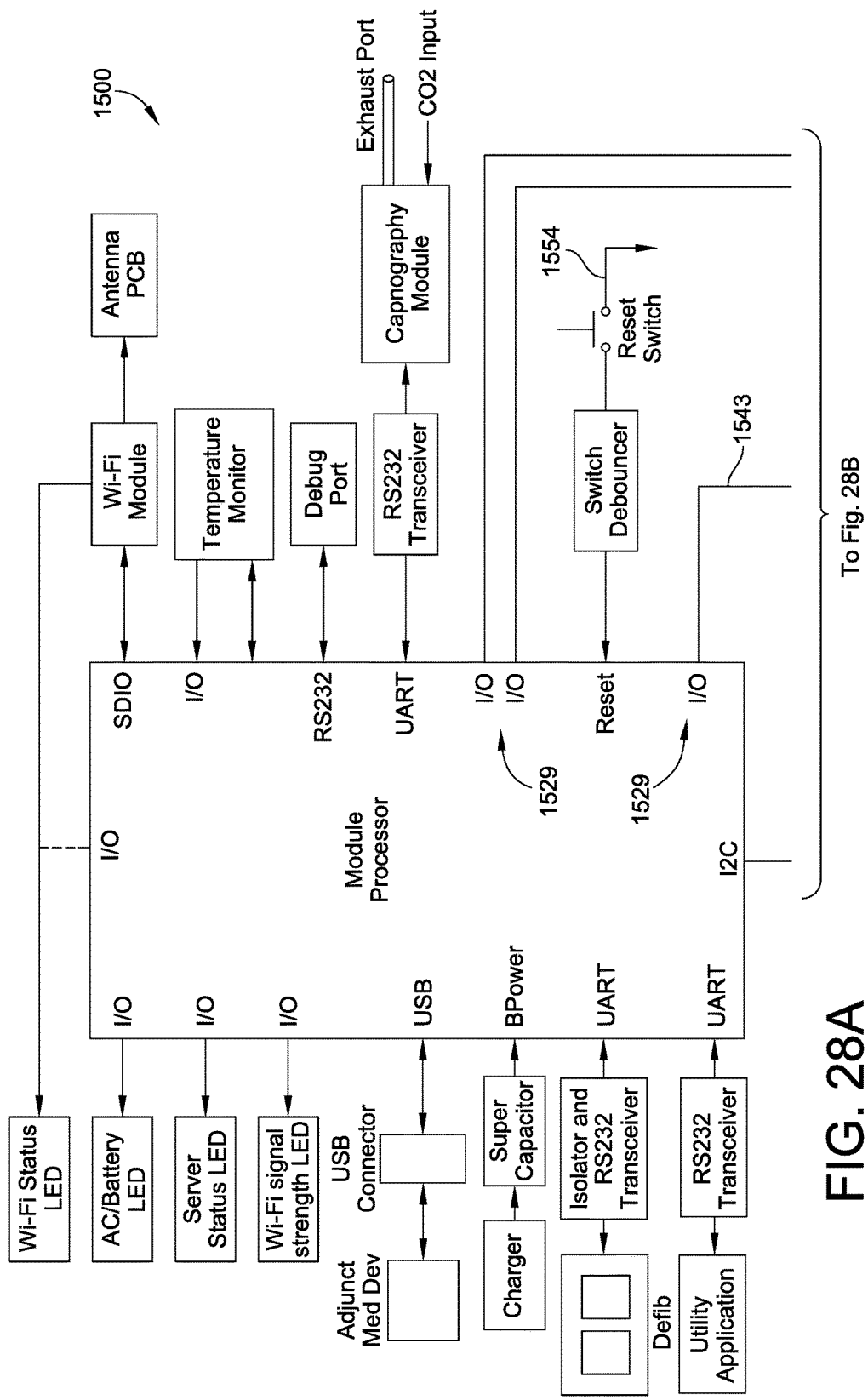
FIGS. 28A,B are an illustrative functional diagram of FIG. 5 further showing the power management system of this disclosure.
Figure 28B:
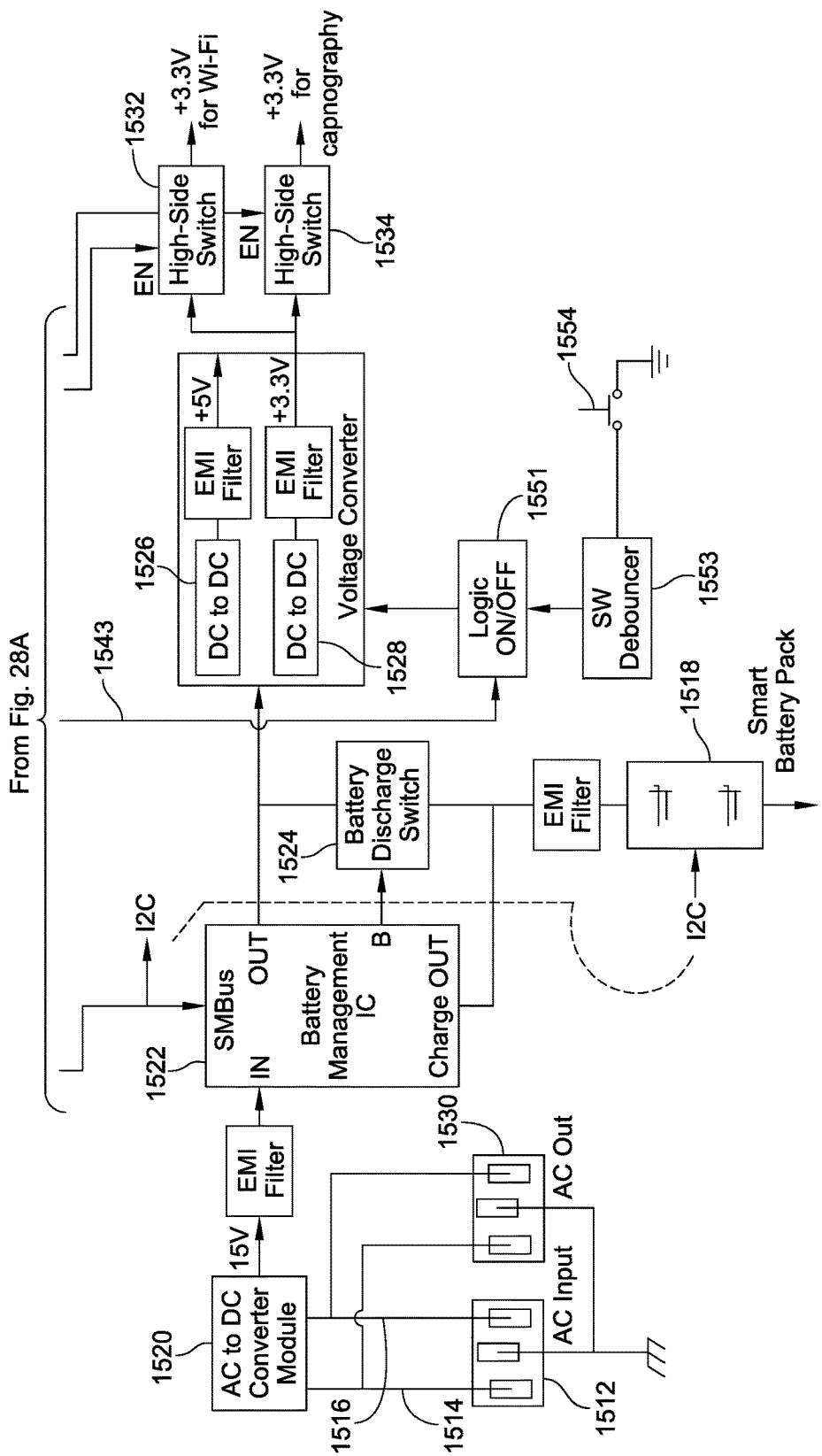

FIG. 28 shows an illustrative embodiment of the utility module of FIG. 5 with a power management module 550. FIG. 28 shows a utility module 1500 which contains many of the components appearing in FIG. 5 (whose function and operation are as described in FIG. 5), except that the power manager 550 of FIG. 5 that is shown in FIG. 28 has been exploded to show the components that illustratively make up the power manager. As shown, AC power is provided to power manager 550 by grounded AC input connector 1512. Grounded AC out connector 1530 is configured to allow AC power that is input to the utility module by AC input connector 1512 to be output via out connector 1530 for use by another utility module or a defibrillator. In one embodiment, AC input connector 1512 is a plug for receiving input power over a power cord (not shown) from an AC outlet. In one embodiment, AC out connector 1530 is a socket connector formed especially for fitting into a portion of the utility module bridge back and then connecting to the rear of a defibrillator to provide power to the defibrillator. In one embodiment, AC out connector 1530 is a socket adapted for connecting with the plug portion of a standard power cord (not shown), with the socket portion of the power cord connecting to a mating plug of another utility module. In one embodiment, connectors 1512, 1530 are adjacent one another as shown, at the rear of utility module 1500. Other embodiments with other plug or socket combinations may be used.

AC input connector 1512 and out connector 1530 each has a positive lead, a negative lead and a ground lead. The positive leads of AC connectors 1512, 1530 are connected to power line 1514 to apply positive voltage onto AC-to-DC converter module 1520. The negative leads of AC connectors 1512, 1530 are connected to power line 1516 to provide a negative lead for AC-to-DC converter module 1520. Ground leads shown provide the AC-to-DC converter module 1520 with grounding. The output from the AC-to-DC converter module 1520, in this embodiment, is a 15 Volt output to battery management IC 1522.

Battery management IC 1522 in this embodiment is an integrated circuit (IC) that interfaces with the module processor via I/O port 1527. The information exchanged through this port enables module processor to keep tabs on the health of smart battery pack 1518 and to output a signal indicative of that health to the AC/battery LED shown in the FIG. Battery management IC 1522 receives power from the AC-to-DC converter module 1520 and outputs power to smart battery pack 1518 and to 3V DC-to-DC converter 1528 and 5V DC-to-DC converter 1526. Smart battery pack 1518 connects with a battery discharge switch 1524 and also connects directly to module processor to supply power.

Smart battery pack 1518 is illustratively two Li-ion batteries. The batteries are charged by a charge from battery management IC 1522 that is applied to smart battery pack 1518. The batteries apply their charge to power the module processor. The battery management IC has an SMBUS/I2C interface to allow for this I2C port communication with the module processor. Illustratively, the smart battery pack is battery pack, 3S1P, with Li-ion batteries, part number 102-003925-001, from Micro Power Electronics, Inc., Beaverton, Oreg.

Battery management IC 1522 is controlled by module processor by control signals applied from port I2C of module processor to the battery management IC 1522. Battery management IC 1572 applies a first signal to the module processor and a second signal to battery discharge switch 1524 for controlling the discharge of the smart battery pack 1518 during conditions in which battery discharge is required. Power from the smart battery pack is also applied to voltage converters 1526, 1528 which convert the (15 volt) DC power into 5 volt power and 3.3 volt power as shown. 3.3 volt power is applied to a first high-side switch 1532 and a second high-side switch 1534. The first high-side switch 1532 provides 3.3V power for application to the Wi-Fi module. The second high-side switch 1534 provides 3.3V power for application to the capnography module 1508.

Control signals from the module processor are issued through I/O ports 1529 of the module processor. Both first and second high-side switches 1532, 1534 are controlled by a control signal I/O port of the module processor. The first high-side switch 1532 is further controlled by a second control signal coming from a second I/O port of the module processor. In addition, a third control signal 1543 coming from I/O ports of the module processor is applied to an ON/OFF logic circuit 1551 of the power management module to control the ON/OFF state of the voltage converters. The ON/OFF state of the utility module is also controlled by a reset switch 1554 which connects on a downstream end to a ground line and on an upstream end to a switch debouncer circuit 1553 which generates the ON/OFF state signal that is applied to the ON/OFF logic circuit 1551 to turn the Wi-Fi module and capnography module ON/OFF in response to the action of the reset switch 1554. The action of the reset switch 1554 also triggers a utility module reset logic circuit 1552 which puts a reset signal to reset port of the module processor.

In operation, the utility module 1500 preferably is powered by AC power whenever AC power is available. Specifically, when AC power is sufficiently available, an OUT port of battery management IC 1522 of the power manager 550 is active. This allows DC power, taken directly from AC-to-DC converter module 1520 and applied to the battery management IC 1522, to be applied to the OUT port of the battery management IC 1522 and applied to the voltage converters 1526, 1528. As previously described, the voltage converters 1526, 1528 apply the incoming 15 volt signal to the utility module by way of the DC-to-DC converter 1526 stepping down the incoming 15 volts to a voltage level of 5 volts and DC-to-DC converter 1528 stepping down the incoming 15 volt power to a voltage level of 3.3 volts.

However, if sufficient AC power is not available, the battery management IC 1522 of the power management module switches the supply of power to the utility module from DC power taken directly from the AC-to-DC converter module to the smart battery pack 1518. Specifically, when AC power is not sufficiently available, the OUT port of the battery management IC 1522 goes low and the B (or battery) port of the battery management IC 1522 goes high. This causes battery discharge switch 1524 to allow charge from smart battery pack 1518 to pass through the battery discharge switch 1524 to supply voltage converters 1526, 1528 with the voltage required for the DC-to-DC converters to step down the incoming voltage into 5V and 3.3 volt levels required to power the utility module, as previously described.

Additionally, the battery management IC 1522 charges the battery at a suitable rate. This IC is also used to protect the battery and the utility modules from over-voltage, under-voltage, and over-current. The charging voltage and current ratings can be selected by SMBUS protocol which provides the interface with the module processor 1510. The battery management IC may also have a feature to discharge the battery even if AC power is present.

The battery management IC 1522 may charge the battery based on well-known current or time methods of charging. If the battery is heavily discharged, it may be desirable to initially charge the battery at a rate that is different from the normal rate of charge of the battery. Advantageously, the battery management IC may be configured to pre-charge the battery at a predetermined rate which may be safer for a low or dry charge battery before charging the battery a second predetermined rate which may be at a faster rate, for example. Power manager 550 shown in the illustrative embodiment of FIG. 28 may further include battery authentication and security schemes. Power manager may also be configured to allow power from a defibrillator to charge the smart battery pack when AC power is unavailable and the charge in energy storage device 415 of the defibrillator of FIG. 4 is available for this purpose.

Figure 29:
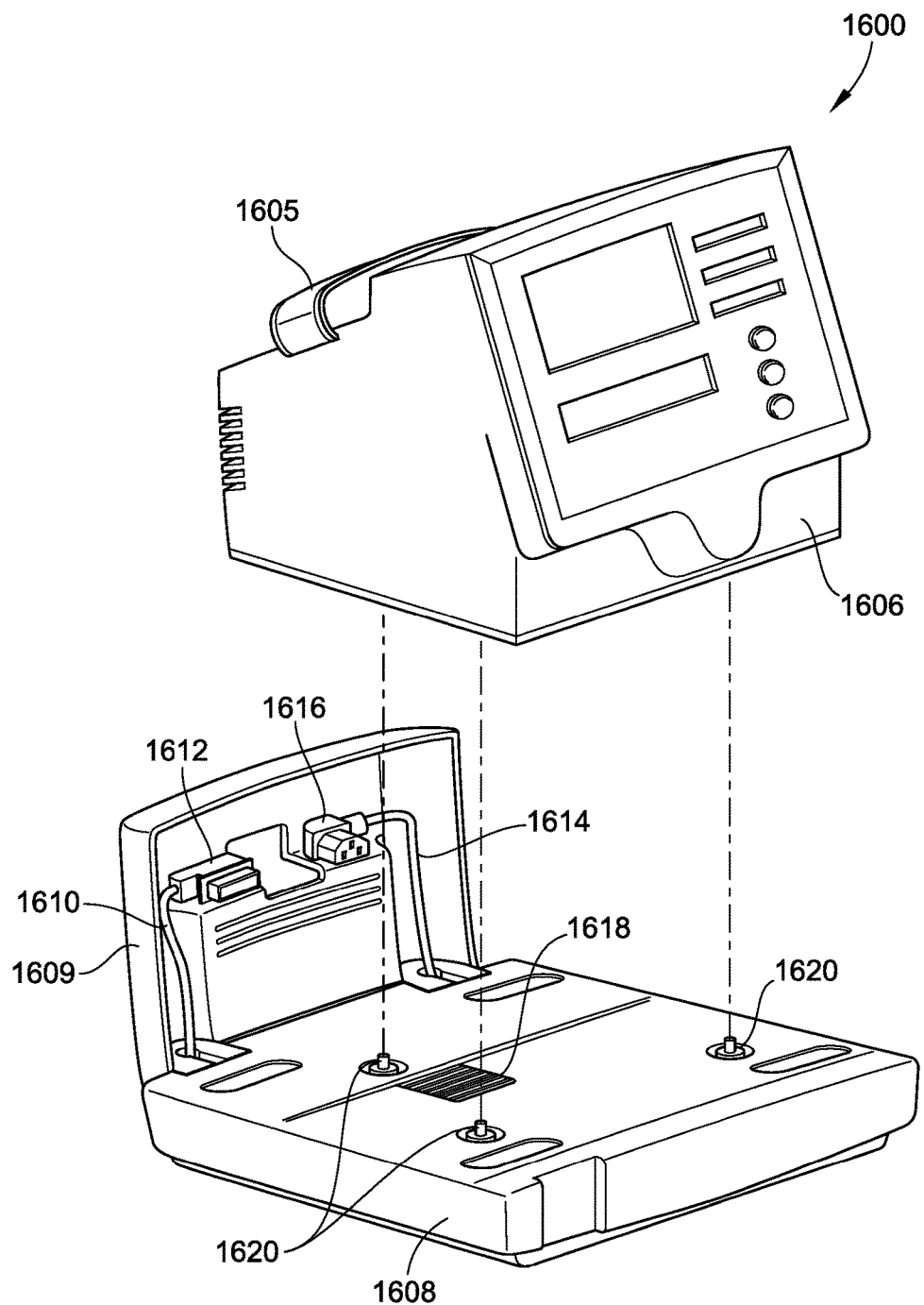
FIG. 29 is an isometric view of a defibrillator and a utility module of this disclosure having a back bridge.

A utility module defibrillator assembly 1600 is shown in FIG. 29 with a utility module 1608 including a bridge back 1609 to provide data and/or power to a defibrillator 1606. Alternatively, the utility module may provide data and/or power to the defibrillator without the use of the bridge back as described further later below. In either and other embodiments, the utility module provides a docking station for receiving and holding and for providing data and/or power to the defibrillator. More particularly, as shown, defibrillator 1606 may include a carrying and maneuvering handle 1605 so that a user or installer may place the defibrillator atop (i.e., along an upper portion of) utility module 1608. Connecting the utility module to the defibrillator are data cable 1610 and RS232 compliant connector 1612, which may be, for instance, a Db-9 connector. More specifically, the data cable 1610 is provided with a data connector 1612 that mates with a data connector on the back side of the defibrillator 1606 when the defibrillator is placed atop the utility module 1608 and pushed back against the bridge 1609 in order to bring the data connectors of the bridge and the defibrillator into mating engagement.

Power to the defibrillator is supplied by power cord 1614 and grounded AC power socket connector 1616. More specifically, the power connector 1616 mates with a power connector on the back side of the defibrillator when the defibrillator is placed atop the utility module and pushed back against the bridge 1610 in order to bring the power connectors of the bridge and the defibrillator into mating engagement. As described with respect to FIG. 28, AC power connector 1616 may be a three-prong AC socket connector that is inserted into a suitably designed portion of the bridge back 1609, e.g., a reversible snap-fit receptacle. RS232 compliant connector 1612 may also be specially designed to fit into a snap-fit receptacle on the bridge back. Power is routed to the AC power connector 1616 through power cord 1614 from the power manager 550 (see FIG. 28). Data is routed to RS232 compliant connector 1612 though data cable 1610 from the module processor.

Defibrillator 1606 rests atop the utility module and is connected via three thumb screws (not shown) that are inserted from the bottom of the utility module and through threaded receptacles (not shown) defined in the utility module. The threaded receptacles defining orifices 1620 on the top and like orifices on the bottom of the utility module are for the thumb screws to pass there through. A portion of each thumbscrew that emerges from the top of the utility module through orifices 1620 is received by threaded receptacles provided on the bottom of the defibrillator for holding the defibrillator and utility module in a threaded engagement. As previously discussed in connection with FIG. 5, the fan 506 internal to the utility module 455 provides circulating air to cool the components internal to the utility module 455 and to cool a docked defibrillator. As shown in FIG. 29, a grill 1618 defined in the utility module provides a passageway for the cooling of the defibrillator by the fan residing in the utility module. The defibrillator may also be provided with a grill along the side of the defibrillator that sits atop the utility module such that the grill aligns with grill 1618 of the utility module when the defibrillator is properly seated. The defibrillator grill provides a passageway for the cool air from utility module to enter inside the defibrillator to provide cooling.

Advantageously, this or other kind of fastening mechanism may also be used to connect additional utility modules in a stacking arrangement as shown in FIG. 30. FIG. 30 depicts an exploded view of an assembly of the defibrillator 1606 of FIG. 29, utility module 1608 with bridge back 1609 shown apart therefrom, and a plurality of utility modules 1658, 1659. The utility modules may each have a different parameter module, i.e., a physiological sensor or device for sensing a physiological parameter of a patient, such as the concentration of $CO_2$ in the patient's exhaust breath, the patient's ECG symptoms, and so forth. As shown in FIG. 30, to connect each of these modules to each other in a bundled utility module arrangement each of utility modules 1608, 1658, 1659 may be provided with threaded receptacles 1621 defining orifices along the top and bottom sides of each utility module so that three thumb screws 1622, 1624, 1626 may be used to threadingly connect each of utility modules 1608, 1658, and 1659 to each other and to the defibrillator in a vertical stacked arrangement. The thumb screws may be provided with small D-ring handles 1660 for easy hand-threading into mating threads (not shown) in the bottom of the defibrillator.

In the configuration shown in FIG. 30, the top-most utility module includes the bridge back 1609 (shown set-back from the utility module) but the bridge back is actually connected to the utility module in this illustrative example either by an attachment mechanism (such as by screws) or by an integrated utility module—bridge back casing. As previously discussed, the bridge back holds the data and power connectors to route data and power from utility module 1608 to the defibrillator. Illustratively, this top-most utility module may be designated as the host utility module since it may be designed to control the communications between the defibrillator and the utility module and to manage the other tasks in the stacked bundled utility module arrangement including the bidirectional communication between the bundled utility module and an external device as previously described. In another configuration, the utility module 1608 may be designed to serve as a host but be provided without the bridge back. In this case, data communications between the host utility module and the defibrillator may occur through a data communication link established between an RS232 port or wireless chipset residing in the defibrillator and a communication module residing in utility module 1608. The communication module may illustratively be of the kind shown as communication module 490 in FIG. 4. The power to the defibrillator in this case may be provided by an AC power cord that comes with the defibrillator and that may be connected to AC out plug 1530 (shown in FIG. 29) residing in utility 1608. Alternatively, the AC power cord of the defibrillator may be connected to another AC outlet.

In another configuration, the utility module 1608 may be provided with the bridge back 1609 but be designated to serve as a client utility module to one of the other utility modules 1658 or 1659 one of which in this example may serve as the host utility module in that stacked arrangement.

The utility modules, whether one or more, enable valuable coaching to be provided to the defibrillator such as through one or more parameter modules (460 in FIG. 4) residing in one or more of the utility modules, one or more other modules residing in one or more of the utility modules, or through one or more external devices that may provide the defibrillator with data through one or more of the utility modules acting as proxy for the rescuer to use in a defibrillation process. The data from parameter modules such as data concerning the carbon dioxide in the patient's breath, a heart rate or other heart parameter, blood pressure, and so forth may include the data previously described in connection with the other FIGS. above. Advantageously, the use of more than one utility module configured in a stacked arrangement as described in FIG. 30, a daisy-chain arrangement as shown in FIG. 33, or in any other arrangement enable more data to be made available to the rescuer; thereby enhancing the effectiveness of the defibrillation process.

In the illustrative embodiment of a bundled utility module in a stacked arrangement as shown in FIG. 30, illustratively utility modules 1658, 1659 serve as the client utility modules. As a client they could have all of the functionalities of the host utility module 1608. However, the disclosed bundled utility module advantageously enables utility modules that are designed to serve only as client utility modules to include only a subset of or some functionality other than may be provided by the host utility module 1608. In this way, a user may mix and match different client utility modules with a predefined utility module in order to provide the robustness and functionality required by the bundled utility module. For more on the advantages of the disclosed bundled solution, refer to the discussion above in connection with FIG. 10B where module cartridges having the same or different functionalities may be inserted into receptacles defined in a utility module to enable one utility module to provide a bundled utility module solution.

In the vertical stacked arrangement of utility modules shown in FIG. 30, the modules 1658, 1659 may be interconnected for power and data as described below with respect to FIG. 33. For example, in one embodiment, each module has a three-prong power socket inlet and a three-prong power plug outlet. The power outlet of the host utility module 1608 is used for powering the defibrillator as described in FIG. 29. The host utility module may also be used to power utility module 1658 stacked under the host utility module. Data communications between utility modules 1658, 1659 with utility module 1608 may occur through communication module 490 (provided in utility modules 1658, 1659) as described in greater detail in connection with FIG. 5.

Figure 31:
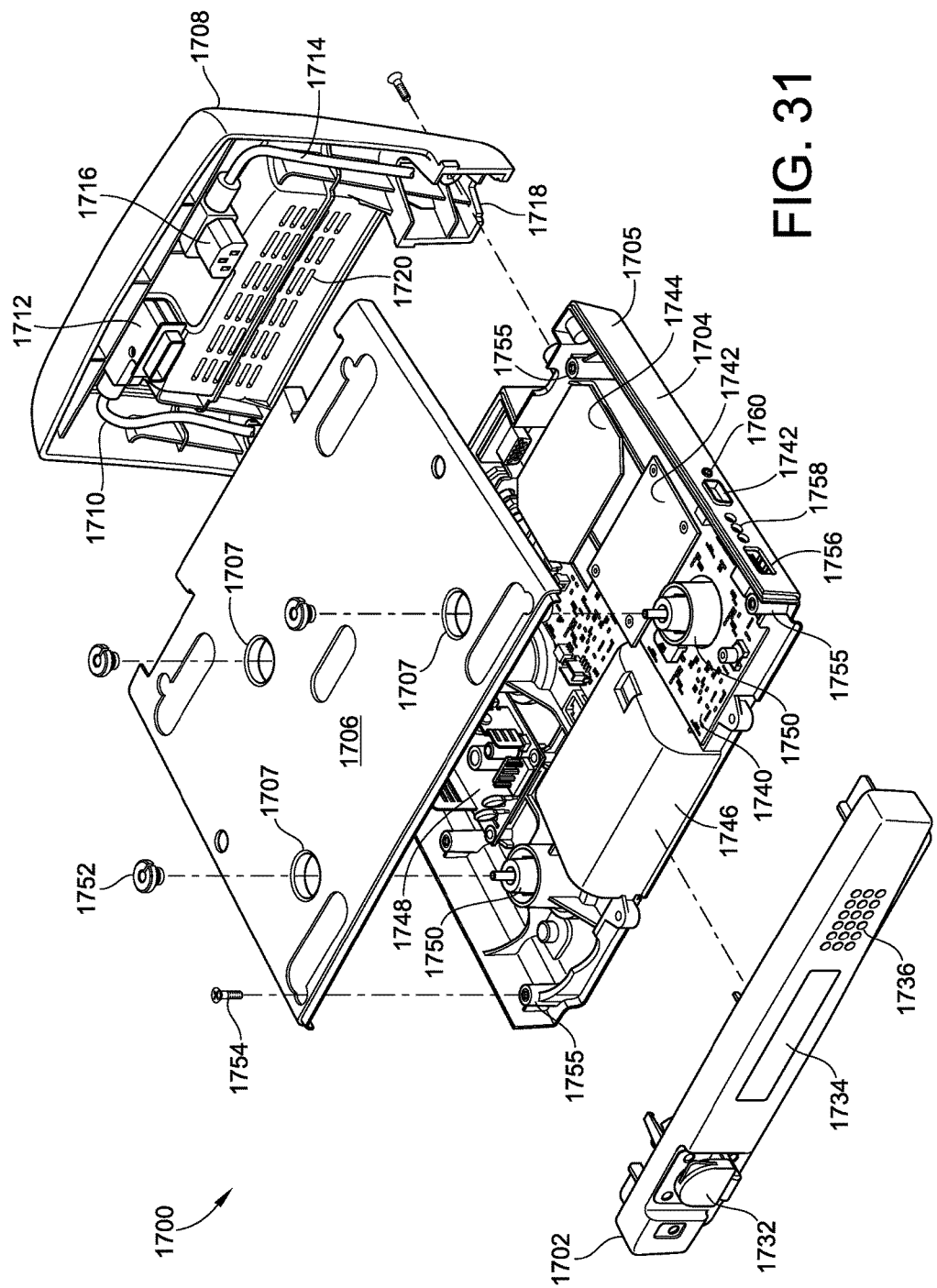
FIG. 31 is an exploded view of a utility module and back bridge of this disclosure, showing details thereof.

A more detailed view of a utility module 1700 is depicted in FIG. 31. The utility module, also known as the extension module assembly, includes a front panel 1702, a bottom enclosure 1704, a top cover 1706 and back bridge 1708. Bottom enclosure 1704 includes three pillars 1750 (only two shown in this view) for accommodating the securing fasteners discussed below. Top cover 1706 includes three orifices 1707 for the fasteners. In addition, the fasteners may be secured to the utility module using isolation mounts 1752. The top cover 1706 may be secured to the bottom closure 1704 using additional fasteners 1754 (four shown) and appropriate mounts 1755 (three shown) in the bottom closure.

In this view, data cable 1710 and data connector 1712 are seen emerging from the inner portions of the module assembly for placement on the back bridge 1708. Cable 1710 and connector 1712 may be RS-232 compliant or may instead conform to other accepted industry standard. Cable connector in this embodiment is an RS-232 plug connector. Power cable 1714 is seen emerging from the inner portions for placement of power connector 1716 on the back bridge 1708. In this embodiment, power connector 1716 is a grounded, three prong AC power socket cord for use in 110V U.S. applications. Other embodiments may use other standards, such as for 220V in other countries.

Back bridge 1708 includes a reversible socket snap-fit mount 1722 for data connector 1712 and also includes a reversible socket snap-fit mount 1724 for power connector 1716. The reversible mounts allow the power and data connectors to be removed from their mounts as desired and then snapped back in when desired. Back bridge 1708 also includes a grill 1720 for ventilation and heat removal, the grill assisted by the ventilation fan described previously. As seen in this view, back bridge 1708 includes an open area below grill 1720 and between the dovetail portions 1718 (shown on right side only) that allow the back bridge to mount to the bottom enclosure 1704. This open area allows complete access to the rear of the bottom enclosure and is suitable for placement of the power- and data.

The front panel 1702 of the utility module provides the front "face" of the module. The front panel 1702 includes an accessory or parameter module 1732, which may have additional electronics or circuitry within the enclosure 1704. The front panel may also include a display 1734, which will be discussed in greater detail below with respect to FIGS. 34A-34D. Front panel 1702 also provides a convenient location for Wi-Fi antenna 1736 and any additional circuitry or mounting board, such as a printed circuit board (not shown) useful for the antenna.

Bottom enclosure 1704 provides a housing for the components of the utility module 1700. The utility module includes at least one printed circuit board (PCB) 1740 for mounting the components of the utility module. PCB 1740 may mount module processor 1742, which provides the principal control for the entire module. The PCB may also mount many other components of the necessary circuitry, such as memory elements, the Wi-Fi module and the CMOS battery discussed above. Note that the additional circuitry 1744 that may be necessary for the accessory or parameter module may be placed near PCB 1740 and module processor 1742.

It may be desirable to separate these control boards from the power-providing and managing aspects of the utility module. Thus, a battery pack 1746 and AC-to-DC converter 1748 are placed a little further away from the control boards in this embodiment. Not shown in this view are the other power management circuits discussed above. Thus the battery management IC, the battery discharge switch the circuitry and logic associated with these elements discussed above with respect to FIG. 28, may be placed further away from PCB 1740 and module processor 1742. These circuits may reside in the areas to the top left, hidden by top cover 1706, in this view.

Right side panel 1705 includes several useful features. Data connector 1756 may be a USB connector for communicating with at least the module processor and other components of the utility module. LED display 1758 includes, this embodiment, three LEDs for displaying status of components of the module. As noted above in the discussion above, the LEDs may indicate status of the Wi-Fi connection, AC/battery status, and Wi-Fi signal strength. In some embodiments, one of the LEDs may be used to indicate a status of the defibrillator when it is connected to the utility module. Switch 1760 is a cutoff switch, used to switch off a wireless or Wi-Fi capability of the utility module, such as for example in an airplane or hospital.

Figure 32:
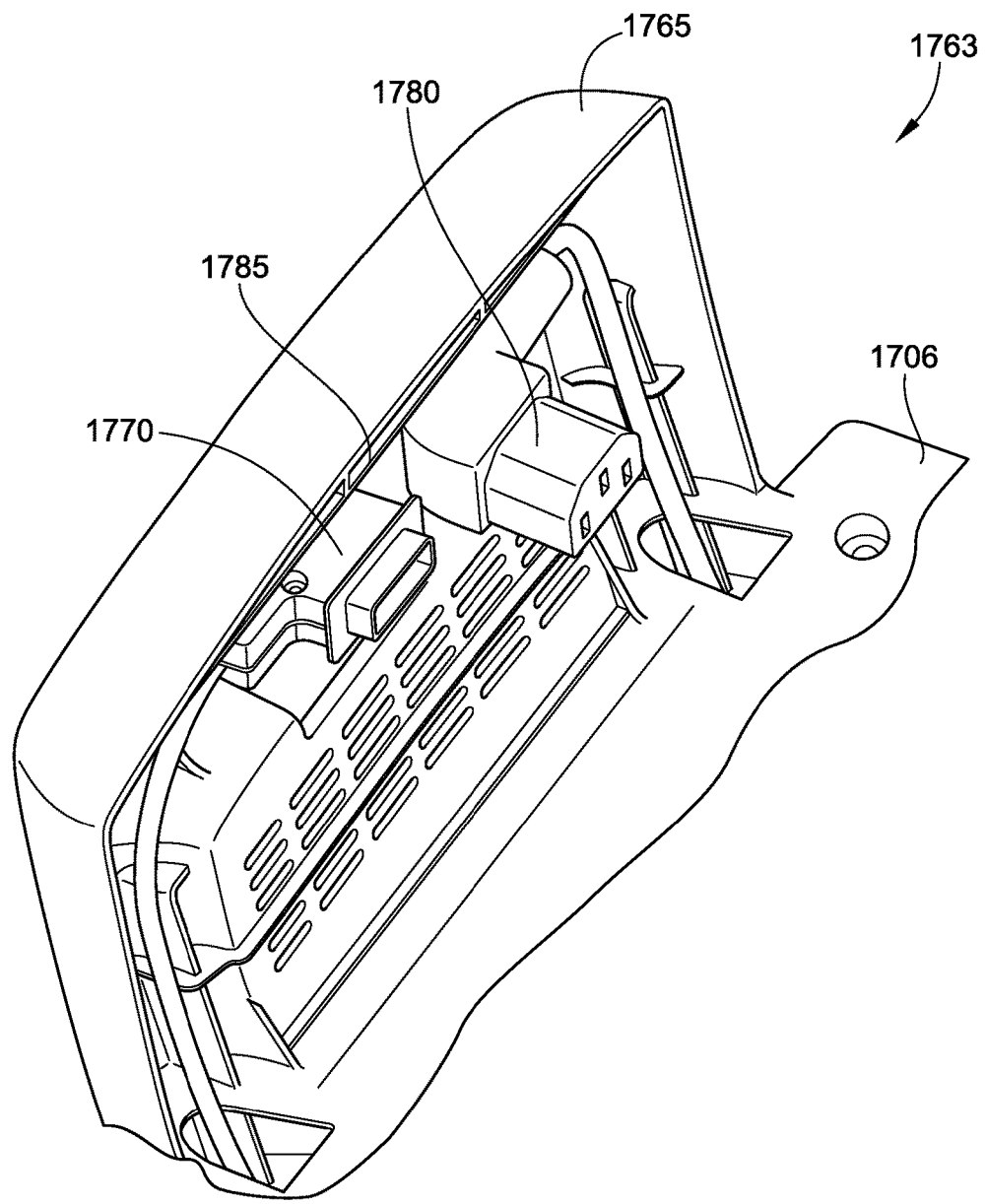
FIG. 32 is a top isometric view of a top portion of a back bridge with data and power connectors for connection with a defibrillator according to this disclosure.

Another useful view of the utility module defibrillator connection 1763 between the defibrillator and the utility module is depicted in FIG. 32. FIG. 32 shows data communication and power connectors 1770, 1780, respectively, in mating engagement with their counterpart connectors in the bridge back 1765. More specifically, socket power connector 1780 and socket data communication connector 1770, in this case a Db-9 connector, have been snapped into the bridge back and thus are relatively secure and non-moving during assembly. Heat grill 1784 is also visible in this view.

The utility modules disclosed herein and discussed with respect to FIGS. 28-32 can each be equipped with a parameter module 460 as described in FIG. 4.

It is thus clear that the utility modules or extension module assemblies disclosed herein may vary from one embodiment to another, at least because each module may include a different parameter or accessory module. Instead of having only a single utility module for each defibrillator, it may be useful instead to have more than one utility module available for bundling together with a host utility module, with each utility module having a different parameter module or in some cases overlapping functionalities. The overlapping functionalities could allow a bundled utility module to be used with more than one patient contemporaneously or for fail-safe redundancy purposes. For this purpose, the disclosed utility modules can be connected in a vertical stacked arrangement as shown in FIG. 30; in a horizontal arrangement as shown in FIG. 33, or in other arrangements; whereby a single primary utility module such as utility module may be use to provide a power source and a data communication link with one or more other utility modules that are connected to the primary utility module in a bundled utility module solution.

In the embodiment shown in FIG. 33, primary or host module 1800 may be equipped with a capnography module and may connect to a second module, client module 1801, equipped with a different parameter module, such as a module equipped to measure and display an ECG. A third module, client module 1802 may also be powered in this series, the third module 1802 equipped with for measuring blood pressure in a non-invasive way. The modules may communicate with each other through data communication links 1806 as described in FIGS. 4, 5. The modules may be interconnected in power through power links 1808 as described in FIGS. 4, 5. Electrical connections 1810 may, for example, be provided by the communication module 490 previously described (e.g., the pairing of defibrillator data connect port 440 and data outlet 475 in the case of the defibrillator and utility module and the data communication enabled by the pair of communication modules in the case of pairing of utility modules to each other. Power connections 1812, 1814 may be provided by the pairing of power connect 445 and power outlet 470 as described in FIG. 4. In this embodiment, host module 1700 receives and transmits data to the defibrillator 1850 through the data communication link Data may also transferred bidirectionally between the host module 1800 and client modules 1801, 1802, and between the client modules 1801,1802, through data communication links Power may be transferred between the defibrillator and each utility modules over the power links. In other words, with the defibrillator as part of the daisy chain, power from any one of the utility modules may be used to power the defibrillator. In addition and alternatively power from the defibrillator may be used to power any one or more of the utility modules in the daisy chain. Primary utility module 1800 may be powered through a battery pack or through a convenience wall outlet, as described above. The defibrillator illustratively receives power from AC out plug 1530 (FIG. 28) of the host utility module 1800. Secondary utility module 1801 may be powered through the power link 1808 illustratively a power cable extending from primary module 1800, in a manner similar to the power connection between the defibrillator and the host utility module 1800. Additional AC out plugs 1530 may be provided in host utility module 1800 for this purpose. Power transfer between client utility modules may occur similarly with the utility modules provided with an AC out plug 1530 to enable a plug from one utility module to plug into the AC out plug of the other. The utility modules may also receive power from convenience outlets or any other suitable power source.

The front panels of the utility modules were discussed above. The front panels may have one or more parameter or other modules integrated into the utility module design. Alternatively, the front panels may provide one or more openings or receptacles for receipt of a parameter or accessory module cartridge as described in connection with FIG. 10B, which may have many different health monitoring applications. Several embodiments of front panels 1910 and depicted in FIGS. 34A-35D are discussed here. A first embodiment is disclosed in FIG. 34A. This embodiment includes a capnography module 1902, used for measuring the $CO_2$ concentration in a patient's breath. A display 1906 in this instance displays two status indicators, a "five-bar" display for the strength of the Wi-Fi connection and a solid or 100% charged battery indication. Display 3906 may be in addition to or in place of the LED display panel on the side panel of the utility module previously described.

Figure 34A:
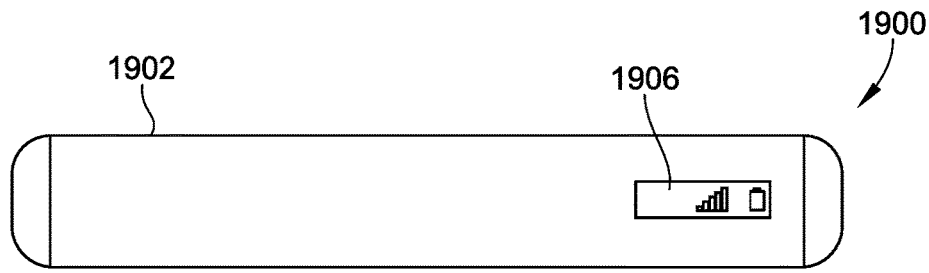
FIGS. 34A-34D depicts several embodiments of a front panel of a utility module of this disclosure.
Figure 34B:
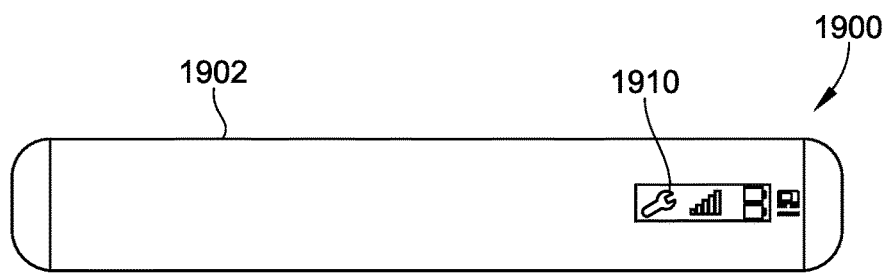

A second embodiment of a front panel is depicted in FIG. 34B. This embodiment includes a utility module 1902, also a $CO_2$ or capnography module as shown in FIG. 34A. This embodiment uses a more complex screen or display 1910. Display 1910 includes a first symbol (a wrench) which may indicate that the utility module needs to be serviced. The screen also includes a symbol for the strength of the Wi-Fi connections and two battery status indicators. The fourth symbol resembles a front face of a defibrillator and indicates that the utility module is in communication with a defibrillator and is exchanging information with the defibrillator.

Figure 34C:
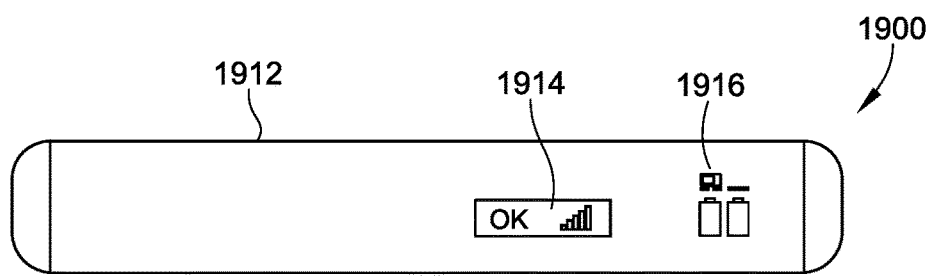
Figure 34D:

FIG. 34C includes yet another embodiment, this one with an ECG parameter module 1912 and two separate displays 1914, 1916. First display 1914 indicates "OK" for service parameters and gives a five-bar Wi-Fi signal strength. Second display 1916 may be a separate display showing information on the smart battery pack discussed above, the screen showing full charge on two batteries and also suggesting a that there is a connection with defibrillator as shown by a very tiny icon above the battery status indicators. Finally, FIG. 34D depicts a front panel with an ECG accessory module 1912 and a display 1918. Screen 1918 is somewhat large and includes icons or symbols for four status indicators. These include "OK" indicating that the utility module is in good working order, a high signal strength for the Wi-Fi connection, full charge for two batteries and an indicator showing that the utility module is in connection with its defibrillator. FIGS. 34A-D thus provide illustrative examples of information that may be displayed on a utility module of this disclosure to help in a defibrillation process.

In connection with FIG. 10B, it was discussed how a single utility module may be provided with more than one receptacle to receive more than one utility module cartridge in order to boost the functionality and/or robustness of a utility module. In FIGS. 34A-D, it is also seen how a single utility module may be provided with a parameter or other module in a more integrated design since in these figures the parameter modules are shown integrated; albeit they could just as well be cartridges received by a receptacle in the utility module. In addition, it will appreciated that the face of the utility module shown in FIGS. 34A-D may include either one or more integrated parameter or functionality modules or one or more module cartridges that may be received by one or more receptacles defined by the utility module as described in FIG. 10B. Alternatively, the utility module may be provided with both one or more parameter or functionality modules that have been integrated into the utility module and that are received by the utility module as cartridges in a pick and play fashion. It will also be appreciated that the face of the utility module can be changed-out to accommodate different parameter or functionality modules or cartridges or to contain other information. For instance, the face of a utility module that is designed for one parameter module may at a later date be changed out for a face that is designed for two parameter modules. This feature creates even more versatility in how the disclosed utility module may be customized for individual applications.

Figure 35:
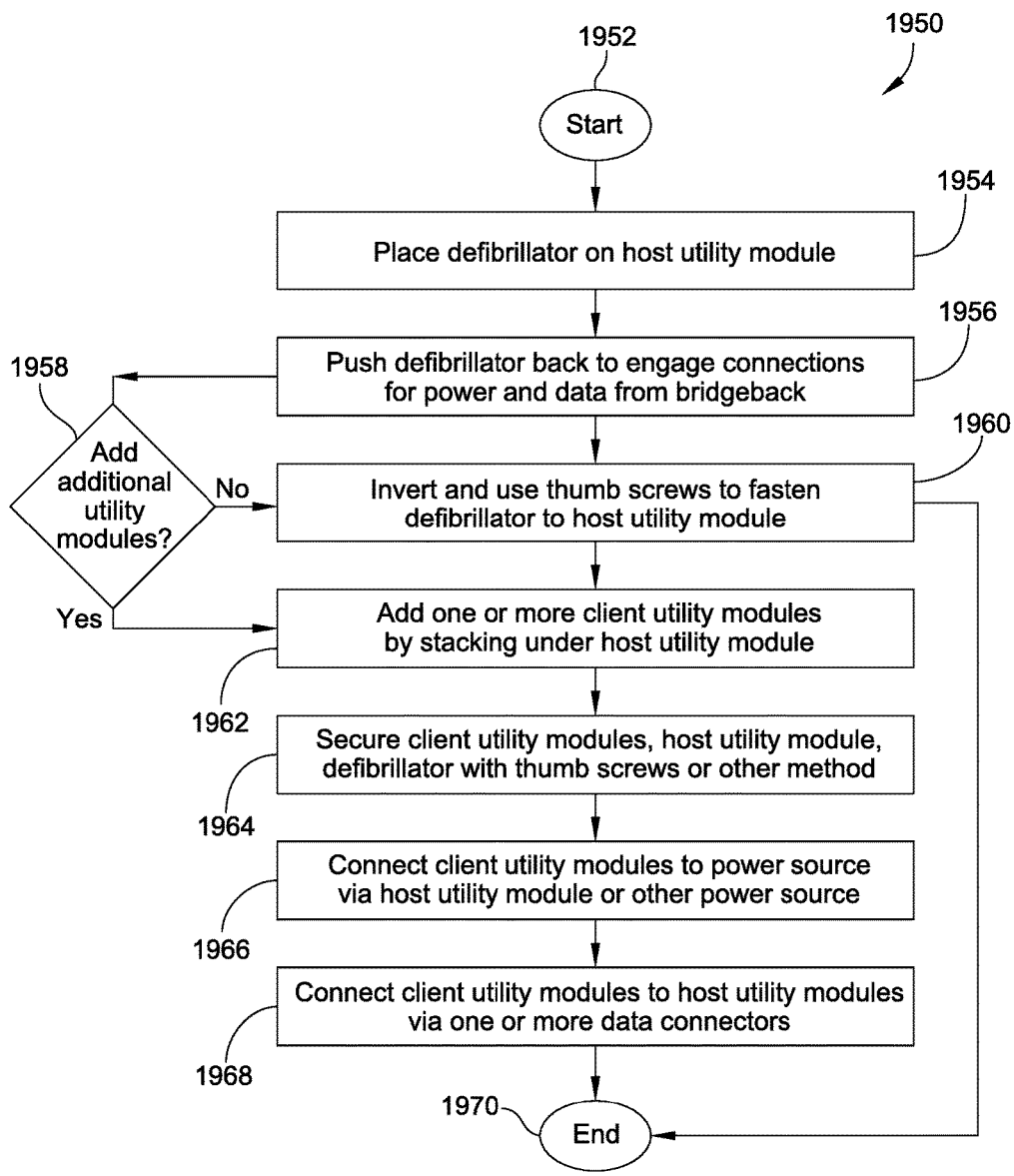
FIG. 35 is a flowchart for assembly and connection of one or more utility modules with a defibrillator for use in coaching the defibrillator.

The present disclosure also includes a connection method 1950 shown in FIG. 35 for connecting one or more utility modules to the defibrillator so that coaching may be provided to the defibrillator. The method starts at step 1952. At step 1954, a defibrillator is placed atop a host utility module. The defibrillator is then pushed 1956 back against a bridge back of a utility module to engage power and data connections to enable the defibrillator to be powered by the utility module and to enable the bidirectional flow of data between the host utility module and the defibrillator. At step 1958, a determination is made whether the defibrillator will be used with one or a plurality of utility modules. If only one utility module will be used, at step 1960, thumb screws or fasteners may be used to fasten the defibrillator to the host utility module and the method is ended 1979.

If at step 1957, it is determined that more than one utility module will be used with the defibrillator, such as the client modules discussed above, at step 1962 the additional modules are added to the host utility module by vertically stacking the one or more client modules under the host utility module. At step 1964, the client utility modules and utility module are fastened to the defibrillator as previously described using thumb screws or fasteners. At step 1966, the client utility modules are then connected to the host utility module for power, or power may be connected from another source. At step 1968, the client utility modules are connected to the host utility module with data cables and connectors and the method is ended 1970. The utility modules are now ready to coach the defibrillator when a person is in need of medical treatment requiring a defibrillator.

There is thus disclosed a utility module with the ability both communicate directly with the defibrillator and external devices and to serve as a proxy for both the defibrillator and external devices. Both abilities allows for more effective coaching both from the utility module and from external resources through the utility module. The ability of the utility module to connect external devices to a defibrillator makes the utility module a powerful vehicle for integrating external devices to a defibrillator that is being used at the scene in a defibrillation procedure. Through this integration, one or more external devices may be brought to the site of a defibrillation to observe and participate in the process. Through this disclosure, external devices are enabled to provide real time coaching to a user of a defibrillator during a defibrillator process. The inclusion of a network of resources in the defibrillation process further enables a more holistic approach to be brought to the defibrillation process as compared to conventional approaches which are largely a private affair between the rescuer and the patient. The disclosed utility module and defibrillator system makes possible the virtual participation of a network of resources in a defibrillation process.

Through this disclosure, external devices are also educated with patient and other data obtained during and in connection with the defibrillation process for use in post-defibrillation procedures, coaching education, historical studies, and other purposes. In addition, the ability of the utility module to itself directly communicate with the defibrillator enables greater participation of rescuers at the site of the defibrillation process. For example, where space constraints limit the number of rescuers that may be present in the locus of the defibrillator, the utility module provides a second locus that is distributed from the defibrillator but nonetheless in seamless communication with the defibrillator; thereby allowing rescuers who might otherwise be excluded from the process because of space limitations to participate in the defibrillation process. In these and other configurations, the disclosed utility module is seen to provide enhanced coaching and enhanced functionality to the defibrillator through the disclosed system. In addition, the utility module and defibrillator system of this disclosure enables external devices to provide defibrillators with a reserve of power to enable defibrillators to be used where power is unavailable or when the defibrillator's battery power is depleted and to enable defibrillators to deliver multiple charges more readily anywhere, anytime.

In this description, numerous details have been set forth in order to provide a thorough understanding. In other instances, well-known features have not been described in detail in order to not obscure unnecessarily the description. A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. A method comprising:
    deriving, at a utility module, coaching data from a parameter of a patient, the utility module comprising a parameter module to detect the parameter of the patient, a communication module configured to transmit data from the utility module, and a module processor configured to control the parameter module and the communication module; and
    providing, from the utility module, the coaching data to a defibrillator, the defibrillator comprising an energy storage device configured to store an electrical charge, a defibrillation port, a display, and a defibrillator processor configured to control the display and when an electrical charge is applied to the defibrillation port to defibrillate the patient, wherein the defibrillator is configured to use the coaching data to provide coaching to defibrillate the patient.

2. The method of claim 1, wherein the coaching data from the utility module to the defibrillator further comprises patient parameter data from the parameter module.

3. The method of claim 2, wherein the patient parameter data is selected from the group consisting of:
    a measurement of $CO_2$ exhaled by a patient;
    an electrical activity of the heart of a patient;
    an exchange of air between the lungs of a patient and the atmosphere;
    a pressure of the blood in a patient;
    a temperature of a patient;
    an oxygen saturation in the blood of a patient;
    a measurement of a chest compression of a patient;
    an image of the internal structure of a patient;
    an oxygen saturation in the blood in the brain of a patient; and
    the acidity or alkalinity of fluids in a patient.

4. The method of claim 2, wherein the defibrillator is configured to render the patient parameter data on the display to coach a user of the defibrillator to defibrillate the patient.

5. The method of claim 1, wherein the defibrillator uses the coaching data to provide coaching on mechanics of CPR techniques to a user of the defibrillator.

6. The method of claim 5, comprising measuring, by the parameter module, a measurement of a chest compression of a patient, wherein the coaching data is derived, at the utility module, from the measurement of the chest compression.

7. The method of claim 1, wherein the defibrillator processor is configured to use the coaching data to control when the electrical charge is applied to the defibrillation port to defibrillate the patient.

8. The method of claim 1, wherein the defibrillator comprises a speaker, and the defibrillator is configured to use the coaching data to output a voice prompt via the speaker to coach a user of the defibrillator to defibrillate the patient.

9. The method of claim 1, wherein the defibrillator is configured to use the coaching data to render a visual prompt on the display to coach a user of the defibrillator to defibrillate the patient.

10. The method of claim 1, wherein the defibrillator comprises a measurement circuit to receive physiological signals from the defibrillation port, and wherein the defibrillator is configured to provide coaching based on the physiological signals.

11. The method of claim 10, wherein the defibrillator processor comprises a detection module to detect ventricular defibrillation in the physiological signals, and wherein the defibrillator is configured to provide coaching based on detection of ventricular defibrillation.

12. The method of claim 10, comprising transmitting, from the utility module, data received from the defibrillator to one or more external devices to use in generating a portion of the coaching data.

13. The method of claim 12, comprising receiving, at the utility module, the portion of the coaching data from the one or more external devices.

14. The method of claim 12, comprising polling the defibrillator from the utility module to determine the existence of the data residing in the defibrillator to be received from the defibrillator.

15. A utility module comprising:
- a parameter module to detect a parameter of a patient, a communication module configured to transmit data from the utility module, and a module processor configured to control the parameter module and the communication module, wherein:
  - the utility module is configured for connection to a defibrillator that comprises an energy storage device configured to store an electrical charge, a defibrillation port, a display, and a defibrillator processor, wherein the defibrillator processor is configured to control the display and when an electrical charge is applied to the defibrillation port to defibrillate the patient; and
  - the utility module is configured to derive coaching data from the parameter of the patient, and to provide the coaching data to the defibrillator, wherein the defibrillator is configured to use the coaching data to provide coaching to defibrillate the patient.

16. The utility module of claim 15, wherein the coaching data from the utility module to the defibrillator further comprises patient parameter data from the parameter module.

17. The utility module of claim 15, wherein the parameter module generates patient parameter data selected from the group consisting of:
- a measurement of $CO_2$ exhaled by a patient;
- an electrical activity of the heart of a patient;
- an exchange of air between the lungs of a patient and the atmosphere;
- a pressure of the blood in a patient;
- a temperature of a patient;
- an oxygen saturation in the blood of a patient;
- a measurement of a chest compression of a patient;
- an image of the internal structure of a patient;
- an oxygen saturation in the blood in the brain of a patient; and
- the acidity or alkalinity of fluids in a patient.

18. The utility module of claim 17, wherein the coaching data is derived from the patient parameter data, and the patient parameter data comprises at least the measurement of the chest compression.

19. The utility module of claim 18, wherein the coaching data comprises at least one of coaching on speed of CPR chest compressions or depth of CPR chest compressions.

20. The utility module of claim 15, wherein the defibrillator is configured to render patient parameter data generated from the parameter of the patient on the display.

21. The utility module of claim 15, wherein the defibrillator processor is configured to use the coaching data to provide coaching on when the electrical charge should be applied to the defibrillation port to defibrillate the patient.

22. The utility module of claim 15, wherein the defibrillator comprises a speaker, and the defibrillator is configured to use the coaching data to output a voice prompt via the speaker to coach a user of the defibrillator to defibrillate the patient.

23. The utility module of claim 15, wherein the defibrillator is configured to use the coaching data to render a visual prompt on the display to coach a user of the defibrillator to defibrillate the patient.

24. The utility module of claim 15, wherein the defibrillator comprises a measurement circuit to receive physiological signals from the defibrillation port, and wherein the defibrillator is configured to provide coaching based on the physiological signals.

25. The utility module of claim 24, wherein the defibrillator processor comprises a detection module to detect ventricular defibrillation in the physiological signals, and wherein the defibrillator is configured to provide coaching based on detection of ventricular defibrillation.

26. The utility module of claim 15, wherein a portion of the coaching data is received, at the utility module, from one or more external devices.

27. The utility module of claim 26, wherein the communication module is configured to transmit data received from the defibrillator to the one or more external devices to use in generating the portion of the coaching data.

28. The utility module of claim 27, wherein the utility module is configured to poll the defibrillator to determine the existence of the data residing in the defibrillator to be received from the defibrillator.

* * * * *